(12) United States Patent
Li et al.

(10) Patent No.: US 12,133,841 B2
(45) Date of Patent: Nov. 5, 2024

(54) HETEROCYCLIC COMPOUNDS AS KINASE INHIBITORS, COMPOSITIONS COMPRISING THE HETEROCYCLIC COMPOUND, AND METHODS OF USE THEREOF

(71) Applicant: JS INNOMED HOLDINGS LTD., Grand Cayman (KY)

(72) Inventors: Qun Li, Sunnyvale, CA (US); Jintao Zhang, Naperville, IL (US); Shanzhong Jian, Shanghai (CN); Wen Xu, Shanghai (CN); Ao Li, Shanghai (CN)

(73) Assignee: JS INNOMED HOLDINGS LTD., Grand Cayman (KY)

( * ) Notice: Subject to any disclaimer, the term of this patent is extended or adjusted under 35 U.S.C. 154(b) by 835 days.

(21) Appl. No.: 17/057,168

(22) PCT Filed: May 20, 2019

(86) PCT No.: PCT/CN2019/087534
§ 371 (c)(1),
(2) Date: Nov. 20, 2020

(87) PCT Pub. No.: WO2019/223632
PCT Pub. Date: Nov. 28, 2019

(65) Prior Publication Data
US 2021/0188868 A1 Jun. 24, 2021

(30) Foreign Application Priority Data
May 22, 2018 (CN) .......................... 201810496014.5

(51) Int. Cl.
*A61K 31/407* (2006.01)
*A61K 31/4015* (2006.01)
*A61K 31/506* (2006.01)
*A61K 45/06* (2006.01)
*C07D 495/04* (2006.01)

(52) U.S. Cl.
CPC ........ *A61K 31/407* (2013.01); *A61K 31/4015* (2013.01); *A61K 31/506* (2013.01); *A61K 45/06* (2013.01); *C07D 495/04* (2013.01)

(58) Field of Classification Search
CPC .............. A61K 31/506; A61K 31/4015; A61K 31/407; C07D 495/04
See application file for complete search history.

(56) References Cited

U.S. PATENT DOCUMENTS

2016/0176896 A1* 6/2016 Cortez ............... C07K 16/2863
544/70

FOREIGN PATENT DOCUMENTS

| JP | 2015508828 A | 3/2015 | | |
|---|---|---|---|---|
| JP | 2017538768 A | 12/2017 | | |
| JP | 2018500340 A | 1/2018 | | |
| JP | 2018532737 A | 11/2018 | | |
| WO | WO 2013/130976 A1 | 9/2013 | | |
| WO | WO-2016106009 A1 * | 6/2016 | .......... | C07B 59/002 |
| WO | WO-2016106029 A1 * | 6/2016 | .......... | A61K 31/506 |

OTHER PUBLICATIONS

Adjei, A. (2001). Blocking Oncogenic Ras Signaling for Cancer Therapy. *J. Natl. Cancer Inst.*, 93(14):1062-1074.
Aviel-Ronen, S., et al. (2006). K-ras Mutations in Non-Small-Cell Lung Carcinoma: A Review. *Clin. Lung Cancer*, 8(1):30-38.
Brose, M., et al. (2002). BRAF and RAS Mutations in Human Lung Cancer and Melanoma. *Cancer Res.*, 62(23):6997-7000.
Crane, E. and Wong, K. (2013). The Therapeutic Promise of Anti-Cancer Drugs Against the Ras/Raf/MEK/ERK Pathway. *Topics in Anti-Cancer Research*, 2:63-94.
International Patent Application No. PCT/CN2019/087534: International Search Report and Written Opinion, mailed Aug. 19, 2019 (10 pages).
Kolch, W. (2005). Coordinating ERK/MAPK signalling through scaffolds and inhibitors. *Nat. Rev. Mol. Cell Biol.*, 6:827-837.
Mallon, R., et al. (2004). Identification of 4-anilino-3-quinolinecarbonitrile inhibitors of mitogen-activated protein/extracellular signal-regulated kinase 1 kinase. *Mol. Cancer Ther.*, 3(6):755-762.
Sebolt-Leopold, J. (2000). Development of anticancer drugs targeting the MAP kinase pathway. *Oncogene*, 19:6594-6599.

(Continued)

*Primary Examiner* — Craig D Ricci
*Assistant Examiner* — Janet L Coppins
(74) *Attorney, Agent, or Firm* — FINNEGAN, HENDERSON, FARABOW, GARRETT & DUNNER LLP

(57) ABSTRACT

The present disclosure provides a compound of Formula (I) and/or a stereoisomer, a tautomer, a stable isotope, or a pharmaceutically acceptable salt thereof; and therapeutic uses of these compounds. They are kinase inhibitors potentially useful in the treatment of diseases treatable, such as cancers. Also disclosed herein is a pharmaceutical composition, comprising a compound of Formula (I) and/or a stereoisomer, a tautomer, a stable isotope, or a pharmaceutically acceptable salt thereof; and a pharmaceutically acceptable carrier.

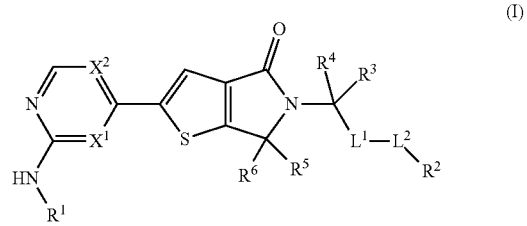

19 Claims, No Drawings

(56) References Cited

OTHER PUBLICATIONS

Sebolt-Leopold, J. (2004). MEK Inhibitors: A Therapeutic Approach to Targeting the Ras-MAP Kinase Pathway in Tumors. *Curr. Pharm. Des.*, 10(16):1907-1914.

Sebolt-Leopold, J. and Herrera, R. (2004). Targeting the Mitogen-Activated Protein Kinase Cascade to Treat Cancer. *Nat. Rev. Cancer*, 4:937-947.

Singer, G., et al. (2003). Mutations in BRAF and KRAS Characterize the Development of Low-Grade Ovarian Serous Carcinoma. *J. Natl. Cancer Inst.*, 95(6):484-486.

Thomas, N. (2006). BRAF somatic mutations in malignant melanoma and melanocytic naevi. *Melanoma Res.*, 16(2):97-103.

Yoon, S. and Seger, R. (2006). The extracellular signal-regulated kinase: Multiple substrates regulate diverse cellular functions. *Growth Factors*, 24(1):21-44.

\* cited by examiner

HETEROCYCLIC COMPOUNDS AS KINASE INHIBITORS, COMPOSITIONS COMPRISING THE HETEROCYCLIC COMPOUND, AND METHODS OF USE THEREOF

CROSS REFERENCE TO RELATED APPLICATION

This application claims the benefit of priority to Chinese Patent Application No. 201810496014.5, filed May 22, 2018.

TECHNICAL BACKGROUND

Disclosed herein are novel heterocyclic compounds that can serve as extracellular signal-regulated kinases (ERK) inhibitors. Further disclosed herein are pharmaceutical compositions, comprising at least one of such compounds, as well as methods of using at least one of such compounds in treatment of diseases modulated by ERK, such as cancers.

The Ras-Raf-Mek-Erk intracellular signaling cascade is known as a central signaling module that transmits proliferation, survival, growth and differentiation signals into the cell interior from activated receptor tyrosine kinases (RTKs) such as ErbB family, PDGF, FGF, and VEGF (Sebolt-Leopold, J. S. and Herrera, R., *Nat. Rev. Cancer,* 41:937-947, 2004; Kolch, W., *Nat. Rev. Mol. Cell Biol.,* 61:827-837, 2005). This signaling axis includes Ras, Raf, Mek (mitogen-activated protein kinase kinase), and Erk (extracellular signal-regulated kinases) proteins all occurring in highly homologous isoforms. Ras proteins (e.g, H-Ras, N-Ras, and K-Ras) are 21 kDa GTPases that are activated at the proximity sites of the intracellular kinase domains of RTKs. Raf kinases (e.g, RafA, RafB, and RafC) are intermediate downstream effectors of Ras, activated by binding to GTP-loaded Ras. Raf kinases phosphorylate Meks (Mek1 and Mek2) on two closely adjacent serine residues, S218 and S222 in the case of Mek1. Meks are dual specificity threonine/tyrosine kinases that phosphorylate threonine and tyrosine residues within the TXY motif of Erks, where T represents threonine, Y represents tyrosine, and X represents any amino acid. Erk proteins (Erk1 and Erk2), also known as MAPKs (mitogen-activated protein kinases), are serine/threonine kinases that phosphorylate more than 100 downstream cytosolic and nuclear target proteins that participate in cellular processes such as division, proliferation, migration, and apoptosis (Yoon, S. and Seger, R., *Growth Factors,* 24:21-44, 2006). These phosphorylations substantially modulate, generally stimulate, the activity of the target proteins and can profoundly alter the physiological status of the cells.

Pathological activation of Ras-Raf-Mek-Erk cascade signaling pathway is known to account for the mechanistic aspects of most human cancers, immune dysfunction, and hyper-inflammatory conditions. Activation of the signaling pathway can occur as the result of autocrine or paracrine production of excessive RTK ligands, or constitutive activation of cell surface receptors by mutation or overexpression, or more commonly through gain-of-function mutations of B-Raf and Ras family members. Oncogenic forms of Ras are reported to be associated with 30% of all human cancers. Mutations in K-Ras occur in 90% of pancreatic and in 25% to 50% of colorectal, mucinous ovarian, and non-small cell lung cancers, whereas mutations in H-Ras are common in bladder, kidney, and thyroid cancers and N-Ras mutations are found in melanoma, hepatocellular carcinoma, and hematologic malignancies (Adjei, A., *J. Natl. Cancer Inst.,* 93:1062-74, 2001; Aviel-Ronen, S., et al, *Clin Lung Cancer,* 8:30-8, 2006). B-Raf mutations occur in 66% to 70% of malignant melanomas, 70% of nonpapillary thyroid cancers, 35% of low-grade ovarian serous tumors as well as a wide range of other cancers including, for example, colorectal, thyroid, lung, breast, and ovarian cancers (Thomas, N., *Melanoma Res,* 16:97-103, 2006; Singer, G., et al, *J. Natl. Cancer Inst.,* 95:484-6, 2003; Brose, M., et al, *Cancer Res.,* 62:6997-7000, 2002).

Inhibition of the activity of Ras-Raf-Mek-Erk signaling pathway has been the focus of drug discovery, particularly for cancer treatment (Sebolt-Leopold, J., *Oncogene,* 19:16564-6599, 2000). Small-molecule inhibitors of B-Raf and Mek have been shown to effectively inhibit Ras and Raf mediated cell transformation, Erk activation and dependent processes, cell proliferation in vitro, tumor growth in vivo (Mallon, R., et al., *Mol. Cancer Ther.,* 31:755-762, 2004; Sebolt-Leopold, J., *Curr. Pharm. Des.,* 101:1907-1914, 2004; Sebolt-Leopold J. and Herrera, R., *Nat. Rev. Cancer,* 41:937-947, 2004). The demonstration of the clinical efficacy of multiple Raf and Mek small-molecule inhibitors in various types of cancers has provided an ultimate validation of targeting this signaling pathway for cancer treatment (Crane, E. and Wang, K., *Topics Anti-Cancer Res.,* 2:63-94, 2013).

Given Erk proteins' downstream position in the Ras-Raf-Mek-Erk signaling cascade, inhibition of Erks can provide an alternative strategy to modulate down the activity of the pathway. As such, there is a strong rationale to develop Erk small-molecule inhibitors as novel therapeutic agents for a broad spectrum of human cancers originated, for example, from brain, lung, colon, breast, gastric, pancreatic, head and neck, esophageal, renal, kidney, ovarian, skin, prostate, testicular, gynecological or thyroid. In addition, the Erk inhibitors may also be used to treat, for example, non-cancerous hyper-proliferative disorders (e.g., benign hyperplasia of the skin, restenosis, benign prostatic hypertrophy), pancreatitis, kidney disease, pain, diseases related to vasculogenesis or angiogenesis, acute and chronic inflammatory disease (e.g., rheumatoid arthritis, athero sclerosis, inflammatory bowel disease), skin diseases (e.g., psoriasis, eczema, and scleroderma), diabetes, diabetic retinopathy, retinopathy of prematurity, age-related macular degeneration, asthma, septic shock, T-cell mediated diseases, chronic obstructive pulmonary disease (COPD).

SUMMARY OF THE INVENTION

Disclosed herein are compounds of Formula I:

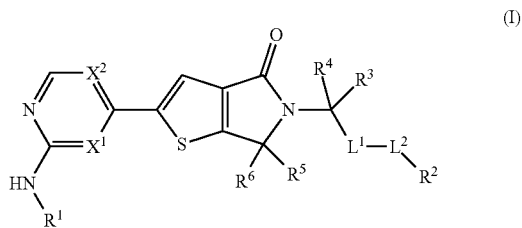

and/or a stereoisomer, tautomer, stable isotope, or pharmaceutically acceptable salt thereof, wherein $R^1$, $R^2$, $R^3$, $R^4$, $R^5$, $R^6$, $L^1$, $L^2$, $X^1$ and $X^2$ are defined herein.

$R^1$ is selected from an optionally substituted group selected from C1-C6 alkyl, C3-C8 cycloalkyl, C4-8 cycloalkenyl, saturated or unsaturated 4-8 membered heterocyclyl containing 1-2 heteroatoms selected from N, O, and S as ring members, aryl, heteroaryl containing 1-3 heteroatoms selected from N, O, and S as ring members, and wherein the optional substituents for $R^1$ are 1-4 substituents independently selected from D, halo, —OH, Oxo, CN, $N_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms independently selected from N, O, and S as ring members, —$CO_2R^7$, —$C(O)N(R^{8a}R^{8b})$, —$C(=NR^9)N(R^{8a}R^{8b})$, —$C(O)R^7$, —$SO_{0-2}R^{10}$, —$SO(=NR^9)R^{10}$, —$SO_{1-2}N(R^{8a}R^{8b})$, —$N(R^{8a}R^{8b})$, —$N(R^{8a})C(O)R^{10}$, —$N(R^{8a})C(=NR^9)R^{10}$, —$N(R^{8a})SO_{1-2}R^{10}$, —$N(R^{8c})C(O)N(R^{8a}R^{8b})$, —$N(R^{8c})C(=NR^9)N(R^{8a}R^{8b})$, —$N(R^{8c})SO_{1-2}N(R^{8a}R^{8b})$ and —$N(R^{8a})CO_2R^{10}$, wherein $R^7$, $R^{8a}$, $R^{8b}$ and $R^{8c}$ are independently H, and C1-C4 alkyl optionally substituted with 1-3 groups independently selected from D, halo, OH, $NH_2$, NHMe and $NMe_2$; $R^9$ is independently selected from H, CN, OH, C1-C4 alkyl and C1-C4 alkoxy; $R^{10}$ is C1-C4 alkyl optionally substituted with 1-3 groups independently selected from D, halo, OH, $NH_2$, NHMe and $NMe_2$; and two substituents on the same or adjacent carbon atoms of $R^1$ can optionally be taken together to form a 5-6 membered ring that can be saturated or aromatic and optionally contains 1-2 heteroatoms selected from N, O and S and can optionally be substituted with 1-2 groups independently selected from D, Me, halo, OH, oxo, C1-C4 alkoxy, $NH_2$, C1-C4 alkylamino and di(C1-C4 alkyl)amino;

$R^2$ is selected from aryl and heteroaryl containing 1-3 heteroatoms selected from N, O and S as ring members, wherein $R^2$ is optionally substituted with 1-3 substituents independently selected from D, halo, —OH, =O, CN, $N_3$, $CF_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —$CO_2R^{11}$, —$C(O)N(R^{12a}R^{12b})$, —$C(=NR^{13})N(R^{12a}R^{12b})$, —$C(O)R^{11}$, —$SO_{0-2}R^{14}$, —$SO(=NR^{13})R^{14}$, —$SO_{1-2}N(R^{12a}R^{12b})$, —$N(R^{12a}R^{12b})$, —$N(R^{12a})C(O)R^{11}$, —$N(R^{12a})C(=NR^{13})R^{11}$, —$N(R^{12a})SO_{1-2}R^{14}$, —$N(R^{12c})C(O)N(R^{12a}R^{12b})$, —$N(R^{12c})C(=NR^{13})N(R^{12a}R^{12b})$, —$N(R^{12c})SO_{1-2}N(R^{12a}R^{12b})$ and —$N(R^{12a})CO_2R^{14}$; wherein $R^{11}$, $R^{12a}$, $R^{12b}$ and $R^{12c}$ are independently selected from H, and C1-C4 alkyl optionally substituted with 1-3 groups independently selected from D, halo, OH, $NH_2$, NHMe, $NMe_2$ and C1-C4 alkoxy; $R^{13}$ is independently selected from H, CN, OH, C1-C4 alkyl, and C1-C4 alkoxy; $R^{14}$ is C1-C4 alkyl optionally substituted with 1-3 groups indepently selected from D, halo, OH, $NH_2$, NHMe, $NMe_2$ and C1-C4 alkoxy;

$R^3$ is selected from H, D and F;

$R^4$ is selected from H, D, F, and C1-C4 alkyl optionally substituted with 1-3 substituents independently selected from D, halo, —OH, =O, CN, $N_3$, —$CO_2R^{15}$, —$C(O)N(R^{16a}R^{16b})$, —$C(=NR^{17})N(R^{16a}R^{16b})$, —$C(O)R^{15}$, —$SO_{0-2}R^{18}$, —$SO(=NR^{17})R^{18}$, —$SO_{1-2}N(R^{16a}R^{16b})$, —$N(R^{16a}R^{16b})$, —$N(R^{16a})C(O)R^{15}$, —$N(R^{16a})C(=NR^{17})R^{15}$, —$N(R^{16a})SO_{1-2}R^{18}$, —$N(R^{16c})C(O)N(R^{16a}R^{16b})$, —$N(R^{16c})C(=NR^{17})N(R^{16a}R^{16b})$, —$N(R^{16c})SO_{1-2}N(R^{16a}R^{16b})$ and —$N(R^{16a})CO_2R^{18}$; wherein $R^{15}$, $R^{16a}$, $R^{16b}$ and $R^{16c}$ are independently selected from H, and C1-C4 alkyl optionally substituted with 1-3 groups independently selected from D, halo, OH, $NH_2$, NHMe, $NMe_2$ and C1-C4 alkoxy; $R^{17}$ is independently selected from H, CN, OH, C1-C4 alkyl, and C1-C4 alkoxy; $R^{18}$ is C1-C4 alkyl optionally substituted with 1-3 groups indepently selected from D, halo, OH, $NH_2$, NHMe, $NMe_2$ and C1-C4 alkoxy;

$R^5$ and $R^6$ are independently selected from H and an optionally substituted group selected from C1-C4 alkyl, C3-C6 cycloalkyl, and saturated or unsaturated 4-6 membered heterocyclyl containing 1-2 heteroatoms selected from N, O, and S as ring members; wherein the optional substituents for $R^5$ and $R^6$ are 1-3 substituents independently selected from D, halo, —OH, C1-C4 alkyl, C1-C4 alkoxy, C1-C4 haloalkyl, C1-C4 haloalkoxy, and C3-C6 cycloalkyl;

$R^2$ and $R^4$ can optionally cyclize to form an additional C5-C6 cycloalkyl ring or a 5-6 membered heterocyclic ring containing 1-2 heteroatoms selected from N, O, and S;

$R^5$ and $R^6$ can optionally cyclize to form a C3-C6 cycloalkyl ring, a 4-6 membered heterocyclic ring containing 1-2 heteroatoms selected from N, O, and S;

$L^1$ is selected from a bond, —$C(R^{19a}R^{19b})$—, —$C(O)NR^{20}$—, and —$C(R^{19a}R^{19b})NR^{20}$—, wherein $R^{19a}$, $R^{19b}$ and $R^{20}$ are independently selected from H and C1-C4 alkyl, each of which is optionally substituted with 1-3 groups independently selected from D, halo, OH, $NH_2$, NHMe, $NMe_2$ and C1-C4 alkoxy;

$L^2$ is selected from a bond and —$C(R^{21a}R^{21b})$—, wherein $R^{21a}$ and $R^{21b}$ are independently selected from H and C1-C4 alkyl optionally substituted with 1-3 groups independently selected from D, halo, OH, $NH_2$, NHMe, $NMe_2$, —$OPO_3H_2$ and C1-C4 alkoxy;

$X^1$ is selected from $CR^{22a}$ and N; wherein $R^{22a}$ is selected from H, halo, CN and C1-C3 alkyl;

$X^2$ is selected from $CR^{22b}$ and N; wherein $R^{22b}$ is selected from H, halo, CN and C1-C3 alkyl.

Also disclosed herein is a pharmaceutical composition, comprising a compound of Formula I and/or a stereoisomer, tautomer, stable isotope, or pharmaceutically acceptable salt thereof disclosed herein and a pharmaceutically acceptable carrier.

Further disclosed herein is a method of inhibiting the activity of Erk comprising contacting the protein Erk with an effective amount of a compound of Formula I and/or a pharmaceutically acceptable salt thereof disclosed herein.

Further disclosed herein is a method of treating a disease treatable by inhibition of Erk in a patient, comprising administering to the patient in recognized need of such treatment, an effective amount of a compound of Formula I and/or a pharmaceutically acceptable salt thereof disclosed herein.

Further disclosed herein is a method of treating a disease treatable by inhibition of Erk in a patient, comprising administering to the patient in recognized need of such treatment, an effective amount of a pharmaceutical composition comprising a compound of Formula I and/or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of Formula I and/or a pharmaceutically acceptable salt thereof disclosed herein and a pharmaceutically acceptable carrier. In some embodiments, the cancer is colon cancer, gastric cancer, leukemia, lymphoma, melanoma, or pancreatic cancer.

Further disclosed herein is a method of treating an inflammatory disease in a patient, comprising administering to the patient in recognized need of such treatment, an effective amount of a pharmaceutical composition comprising a compound of Formula I and/or a pharmaceutically acceptable salt thereof disclosed herein and a pharmaceutically acceptable carrier. In some embodiments, the inflammatory disease is rheumatoid arthritis, psoriasis, or eczema.

Further disclosed herein is a use of a compound of Formula I and/or a pharmaceutically acceptable salt thereof in preparation of a medication for treating a disease responsive to inhibition of Erk, such as a cancer or an inflammatory disease. In some embodiments, the cancer is colon cancer, gastric cancer, leukemia, lymphoma, melanoma, or pancreatic cancer. In some embodiments, the inflammatory disease is rheumatoid arthritis, psoriasis, or eczema.

Further disclosed herein are compounds of Formula I and the subgenera of Formula I described herein, as well as pharmaceutically acceptable salts of these compounds, and all stereoisomers (including diastereoisomers and enantiomers and enantiomers), tautomers and isotopically enriched versions thereof (including deuterium substitutions). Compounds of the present disclosure also comprise salts of compounds of Formula I (or subformula thereof). These compounds can be used to treat conditions responsive to ERK inhibition, such as those described herein, and for use in the preparation of a medicament for treating these disorders. The pharmaceutical compositions and methods described herein can also be used with or formulated with a co-therapeutic agent; for example, compounds of Formula I and sub-formula thereof can be used with or formulated with inhibitors of B-RAF and other therapeutic agents as further described herein.

Further disclosed are methods of making the compounds of Formula I as well as key intermediate compounds useful for making the compounds of the disclosure.

As used herein, the following words, phrases and symbols are generally intended to have the meanings as set forth below, except to the extent that the context in which they are used indicates otherwise. The following abbreviations and terms have the indicated meanings throughout.

DETAILED DESCRIPTION

The following definitions apply unless otherwise provided or apparent from context:

A dash ("-") that is not between two letters or symbols is used to indicate a point of attachment for a substituent. For example, —CONR$_a$R$_b$ is attached through the carbon atom.

Unless clearly indicated otherwise, use of the terms "a", "an" and the like refers to one or more.

The term "halogen" or "halo" herein refers to fluorine (F), chlorine (Cl), bromine (Br) or iodine (I). Halogen-substituted groups and moieties, such as alkyl substituted by halogen (haloalkyl) can be mono-, poly-, or per-halogenated. Chloro and fluoro are examples of halo substituents on alkyl or cycloalkyl groups, unless otherwise specified; fluoro, chloro, and bromo are often used, for example, on aryl or heteroaryl groups, unless otherwise provided.

The term "heteroatoms" or "hetero atoms" as used herein refers to nitrogen (N) or oxygen (O) or sulfur (S) atoms, in particular nitrogen or oxygen, unless otherwise provided.

The term "optional" or "optionally" used herein means that the subsequently described event or circumstance may or may not occur, and that the description includes instances where the event or circumstance occurs and instances in which it does not. For example, "alkyl optionally substituted with X" encompasses both "alkyl without substitution of X" and "alkyl substituted with X". It will be understood by those skilled in the art, with respect to any group containing one or more substituents, that such groups are not intended to introduce any substitution or substitution patterns that are sterically impractical, synthetically non-feasible and/or inherently unstable in water at room temperature for at least long enough to be administered as a pharmaceutical agent. When multiple substituents are present, the substituents are selected independently unless otherwise indicated, so where 2 or 3 substituents are present, for example, those substituents may be the same or different.

In some embodiments, "substituted with at least one group" refers to one hydrogen on the designated atom or group being replaced with one selection from the indicated group of substituents. In some embodiments, "substituted with at least one group" refers to two hydrogens on the designated atom or group being independently replaced with two selections from the indicated group of substituents. In some embodiments, "substituted with at least one group" refers to three hydrogens on the designated atom or group being independently replaced with three selections from the indicated group of substituents. In some embodiments, "substituted with at least one group" refers to four hydrogens on the designated atom or group being independently replaced with four selections from the indicated group of substituents.

The term "alkyl" herein refers to a hydrocarbon group chosen from linear and branched saturated hydrocarbon groups having up to 18 carbon atoms, such as from 1 to 12, further such as from 1 to 8, even further such as from 1 to 6, carbon atoms. Representative examples of alkyl include, but not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like.

A substituted alkyl is an alkyl group containing one or more substituents in place of hydrogen atoms of the unsubstituted alkyl, such as one, two or three substituents, or 1-4 substituents, up to the number of hydrogens present on the unsubstituted alkyl group. Suitable substituents for alkyl groups, if not otherwise specified, may be selected from halogen, D, CN, oxo, hydroxyl, substituted or unsubstituted C1-C4 alkxoy, substituted or unsubstituted C3-C6 cycloalkyl, substituted or unsubstituted 3-7 membered heterocycloalkyl containing 1 or 2 heteroatoms selected from N, O and S as ring members, substituted or unsubstituted aryl, substituted or unsubstituted heteroaryl containing 1 to 3 heteroatoms selected from N, O and S as ring members, amino, —NH(C1-C4 alkyl), —N(C1-C4 alkyl)$_2$, —S(=O)$_{0-2}$(C1-C4 alkyl), —S(=NR)(=O) (C1-C4 alkyl), —C(=O)(C1-C4 alkyl), —C(=NOH)(C1-C4 alkyl), —CO$_2$H, —CO$_2$(C1-C4 alkyl), —S(=O)$_{1-2}$NH$_2$, —S(=O)$_{1-2}$NH(C1-C4 alkyl), —S(=O)$_{1-2}$N(C1-C4 alkyl)$_2$, —CONH$_2$, —C(=O)NH(C1-C4 alkyl), —C(=O)N(C1-C4 alkyl)$_2$, —C(=NOH)NH(C1-C4 alkyl), —OC(=O)(C1-C4 alkyl), —NHC(=O)(C1-C4 alkyl), —NHC(=NOH)(C1-C4 alkyl), —NH(C=O)NH$_2$, —NHC(=O)O(C1-C4 alkyl), —NHC(=O)NH(C1-C4 alkyl), NHC(=NOH)NH(C1-C4 alkyl), —NHS(=O)$_{1-2}$(C1-C4 alkyl), —NHS(=O)$_{1-2}$NH$_2$, and —NHS(=O)$_{1-2}$NH(C1-C4 alkyl); wherein the substituents for substituted C1-C4 alkoxy, substituted C3-C6 cycloalkyl, substituted 3-7 membered heterocycloalkyl, substituted aryl, and substituted heteroaryl are up to three groups independently selected from halogen, D, CN, C1-C4 alkyl, C1-C4 haloalkyl, oxo, hydroxy, C1-C4 alkoxy, amino, —NH(C1-C4 alkyl), —N(C1-C4 alkyl)$_2$. Substituents for alkyl groups, unless otherwise specified, include, for example, halogen, CN, oxo, hydroxy, C1-C4 alkoxy, C3-C6 cycloalkyl, phenyl, amino, —NH(C1-C4 alkyl), —N(C1-C4 alkyl)$_2$, C1-C4 alkylthio, C1-C4 alkylsulfonyl, —C(=O)

(C1-C4 alkyl), —CO₂H, —CO₂(C1-C4 alkyl), —OC(=O) (C1-C4 alkyl), —NHC(=O)(C1-C4 alkyl) and —NHC (=O)O(C1-C4 alkyl).

The term "alkoxy" herein refers to a straight or branched alkyl group comprising from 1 to 18 carbon atoms attached through an oxygen bridge such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Typically, alkoxy groups comprise from 1 to 6 carbon atoms, more commonly 1 to 4 carbon atoms, attached through the oxygen bridge.

A "substituted alkoxy" is an alkoxy group containing one or more, such as one, two or three substituents on the alkyl portion of the alkoxy. Unless otherwise specified, suitable substituents are selected, for example, from the substituents listed above for alkyl groups, except that hydroxyl and amino are not normally present on the carbon that is directly attached to the oxygen of the substituted alkoxy group.

The term "alkenyl" herein refers to a hydrocarbon group selected from linear and branched hydrocarbon groups, comprising at least one C=C double bond and from 2 to 18, such as from 2 to 6, carbon atoms. Examples of the alkenyl group may be selected from ethenyl or vinyl (—CH=CH₂), prop-1-enyl (—CH=CHCH₃), prop-2-enyl (—CH₂CH=CH₂), 2-methylprop-1-enyl, buta-1-enyl, buta-2-enyl, buta-3-enyl, buta-1,3-dienyl, 2-methylbuta-1,3-diene, hex-1-enyl, hex-2-enyl, hex-3-enyl, hex-4-enyl, and hexa-1,3-dienyl groups. The point of attachment can be on the unsaturated carbon or saturated carbon.

A "substituted alkenyl" is an alkenyl group containing one or more substituents in place of hydrogen atoms of the unsubstituted alkenyl, such as one, two or three substituents, or 1-4 substituents, up to the number of hydrogens present on the unsubstituted alkenyl group. Unless otherwise specified, suitable substituents are selected, for example, from the substituents listed above for alkyl groups.

The term "alkynyl" herein refers to a hydrocarbon group selected from linear and branched hydrocarbon groups, comprising at least one C≡C triple bond and from 2 to 18, such as from 2 to 6 carbon atoms. Examples of the alkynyl group include ethynyl (—C≡CH), 1-propynyl (—C≡CCH₃), 2-propynyl (propargyl, —CH₂C≡CH), 1-butynyl, 2-butynyl, and 3-butynyl groups. The point of attachment can be on the unsaturated carbon or saturated carbon.

A "substituted alkynyl" is an alkynyl group containing one or more substituents in place of hydrogen atoms of the unsubstituted alkynyl, such as one, two or three substituents, or 1-4 substituents, up to the number of hydrogens present on the unsubstituted alkynyl group. Unless otherwise specified, suitable substituents are selected, for example, from the substituents listed above for alkyl groups.

The term "alkylene" refers to a divalent alkyl group having 1 to 10 carbon atoms, and two open valences to attach to other molecular components. The two molecular components attached to an alkylene can be on the same carbon atom or on different carbon atoms; thus for example propylene is a 3-carbon alkylene that can be 1,1-disubstituted, 1,2-disubstituted or 1,3-disubstituted. Unless otherwise provided, alkylene refers to moieties having 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene and the like. A "substituted alkylene" is an alkylene group containing one or more, such as one, two or three substituents; unless otherwise specified, suitable substituents are selected, for example, from the substituents described as suitable for alkyl groups.

Similarly, "alkenylene" and "alkynylene" refer to alkylene groups having a double bond or a triple bond, respectively; they are typically 2-6 and often 2-4 carbon atoms in length, and can be substituted as explained for alkylene groups generally.

The term "haloalkyl" refers to an alkyl as defined herein, which is substituted by one or more halo groups as defined herein. Unless otherwise specified, the alkyl portion of the haloalkyl has 1-4 carbon atoms. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 6, or 4, or 3, or 2 halo groups. Examples of haloalkyl, not limited to, include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. For example, haloalkyl groups, unless specified otherwise, include monofluoro-, difluoro- and trifluoro-substituted methyl and ethyl groups, e.g. CF₃, CF₂H, CFH₂ and CH₂CF₃.

The term "alkoxy" refers to alkyl-O—, wherein alkyl is as defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable substituents are selected from the substituents listed above for alkyl groups, except that hydroxyl and amino are not normally present on the carbon that is directly attached to the oxygen of the substituted "alkyl-O" group.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyloxy groups have 1-4 carbon atoms, and up to three halogens, e.g., monofluoro, difluoro and trifluoro substituted methoxy groups and ethoxy groups.

The term "cycloalkyl" herein refers to a hydrocarbon group selected from saturated and partially unsaturated cyclic hydrocarbon groups containing 3 to 20 carbon atoms, comprising monocyclic and polycyclic (e.g., bicyclic and tricyclic, admantanyl and spirocycloalkyl) groups. Monocycloalkyl groups are cyclic hydrocarbon groups containing 3 to 20 carbon atoms, such as having 3 to 8 carbon atoms, examples of monocyclic cycloalkyl include, but are not limited to, cyclopropyl, cyclobutyl, cyclopentyl, cyclohexyl, cycloheptyl, cyclooctyl, cyclodecanyl, cyclodocecanyl, and cyclohexenyl; Bicycloalkyl groups include bridged bicycloalkyl, fused bicycloalkyl and spirocycloalkyls. Bridged bicycloalkyl contains a monocyclic cycloalkyl ring where two non-adjacent carbon atoms of the monocyclic ring are linked by an alkylene bridge of one to three additional carbon atoms (i.e. a bridging group of the form —(CH₂)n-, where n is 1, 2, 3). Representative examples of bridged bicycloalkyl include, but are not limited to, bicyclo[2.2.1]heptenes, bicyclo[3.1.1]heptanes, bicyclo[2.2.1]heptanes, bicyclo[2.2.2]octane, bicyclo[3.2.2]nonane, bicyclo[3.3.1]nonane, and bicycle[4.2.1]nonane, etc. Fused bicycloalkyl contains a monocyclic cycloalkyl ring fused to either a phenyl, a monocyclic cycloalkyl, or a monocyclic heteroaryl. Representative fused bicycloalkyl include, but are not limited to, bicyclo[4.2.0] octa-1,3,5-triene, 2,3-dihydro-1H-indene, 6,7-dihydro-5H-cyclopenta[b]pyridine, 5,6-dihydro-4H-cyclopenta[b]thiophene, and decahydronaphthalene, etc. Spirocycloalkyl contains two monocyclic ring systems which share a carbon atom forming a bicyclic ring system. Representative spirocycloalkyls include, but are not limited to,

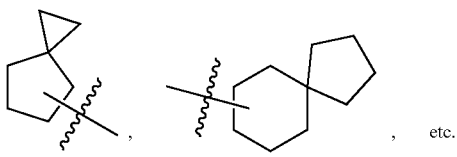

Bicyclic cycloalkyl groups are, for example, having 7 to 12 carbon atoms, mono-cycloalkyl or bicycloalkyl is attached to the parent molecular moiety through any carbon atom contained within the cycloalkyl ring. Tricycloalkyl groups include bridged tricycloalkyl as used herein referring to 1) a bridged bicycloalkyl ring where two non-adjacent carbon atoms of the bridged bicycloalkyl ring are linked by an alkylene bridge of one to three additional carbon atoms (i.e. a bridging group of the form —(CH$_2$)n-, where n is 1, 2, 3), or 2) a fused bicycloalkyl ring where two unshared ring atoms on each ring are linked by an alkylene bridge of one to three additional carbon atoms (i.e. a bridging group of the form —(CH$_2$)n-, where n is 1, 2, 3), wherein, the described "a fused bicycloalkyl ring" refers to a mono-cycloalkyl ring fused to a mono-cycloalkyl ring. Examples of bridged tricycloalkyl groups include, but is not limited to, admantanyl

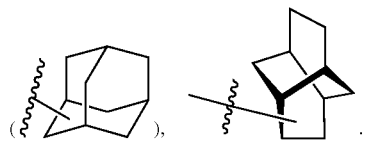

Bridged tricycloalkyl, as used herein, is appended to the parent molecular moiety through any ring atom. The described ring atom specifically refers to the carbon atom on the ring skeleton. The cycloalkyl may be saturated or have at least one double bond (i.e. partially unsaturated), but is not fully conjugated, and is not aromatic, as aromatic is defined herein. The cycloalkyl may be substituted with at least one hetero atom selected, for example, from O, S, and N.

A "substituted cycloalkyl" is a cycloalkyl group substituted by 1-3 (one, two, three), or more than three substituents, up to the number of hydrogens on the unsubstituted group. Typically, a substituted cycloalkyl will have 1-4 or 1-2 substituents. Unless otherwise specified, suitable substituents are selected, for example, from the substituents listed above for alkyl groups.

The term "heterocycloalkyl," "heterocyclyl," or "heterocyclic" herein refers to "cycloalkyl" as defined above with at least one ring carbon atom being replaced by a heteroatom independently selected from O, N, and S. Heterocyclyl contains, for example, 1, 2, 3, or 4 heteroatoms, and the N, C or S can independently be oxidized in the cyclic ring system. The N atom can further be substituted to form tertiary amine or ammonium salts. The point of attachment of heterocyclyl can be on the heteroatom or carbon. "Heterocyclyl" herein also refers to a 5- to 7-membered saturated or partially unsaturated carbocyclic ring comprising at least one heteroatom selected, for example, from N, O, and S (heterocyclic ring) fused with 5-, 6-, and/or 7-membered cycloalkyl, heterocyclic or carbocyclic aromatic ring, provided that the point of attachment is at the heterocyclic ring when the heterocyclic ring is fused with a carbocyclic aromatic ring, and that the point of attachment can be at the cycloalkyl or heterocyclic ring when the heterocylic ring is fused with cycloalkyl. "Heterocyclyl" herein also refers to an aliphatic spirocyclic ring comprising at least one heteroatom selected, for example, from N, O, and S. The rings may be saturated or have at least one double bond (i.e. partially unsaturated). The heterocyclyl may be substituted with, for example, oxo. The point of the attachment may be carbon or heteroatom. A heterocyclyl is not a heteroaryl as defined herein.

Examples of the heterocycle include, but are not limited to, pyrrolidinyl, imidazolidinyl, pyrazolidinyl, piperidinyl, piperidinyl, piperazinyl, pyranyl, morpholinyl, oxiranyl, aziridinyl, thiiranyl, azetidinyl, oxetanyl, thietanyl, dithietanyl, dihydropyridinyl, tetrahydropyridinyl, thiomorpholinyl, thioxanyl, homopiperazinyl, homopiperidinyl, azepanyl, oxepanyl, thiepanyl, oxathianyl, dioxepanyl, oxathiepanyl, oxaazepanyldithiepanyl, thiazepanyl and diazepane, dithianyl, azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, indolinyl, dioxanyl, pyrazolinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycles also include ring systems substituted with one or more oxo moieties, such as piperidinyl N-oxide, morpholinyl-N-oxide, 1-oxo-1-thiomorpholinyl, 1,1-dioxo-1-thiomorpholinyl,

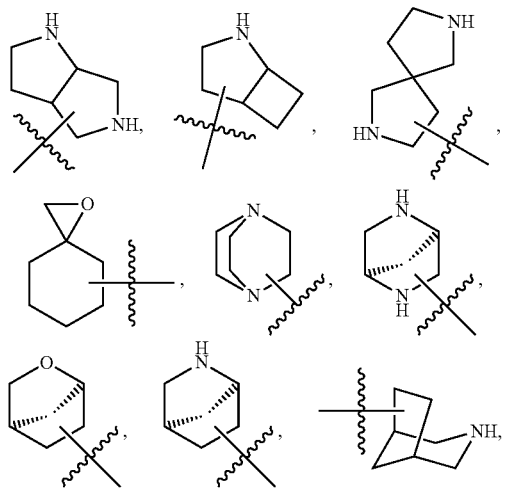

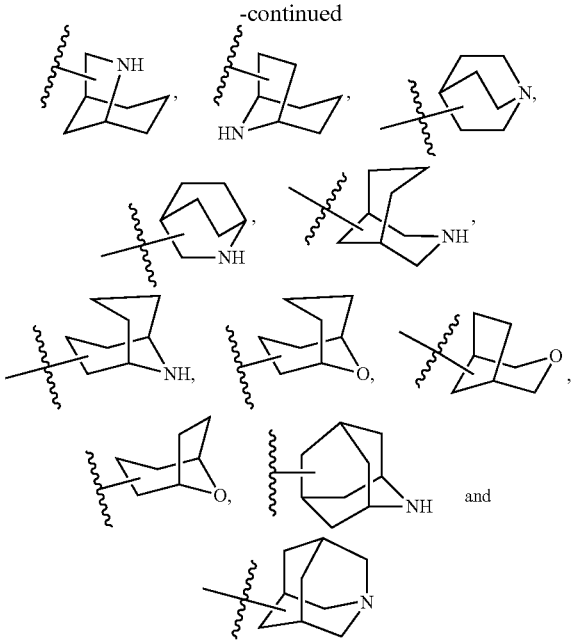

A "substituted heterocyclyl" is a heterocyclyl group independently substituted by 1-5 (such as one, or two, or three) substituents selected from the substituents described above as suitable for an alkyl group, unless otherwise specified.

The term "aryl" refers to an aromatic hydrocarbon group having 5-15 carbon atoms in the ring portion. Typically, aryl refers to a group selected from 5- and 6-membered carbocyclic aromatic rings, for example, phenyl; bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems, wherein at least one ring is carbocyclic and aromatic, for example, fluorene.

In some embodiments, the aryl group is selected from 5 and 6-membered carbocyclic aromatic rings fused to a 5- to 7-membered cycloalkyl or heterocyclic ring (as defined in "heterocyclyl" or "heterocyclic" below) optionally comprising at least one heteroatom selected, for example, from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring (e.g., a heteroaryl as defined below), the resulting ring system is heteroaryl, not aryl, as defined herein.

A "substituted aryl" is an aryl group having one or more substituents on the aryl ring replacing a hydrogen atom that would be on the unsubstituted aryl, typically 1-5 substituents, selected from the substituents described above as suitable for an alkyl group, unless otherwise specified.

The term "heteroaryl" herein refers to a group selected from 5- to 7-membered aromatic, monocyclic rings comprising at least one heteroatom, for example, from 1 to 4, or, in some embodiments, from 1 to 3, heteroatoms, selected, for example, from N, O, and S, with the remaining ring atoms being carbon; 8- to 12-membered bicyclic rings comprising at least one heteroatom, for example, from 1 to 4, or, in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in the aromatic ring, and with the point of attachment being on any ring and being on either carbon or the heteroatom; and 11- to 14-membered tricyclic rings comprising at least one heteroatom, for example, from 1 to 4, or in some embodiments, from 1 to 3, or, in other embodiments, 1 or 2, heteroatoms, selected, for example, from N, O, and S, with the remaining ring atoms being carbon and wherein at least one ring is aromatic and at least one heteroatom is present in an aromatic ring, and with the point of attachment being on any ring.

In some embodiments, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

In some embodiments, the heteroaryl group includes a 5- to 7-membered heterocyclic aromatic ring fused to a 5- to 7-membered aryl ring. For such fused, bicyclic heteroaryl ring systems wherein only one of the rings comprises at least one heteroatom, the point of attachment may be at the heteroaromatic ring or at the aryl ring. Non-limiting examples include quinolinyl and quinazolinyl.

In some embodiments, the heteroaryl group includes a 5- to 7-membered heterocyclic aromatic ring fused to another 5- to 7-membered heterocyclic aromatic ring. Non-limiting examples include 1H-pyrazolo[3,4-b]pyridinyl and 1H-pyrrolo[2,3-b]pyridinyl.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, pyridyl, cinnolinyl, pyrazinyl, pyrimidinyl, imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrimidinyl, pyrrolyl, triazolyl, quinolinyl, isoquinolinyl, pyrazolyl, pyrrolopyridinyl (such as 1H-pyrrolo[2,3-b]pyridin-3-yl), pyrazolopyridinyl (such as 1H-pyrazolo[3,4-b]pyridin-3-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

A "substituted heteroaryl" is a heteroaryl group having one or more substituents on the heteroaryl ring replacing a hydrogen atom that would be on the unsubstituted heteroaryl, typically 1, 2 or 3 substituents, selected from the substituents described above as suitable for an alkyl group, unless otherwise specified.

Compounds disclosed herein may contain an asymmetric center and may thus exist as enantiomers. Where the compounds disclosed herein possess two or more asymmetric centers, they may additionally exist as diastereomers. Enantiomers and diastereomers fall within the broader class of stereoisomers. It is well-known in the art how to prepare optically active forms, such as by resolution of materials or by asymmetric synthesis. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

When the compounds disclosed herein contain olefinic double bonds, unless specified otherwise, such double bonds are meant to include both E and Z geometric isomers.

"A pharmaceutically acceptable salt" includes, but is not limited to, salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—(CH$_2$)n-COOH, wherein n is selected from 0 to 4. Similarly, examples of pharmaceutically acceptable cations include, but are not limited to, sodium, potassium, calcium, aluminum, lithium, and ammonium.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with a acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" or "alleviation" refers to administering at least one compound and/or at least one stereoisomer thereof, if any, and/or at least one pharmaceutically acceptable salt thereof disclosed herein to a subject in recognized need thereof that has, for example, cancer.

The term "effective amount" refers to an amount of at least one compound and/or at least one stereoisomer thereof, if any, and/or at least one pharmaceutically acceptable salt thereof disclosed herein effective to "treat," as defined above, a disease or disorder in a subject.

When the term "about" is sued to modify a numerical value, it means a variance of 5% of the numerical value. When the term "about" is used to modify a numeric range, it means a variance of 5% for the lower limit and upper limit.

Various embodiments of the invention are described herein. It will be recognized that features specified in each embodiment may be combined with other specified features to provide further embodiments of the present invention. The following enumerated embodiments are representative of the invention.

Embodiment 1. Disclosed herein are compounds of Formula I:

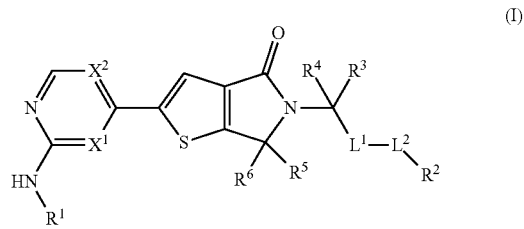

(I)

and/or a stereoisomer, tautomer, stable isotopes, or pharmaceutically acceptable salt thereof, wherein $R^1$, $R^2$, $R^3$, $R^4$, $R^5$, $R^6$, $L^1$, $L^2$, $X^1$ and $X^2$ are defined herein.

$R^1$ is selected from an optionally substituted group selected from C1-C6 alkyl, C3-C8 cycloalkyl, C4-8 cycloalkenyl, saturated or unsaturated 4-8 membered heterocyclyl containing 1-2 heteroatoms selected from N, O, and S as ring members, aryl, heteroaryl containing 1-3 heteroatoms selected from N, O, and S as ring members, and wherein the optional substituents for $R^1$ are 1-4 substituents independently selected from D, halo, —OH, Oxo, CN, N$_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms independently selected from N, O, and S as ring members, —CO$_2$R$^7$, —C(O)N(R$^{8a}$R$^{8b}$), —C(=NR$^9$)N(R$^{8a}$R$^{8b}$), —C(O)R$^7$, —SO$_{0-2}$R$^{10}$, —SO(=NR$^9$)R$^{10}$, —SO$_{1-2}$N(R$^{8a}$R$^{8b}$), —N(R$^{8a}$R$^{8b}$), —N(R$^{8a}$)C(O)R$^{10}$, —N(R$^{8a}$)C(=NR$^9$)R$^{10}$, —N(R$^{8a}$)SO$_{1-2}$R$^{10}$, —N(R$^{8c}$)C(O)N(R$^{8a}$R$^{8b}$), —N(R$^{8c}$)C(=NR$^9$)N(R$^{8a}$R$^{8b}$), —N(R$^{8c}$)SO$_{1-2}$N(R$^{8a}$R$^{8b}$) and —N(R$^{8a}$)CO$_2$R$^{10}$, wherein R$^7$, R$^{8a}$, R$^{8b}$ and R$^{8c}$ are independently H, or C1-C4 alkyl optionally substituted with 1-3 groups independently selected from D, halo, OH, NH$_2$, NHMe and NMe$_2$; R$^9$ is independently selected from H, CN, OH, C1-C4 alkyl and C1-C4 alkoxy; R$^{10}$ is C1-C4 alkyl optionally substituted with 1-3 groups independently selected from D, halo, OH, NH$_2$, NHMe and NMe$_2$; and two substituents on the same or adjacent carbon atoms of R$^1$ can optionally be taken together to form a 5-6 membered ring that can be saturated or aromatic and optionally contains 1-2 heteroatoms selected from N, O and S and can optionally be substituted with 1-2 groups independently selected from D, Me, halo, OH, oxo, C1-C4 alkoxy, NH$_2$, C1-C4 alkylamino and di(C1-C4 alkyl)amino;

$R^2$ is selected from aryl and heteroaryl containing 1-3 heteroatoms selected from N, O and S as ring members, wherein R$^2$ is optionally substituted with 1-3 substituents independently selected from of D, halo, —OH, =O, CN, N$_3$, CF$_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —CO$_2$R$^{11}$, —C(O)N(R$^{12a}$R$^{12b}$), —C(=NR$^{13}$)N(R$^{12a}$R$^{12b}$), —C(O)R$^{11}$, —SO$_{0-2}$R$^{14}$, —SO(=NR$^{13}$)R$^{14}$, —SO$_{1-2}$N(R$^{12a}$R$^{12b}$), —N(R$^{12a}$R$^{12b}$), —N(R$^{12a}$)C(O)R$^{11}$, —N(R$^{12a}$)C(=NR$^{13}$)R$^{11}$, —N(R$^{12a}$)SO$_{1-2}$R$^{14}$, —N(R$^{12c}$)C(O)N(R$^{12a}$R$^{12b}$), —N(R$^{12c}$)C(=NR$^{13}$)N(R$^{12a}$R$^{12b}$), —N(R$^{12c}$)SO$_{1-2}$N(R$^{12a}$R$^{12b}$) and —N(R$^{12a}$)CO$_2$R$^{14}$; wherein R$^{11}$, R$^{12a}$, R$^{12b}$ and R$^{12c}$ are independently selected from H, and C1-C4 alkyl optionally substituted with 1-3 groups independently selected from D, halo, OH, NH₂, NHMe, NMe₂ and C1-C4 alkoxy; R¹³ is independently selected from H, CN, OH, C1-C4 alkyl, and C1-C4 alkoxy; R¹⁴ is C1-C4 alkyl optionally substituted with 1-3 groups indepently selected from D, halo, OH, NH₂, NHMe, NMe₂ and C1-C4 alkoxy;

R³ is selected from H, D and F;

R⁴ is selected from H, D, F, and C1-C4 alkyl optionally substituted with 1-3 substituents independently selected from D, halo, —OH, =O, CN, N₃, —CO₂R¹⁵, —C(O)N(R¹⁶ᵃR¹⁶ᵇ), —C(=NR¹⁷)N(R¹⁶ᵃR¹⁶ᵇ), —C(O)R¹⁵, —SO₀₋₂ R¹⁸, —SO(=NR¹⁷)R¹⁸, —SO₁₋₂N(R¹⁶ᵃR¹⁶ᵇ), —N(R¹⁶ᵃR¹⁶ᵇ), —N(R¹⁶ᵃ)C(O)R¹⁵, —N(R¹⁶ᵃ)C(=NR¹⁷)R¹⁵, —N(R¹⁶ᵃ)SO₁₋₂R¹⁸, —N(R¹⁶ᶜ)C(O)N(R¹⁶ᵃR¹⁶ᵇ), —N(R¹⁶ᶜ)C(=NR¹⁷)N(R¹⁶ᵃR¹⁶ᵇ), —N(R¹⁶ᶜ)SO₁₋₂N(R¹⁶ᵃR¹⁶ᵇ) and —N(R¹⁶ᵃ)CO₂R¹⁸; wherein R¹⁵, R¹⁶ᵃ, R¹⁶ᵇ and R¹⁶ᶜ are independently selected from H, and C1-C4 alkyl optionally substituted with 1-3 groups independently selected from D, halo, OH, NH₂, NHMe, NMe₂ and C1-C4 alkoxy; R¹⁷ is independently selected from H, CN, OH, C1-C4 alkyl, and C1-C4 alkoxy; R¹⁸ is C1-C4 alkyl optionally substituted with 1-3 groups indepently selected from D, halo, OH, NH₂, NHMe, NMe₂ and C1-C4 alkoxy;

R⁵ and R⁶ are independently selected from H and an optionally substituted group selected from C1-C4 alkyl, C3-C6 cycloalkyl, and saturated or unsaturated 4-6 membered heterocyclyl containing 1-2 heteroatoms selected from N, O, and S as ring members; wherein the optional substituents for R⁵ and R⁶ are 1-3 substituents independently selected from D, halo, —OH, C1-C4 alkyl, C1-C4 alkoxy, C1-C4 haloalkyl, C1-C4 haloalkoxy, and C3-C6 cycloalkyl;

R² and R⁴ can optionally cyclize to form an additional C5-C6 cycloalkyl ring or a 5-6 membered heterocyclic ring containing 1-2 heteroatoms selected from N, O, and S;

R⁵ and R⁶ can optionally cyclize to form a C3-C6 cycloalkyl ring, a 4-6 membered heterocyclic ring containing 1-2 heteroatoms selected from N, O, and S;

L¹ is selected from a bond, —C(R¹⁹ᵃR¹⁹ᵇ)—, —C(O)NR²⁰—, and —C(R¹⁹ᵃR¹⁹ᵇ)NR²⁰—, wherein R¹⁹ᵃ, R¹⁹ᵇ and R²⁰ are independently selected from H and C1-C4 alkyl, each of which is optionally substituted with 1-3 groups independently selected from D, halo, OH, NH₂, NHMe, NMe₂ and C1-C4 alkoxy;

L² is selected from a bond and —C(R²¹ᵃR²¹ᵇ)—, wherein R²¹ᵃ and R²¹ᵇ are independently selected from H and C1-C4 alkyl optionally substituted with 1-3 groups independently selected from D, halo, OH, NH₂, NHMe, NMe₂, —OPO₃H₂ and C1-C4 alkoxy;

X¹ is selected from CR²²ᵃ and N; wherein R²²ᵃ is selected from H, halo, CN and C1-C3 alkyl;

X² is selected from CR²²ᵇ and N; wherein R²²ᵇ is selected from H, halo, CN and C1-C3 alkyl.

Embodiment 2. The compound according to embodiment 1 or a pharmaceutically acceptable salt thereof, wherein X¹ and X² are N.

Embodiment 3. The compound according to embodiment 1 or a pharmaceutically acceptable salt thereof, wherein X¹ is CH and X² is CR²²ᵇ, wherein R²²ᵇ is selected from H, halo, CN and C1-C3 alkyl.

Embodiment 4. The compound according to embodiment 1 or a pharmaceutically acceptable salt thereof, wherein X¹ is N and X² is CR²²ᵇ, wherein R²ᵇ² is selected from H, halo, CN and C1-C3 alkyl.

Embodiment 5. The compound according to embodiments 1-4 or a pharmaceutically acceptable salt thereof, wherein R¹ is selected from phenyl, pyridine, pyridone, pyrazine, pyridazine, pyrazole, triazole, tetrazole, thiazole, oxazole, imidazole, isothiazole, isoxazole, furan, 1,2,5-oxadiazole (furazan), and thiophene, each of which is optionally substituted with one or two groups independently selected from Oxo, D, halo, CN, hydroxy, C1-C4 alkoxy, C1-C4 alkyl, C1-C4 haloalkyl, C1-C4 hydroxyalkyl, C1-C4 haloalkoxy, C3-C6-cycloalkyl.

Embodiment 6. The compound according to embodiments 1-5 or a pharmaceutically acceptable salt thereof, wherein R¹ is selected from R¹ᵃ, wherein R¹ᵃ is selected cyclobutyl, cyclopentyl, cyclohexyl, cyclohexenyl, tetrahydropyran, dihydropyran, tetrahydrofuran, oxetane, azetidine, pyrrolidine, piperidine, piperazine, morpholine, tetrahydrothiopyran (thiacyclohexane), and tetrahydrothiofuran (thiacyclopentane), each of which is optionally substituted with one or two groups independently selected from Oxo, D, halo, CN, hydroxy, C1-C4 alkoxy, C1-C4 alkyl, C1-C4 haloalkyl, C1-C4 hydroxyalkyl, C1-C4 haloalkoxy, C3-C8 cycloalkyl, —COOR²³, —SO₂R²⁴, —N(R²⁵ᵃR²⁵ᵇ), —N(R²⁵ᵃ)C(O)R²⁴, —N(R²⁵ᵃ)SO₂R²⁴, —N(R²⁵ᵃ)COOR²⁴, —CON(R²⁵ᵃR²⁵ᵇ) and —SO₂N(R²⁵ᵃR²⁵ᵇ), wherein each R²³, R²⁵ᵃ and R²⁵ᵇ are independently selected from H and C1-C4 alkyl; R²⁴ is C1-C4 alkyl.

Embodiment 7. The compound of any of embodiments 1-6 or a pharmaceutically acceptable salt thereof, wherein R² is phenyl and is optionally substituted with up to three groups independently selected from halo, D, CN, C1-C4 alkoxy, C1-C4 alkyl, C1-C4 haloalkyl, C1-C4 haloalkoxy, C3-C6 cycloalkyl, —SR²⁶, —SO₂R²⁶, —N(R²⁷ᵃR²⁷ᵇ), —N(R²⁷ᵃ)C(O)R²⁶ and —SO₂N(R²⁷ᵃR²⁷ᵇ), wherein each R²⁷ᵃ and R²⁷ᵇ are independently selected from H, C1-C4 alkyl and C1-C4 haloalkyl; R²⁶ is C1-C4 alkyl.

Embodiment 8. The compound of any of embodiments 1-7 or a pharmaceutically acceptable salt thereof, wherein R² is thiophene, thiazole, pyridine, pyrimidine, pyrazine or pyridazine, and is optionally substituted with up to three groups independently selected from D, halo, CN, C1-C4 alkoxy, C1-C4 alkyl, C1-C4 haloalkyl, C1-C4 haloalkoxy, —SO₂R²⁸, —N(R²⁹ᵃR²⁹ᵇ), —N(R²⁹ᵃ)C(O)R²⁸ and —SO₂N(R²⁹ᵃR²⁹ᵇ), wherein each R²⁹ᵃ and R²⁹ᵇ are independently selected from H, C1-C4 alkyl and C1-C4 haloalkyl; R²⁸ is C1-C4 alkyl.

Embodiment 9. The compound of embodiments 1-8 or a pharmaceutically acceptable salt thereof, wherein R³ is H, L¹ and L² are bond; and R⁴ is methyl or ethyl, and is optionally substituted with fluoro, amino, hydroxy, methylamino, ethylamino, dimethylamino, —OP(O)(OH)₂, methoxy or ethoxy.

Embodiment 10. The compound of embodiments 1-8 or a pharmaceutically acceptable salt thereof, wherein L¹ and L² are bond; R³ and R⁴ are H or D.

Embodiment 11. The compound of embodiments 1-8 or a pharmaceutically acceptable salt thereof, wherein L¹ is —C(O)NH—.

Embodiment 12. The compound of embodiment 1, which is of the Formula IA:

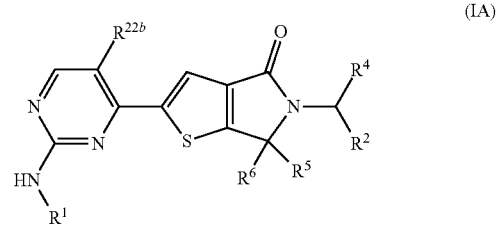

(IA)

wherein R¹ is phenyl, pyridine, pyrimidine, triazine, pyrazole, imidazole, isoxazole, isothiazole, oxazole, oxadiazole, triazole or thiazole, which can be substituted with up to two groups independently selected from D, F, Cl, Br, CN, Me, Et, Pr, i-Pr, cyclopropyl, butyl, isobutyl, sec-butyl, t-butyl, $CH_2F$, $CHF_2$, $CF_3$, MeO, EtO, i-PrO, PrO, BuO, t-BuO, s-BuO, i-BuO, $OCF_3$, —O(cyclopropyl), —$(CH_2)_2OH$, —$(CH_2)_2OMe$, —$(CH_2)C(OH)CH_2OH$, —$(CH_2)_2NHSO_2NH_2$, —$C(OH)(CH_3)_3$, —$O(CH_2)_2OH$, —$O(CH_2)_2OMe$, —$O(CH_2)C(OH)CH_2OH$ and —$O(CH_2)_2NHSO_2NH_2$, or R¹ is a non-aromatic cycloalkyl or heterocyclic group such as cyclopentyl, cyclohexyl, tetrahydropyranyl (e.g., 4-tetrahydropyranyl), 3-oxetanyl, 3- or 4-piperidinyl, 4- or 3-piperidin-2-onyl, 3- or 4-thiacyclopentane, 3-thiacyclohexane, 3-tetrahydrofuran, and the like, wherein a ring sulfur can be oxidized to sulfoxide or sulfone oxidation state, and each of these rings may be substituted with 1-3 groups independently selected from D, F, Cl, CN, amino, NHMe, $NMe_2$, Me, Et, i-Pr, cyclopropyl, $NHSO_2Me$, NHCOMe, Oxo, OH, OMe, —$CH_2OH$, and $CF_3$. The 1,4-disubstituted cyclohexyl can have either a cis or trans relative stereochemistry between the groups attached at positions 1 and 4, for example, a trans relative orientation between these groups;

wherein R² is phenyl, pyridine or thienyl, optionally substituted with 1-2 groups independently selected from D, amino, halo, $CF_3$, CN, C1-C4 alkyl, C1-C4 alkoxy, C1-C4 haloalkyl, C1-C4 haloalkoxy, —$COOR^{30}$, —$SO_2R^{31}$, —$N(R^{32a}R^{32b})$, —$N(R^{32a})C(O)R^{31}$, —$SO_2N(R^{32a}R^{32b})$ and —$N(R^{32a})SO_2R^{31}$, wherein each $R^{30}$, $R^{32a}$ and $R^{32b}$ are independently selected from H and C1-C4 alkyl; $R^{31}$ is C1-C4 alkyl; R⁴ is selected from H, D and —$CH_2R^*$, wherein R* is selected from H, —OH, F, —$NH_2$, —NHMe, —$NMe_2$, —$OP(O)(OH)_2$ and —OMe;

R⁵ and R⁶ are independently selected from H and an optionally substituted group selected from C1-C4 alkyl; wherein the optional substituents for R⁵ and R⁶ are 1-3 substituents independently selected from D, halo, —OH, C1-C4 alkoxy, C1-C4 haloalkoxy; wherein R⁵ and R⁶ can optionally cyclize to form a C3-C6 cycloalkyl ring or a 4-6 membered heterocyclic ring containing 1-2 heteroatoms selected from N, O, and S;

wherein $R^{22b}$ is selected from H, halo, and C1-C3 alkyl; or a pharmaceutically acceptable salt thereof.

Embodiment 13. The compound of embodiment 1, which is of the Formula IB:

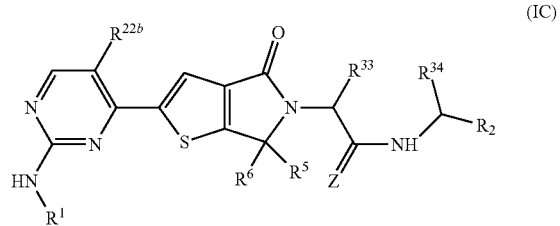

(IB)

wherein R¹, R², R⁵, R⁶ and $R^{22b}$ are as defined in embodiment 12.

Embodiment 14. The compound of embodiment 1, which is of the Formula IC:

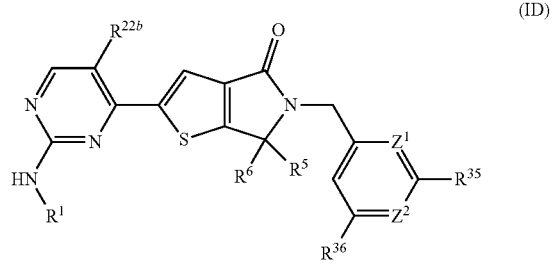

(IC)

wherein $R^{33}$ is selected from H, D and —$CH_2R^#$, wherein $R^#$ is selected from H and C1-C4 alkyl;

Embodiment 15. The compound of embodiment 1, which is of the Formula ID:

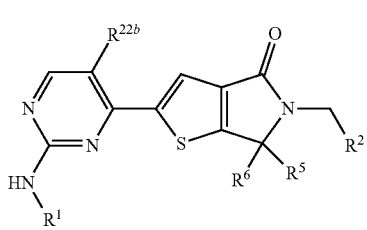

(ID)

wherein $R^{35}$ and $R^{36}$ are independently selected from H, F, CN, —$CF_3$, OMe, $OCF_3$, SMe and an optional substituted group selected from C1-C4 alkyl, C3-C6 cycloalkyl and C1-C4 alkoxyl; wherein the optional substituents are 1-3 substituents independently selected halogen;

wherein $Z^1$ and $Z^2$ are independently selected from CH and N;

wherein R¹, R⁵, R⁶ and $R^{22b}$ are as defined in embodiment 12.

Embodiment 16. The compound of any one of embodiments 12-15, or a pharmaceutically acceptable salt thereof, wherein R¹ is selected from:

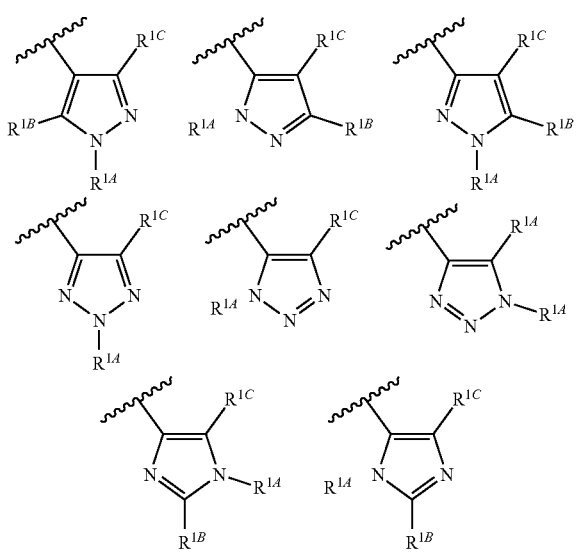

-continued

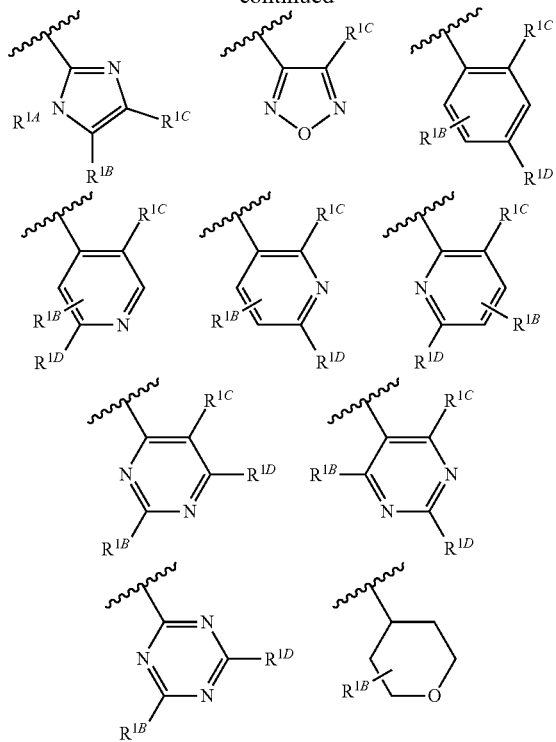

wherein each $R^{1A}$ is independently selected from H, Me, Et, propyl, isopropyl, cyclopropyl, butyl, t-butyl, sec-butyl, isobutyl, $CH_2F$, $CF_2H$ and $CF_3$; wherein $R^{1B}$, $R^{1C}$ and $R^{1D}$ are independently selected from H, Me, Et, propyl, isopropyl, cyclopropyl, butyl, t-butyl, sec-butyl, isobutyl, $CH_2F$, $CF_2H$, $CF_3$, MeO, EtO, PrO, i-PrO, c-PrO, BuO, t-BuO, s-BuO, i-BuO, $OCF_3$, c-PrO, $Me_3(OH)C—$, CN, Cl and F.

Embodiment 17. The compound of embodiment 1, which is selected from the following compounds and pharmaceutically acceptable salts thereof:
6,6-dimethyl-2-(2-(1-methyl-1H-pyrazol-5-ylamino)pyrimidin-4-yl)-5-((2-(trifluoromethyl)pyridin-4-yl)methyl)-5,6-dihydro-4H-thieno[2,3-c]pyrrol-4-one,
5-(3-chlorobenzyl)-6,6-dimethyl-2-(2-(1-methyl-1H-pyrazol-5-ylamino)pyrimidin-4-yl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-((6-(trifluoromethyl)pyridin-2-yl)methyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-((6-(trifluoromethyl)pyridin-3-yl)methyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-((4-(trifluoromethyl)thiazol-2-yl)methyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-((2-(trifluoromethyl)pyrimidin-4-yl)methyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-((3-(trifluoromethyl)isoxazol-5-yl)methyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-(2-(2-(trifluoromethyl)pyridin-4-yl)ethyl)-5,6-dihydro-4H-thieno[2,3-c]pyrrol-4-one,
6,6-dimethyl-2-(2-(1-methyl-1H-pyrazol-5-ylamino)pyrimidin-4-yl)-5-(1-(2-(trifluoromethyl)pyridin-4-yl)ethyl)-5,6-dihydro-4H-thieno[2,3-c]pyrrol-4-one,
(R)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one,
(S)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one.
6,6-dimethyl-2-(2-(1-methyl-1H-pyrazol-5-ylamino)pyrimidin-4-yl)-5-(1-(4-(trifluoromethyl)thiazol-2-yl)ethyl)-5,6-dihydro-4H-thieno[2,3-c]pyrrol-4-one
(R)-6,6-dimethyl-2-(2-((1-methyl-1H-pyrazol-5-yl)amino)pyrimidin-4-yl)-5-(1-(4-(trifluoromethyl)thiazol-2-yl)ethyl)-5,6-dihydro-4H-thieno[2,3-c]pyrrol-4-one
(S)-6,6-dimethyl-2-(2-((1-methyl-1H-pyrazol-5-yl)amino)pyrimidin-4-yl)-5-(1-(4-(trifluoromethyl)thiazol-2-yl)ethyl)-5,6-dihydro-4H-thieno[2,3-c]pyrrol-4-one
(S)-5-(1-(3-chlorophenyl)-2-hydroxyethyl)-6,6-dimethyl-2-(2-((1-methyl-1H-pyrazol-5-yl)amino)pyrimidin-4-yl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-(1-(6-(trifluoromethyl)pyridin-2-yl)ethyl)-5,6-dihydro-4H-thieno[2,3-c]pyrrol-4-one,
6,6-dimethyl-2-(2-((1-methyl-1H-pyrazol-5-yl)amino)pyrimidin-4-yl)-5-(1-(2-(trifluoromethyl)pyrimidin-4-yl)ethyl)-5,6-dihydro-4H-thieno[2,3-c]pyrrol-4-one,
(S)—N-(1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetamide,
N—((S)-1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanamide,
2-(6,6-dimethyl-2-(2-((1-methyl-1H-pyrazol-5-yl)amino)pyrimidin-4-yl)-4-oxo-4H-thieno[2,3-c]pyrrol-5(6H)-yl)-N-((2-(trifluoromethyl)pyridin-4-yl)methyl)acetamide, and
(S)-5-(2-((1-(3-chlorophenyl)-2-hydroxyethyl)amino)ethyl)-6,6-dimethyl-2-(2-((1-methyl-1H-pyrazol-5-yl)amino)pyrimidin-4-yl)-5,6-dihydro-4H-thieno[2,3-c]pyrrol-4-one.

Embodiment 18. A pharmaceutical composition comprising a compound according to any one of embodiments 1-17 admixed with at least one pharmaceutically acceptable excipient.

Embodiment 19. The pharmaceutical composition of embodiment 18, further comprising a therapeutic co-agent.

Embodiment 20. The pharmaceutical composition of embodiment 19, wherein the therapeutic co-agent is selected from anticancer compounds, analgesics, and anti-inflammatory compounds.

Embodiment 21. A method to treat cancer, comprising administering to a subject in need of such treatment a therapeutically effective amount of a compound according to any of embodiments 1-17 or a pharmaceutical composition of any of embodiments 18-20.

Embodiment 22. The method of embodiment 21, wherein the cancer is selected from adenoma, bladder cancer, brain cancer, breast cancer, cervical cancer, colorectal cancer, colon cancer, epidermal carcinoma, follicular carcinoma, genitourinary cancers, glioblastoma, head and neck cancers, Hodgkin's disease, non-Hodgkin's lymphoma, hepatoma, head and neck cancers, kidney cancer, lung cancers such as small cell or non-small cell lung cancer, leukemias such as AML or CML, multiple myeloma, lymphoid disorders, skin cancers including melanoma, neuroblastoma, ovarian cancer, pancreatic cancer, prostate cancer, rectal cancer, sarcoma, testicular cancer, and thyroid cancer.

Embodiment 23. A compound according to any one of embodiments 1-17 for use as a medicament.

Embodiment 24. Use of a compound according to any one of embodiments 1 to 17 or a pharmaceutically acceptable salt thereof in the manufacture of a medicament for the treatment of cancer; or use of a compound according to any one of embodiments 1 to 17 or a pharmaceutically acceptable salt thereof in medicine, especially for treatment of a cancer such as those named in embodiment 22.

Embodiment 25. A method to treat an inflammatory disease in a patient comprising administering to a subject in need of such treatment a therapeutically effective amount of a compound according to any of embodiments 1-17 or a pharmaceutical composition of any of embodiments 18-20, and/or a pharmaceutically acceptable salt thereof disclosed herein and a pharmaceutically acceptable carrier, wherein the inflammatory disease is selected from rheumatoid arthritis, psoriasis, or eczema.

In some embodiments of the compounds of Formula I and other embodiments described above, $X^1$ is, for example, N and $X^2$ is $CR^{22b}$, wherein $R^{22b}$ is H, halo, or C1-C4 alkyl. In one embodiment, $R^{22b}$ is H or $CH_3$.

In some embodiments of the compounds of Formula I and other embodiments described above, $L^1$ and $L^2$ are, for example, a bond; or L is —C(O)NH— and $L^2$ is —CH($CH_2R^{34}$)—, wherein $R^{34}$ is selected from H, D and —$CH_2R^*$, wherein $R^*$ is selected from H, —OH, F, —$NH_2$, —NHMe, —$NMe_2$, —OP(O)(OH)$_2$ and —OMe;

In some embodiments of the compounds of Formula I and other embodiments described above, $R^5$ and $R^s$ are independently H, $CH_3$, or methoxymethyl; $R^5$ and $R^6$ are, for example, both methyl, or H and methoxymethyl, respectively.

In certain of the foregoing embodiments, wherein at least one of $R^3$ and $R^4$ is hydrogen, or at least one of $R^{21a}$ and $R^{21b}$ is hydrogen (e.g., forming a group of formula —CHR*— as described herein), containing chiral centers; in certain of these embodiments, it has this stereochemistry:

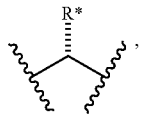

for example, R* is —$CH_3$, —$CH_2OH$, —$CH_2NH_2$, —$CH_2NHMe$, —$CH_2NMe_2$, —$CH_2F$, —$CH_2OMe$, —CH(OH)Me, —$CH_2OP(O)(H)_2$ or —CH(OH)$CH_2OH$.

In some embodiments, the compound of Formula I (such as Formula IA, IB, IC and ID), having the chiral configuration shown in excess over its enantiomer, so the compound is optically active. For example, such compounds of the disclosure are substantially free of the opposite enantiomer, i.e., at least 95% of the compound has the chirality shown above.

In some embodiments of the foregoing compounds, $R^2$ is aryl or heteroaryl, optionally substituted as described below, and commonly $R^2$ is an optionally substituted group selected from phenyl, thienyl, thiazolyl, pyridinyl, pyridazinyl, pyrazinyl, and pyrimidinyl. Substituted phenyl and pyridinyl are, for example, for $R^2$.

$R^2$ is often substituted with at least one group selected from those described for the embodiments described above. In some embodiments, $R^2$ is phenyl, 3-thienyl, 2-thiazolyl, 2-pyridinyl, 3-pyridinyl, or 4-pyridinyl that is unsubstituted or is substituted with 1-2 groups independently selected from halo (F, Cl, Br or I), methyl, methoxy, —SMe, methylsulfonyl, cyano, and cyclopropyl. In some embodiments, $R^2$ is phenyl and is substituted in at least one position at meta position relative to $L^2$ that is attached with F, Cl, Br, I, SMe, $CH_2F$, $CHF_2$, $CF_3$, or methylsulfonyl.

In some embodiments, the —$C(R^3R^4)$-$L^1$-$L^2$-$R^2$ portion of the structure in Formula I has the following formula:

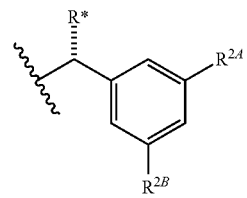

wherein R* is H, $CH_3$, $CH_2OH$, $CH_2NH_2$, $CH_2NHMe$, $CH_2NMe_2$, $CH_2OMe$, $CFH_2$, $CF_2H$, $CF_3$, or $CH_2OP(O)(OH)_2$; $R^{2A}$ and $R^{2B}$ are independently selected from H, F, Cl, Br, I, CN, $SO_2Me$, Me, OMe, $CFH_2$, $CF_2H$, $CF_3$, and SMe.

In these embodiments, at least one of $R^{2A}$ and $R^{2B}$ is typically other than H, and, for example, at least one of $R^{2A}$ and $R^{2B}$ is halo, such as F, Cl, Br, I or $CF_3$.

In some embodiments, the —$C(R^3R^4)$-$L^1$-$L^2$-$R^2$ portion of the structure in Formula I has the following formula:

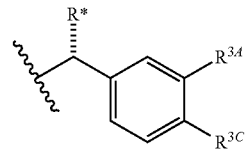

wherein R* is H, $CH_3$, $CH_2OH$, $CH_2NH_2$, $CH_2NHMe$, $CH_2NMe_2$, $CH_2OMe$, $CFH_2$, $CF_2H$, $CF_3$, or $CH_2OP(O)(OH)_2$; $R^{3A}$ and $R^{3C}$ are independently selected from H, F, Cl, Br, I, CN, $SO_2Me$, Me, OMe, $CH_2F$, $CF_2H$, $CF_3$, and SMe.

In these embodiments, at least one of $R^{3A}$ and $R^{3C}$ is typically other than H, and, for example, at least one of $R^{3A}$ and $R^{3C}$ is halo, such as F, Cl, Br, I, or $CF_3$.

In some embodiments, the —$C(R^3R^4)$-$L^1$-$L^2$-$R^2$ portion of the structure in Formula I has the following formula:

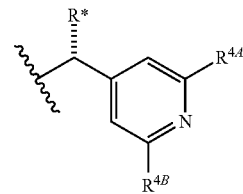

wherein R* is H, $CH_3$, $CH_2OH$, $CH_2NH_2$, $CH_2NHMe$, $CH_2NMe_2$, $CH_2OMe$, $CFH_2$, $CF_2H$, $CF_3$, or $CH_2OP(O)(OH)_2$; $R^{4A}$ and $R^{4B}$ are independently selected from H, F, Cl, Br, I, CN, —$SO_2Me$, Me, OMe, $OCF_3$, $CFH_2$, $CF_2H$, $CF_3$, and SMe In these embodiments, at least one of $R^{4A}$ and $R^{4B}$ is typically other than H, and, for example, at least one of $R^{4A}$ and $R^{4B}$ is $CF_3$.

In some embodiments, the —C(R³R⁴)-L¹-L²-R² portion of the structure in Formula I has the following formula:

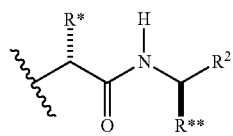

wherein R* is H, CH₃, CH₂F, CHF₂ or CF₃; R** is H, CH₃, CH₂OH, CH₂NH₂, CH₂NHMe, CH₂NMe₂, CH₂OMe, CFH₂, CF₂H, CF₃, or CH₂OP(O)(OH)₂; R² is as defined in previous embodiments.

Also disclosed herein is a pharmaceutical composition comprising a compound of Formula I (such as Formula IA, IB, IC and ID), and/or a pharmaceutically acceptable salt thereof, and a pharmaceutically acceptable carrier.

Further disclosed herein is a method of inhibiting the activity of ERK comprising contacting the protein Erk with an effective amount of a compound of Formula I (such as Formula IA, IB, IC and ID) and/or a pharmaceutically acceptable salt thereof disclosed herein.

Further disclosed herein is a method of treating a disease treatable by inhibition of ERK in a patient, comprising administering to the patient in recognized need of such treatment, an effective amount of a compound of Formula I (such as Formula IA, IB, IC and ID) and/or a pharmaceutically acceptable salt thereof disclosed herein.

Further disclosed herein is a method of treating a disease treatable by inhibition of Erk in a patient, comprising administering to the patient in recognized need of such treatment, an effective amount of a pharmaceutical composition comprising a compound of Formula I (such as Formula IA, IB, IC and ID) and/or a pharmaceutically acceptable salt thereof disclosed herein and a pharmaceutically acceptable carrier.

Further disclosed herein is a method of treating a cancer in a patient, comprising administering to the patient in recognized need of such treatment, an effective amount of a pharmaceutical composition comprising a compound of Formula I (such as Formula IA, IB, IC and ID) and/or a pharmaceutically acceptable salt thereof disclosed herein and a pharmaceutically acceptable carrier. In some embodiments, the cancer is colon cancer, gastric cancer, leukemia, lymphoma, melanoma, or pancreatic cancer.

Further disclosed herein is a method of treating an inflammatory disease in a patient, comprising administering to the patient in recognized need of such treatment, an effective amount of a pharmaceutical composition comprising a compound of Formula I (such as Formula IA, IB, IC and ID) and/or a pharmaceutically acceptable salt thereof disclosed herein and a pharmaceutically acceptable carrier. In some embodiments, the inflammatory disease is rheumatoid arthritis, psoriasis, or eczema.

Further disclosed herein is a use of a compound of Formula I (such as Formula IA, IB, IC and ID) and/or a pharmaceutically acceptable salt thereof in preparation of a medication for treating a disease responsive to inhibition of Erk, such as a cancer or an inflammatory disease. In some embodiments, the cancer is colon cancer, gastric cancer, leukemia, lymphoma, melanoma, or pancreatic cancer. In some embodiments, the inflammatory disease is rheumatoid arthritis, psoriasis, or eczema.

The pharmaceutical composition comprising a compound of Formula I (such as Formula IA, IB, IC and ID) and/or a pharmaceutically acceptable salt thereof, and a pharmaceutically acceptable carrier, can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The compound of Formula I (such as Formula IA, IB, IC and ID) and/or a pharmaceutically acceptable salt thereof can be administered orally in solid dosage forms, such as capsules, tablets, troches, dragées, granules and powders, or in liquid dosage forms, such as elixirs, syrups, emulsions, dispersions, and suspensions. The compound of Formula I (such as Formula IA, IB, IC and ID) and/or a pharmaceutically acceptable salt thereof can also be administered parenterally, in sterile liquid dosage forms, such as dispersions, suspensions or solutions. Other dosages forms that can also be used to administer the compound of Formula I (such as Formula IA, IB, IC and ID) and/or a pharmaceutically acceptable salt thereof include ointment, cream, drops, transdermal patch or powder for topical administration, an ophthalmic solution or suspension formation, i.e., eye drops, for ocular administration, an aerosol spray or powder composition for inhalation or intranasal administration, or a cream, ointment, spray or suppository for rectal or vaginal administration.

Gelatin capsules containing the compound of Formula I (such as Formula IA, IB, IC and ID) and/or a pharmaceutically acceptable salt thereof and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound disclosed herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the pharmaceutical composition (and in some embodiments, capable of stabilizing the active ingredients)

and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are disclosed in *Remington's Pharmaceutical Sciences*, A. Osol, a standard reference text in the art.

The compound of Formula I (such as Formula IA, IB, IC and ID) and/or a pharmaceutically acceptable salt thereof can be examined for efficacy in treating cancer by in vivo assays. For example, the compound of Formula I (such as Formula IA, IB, IC and ID) and/or a pharmaceutically acceptable salt thereof can be administered to an animal (e.g., a mouse model) having cancer and its therapeutic effects can be accessed. Positive results in one or more of such tests are sufficient to increase the scientific storehouse of knowledge and hence sufficient to demonstrate practical utility of the compounds and/or salts tested. Based on the results, an appropriate dosage range and administration route for animals, such as humans, can also be determined.

For administration by inhalation, the compound of Formula I (such as Formula IA, IB, IC and ID) and/or a pharmaceutically acceptable salt thereof may be conveniently delivered in the form of an aerosol spray presentation from pressurized packs or nebulisers. The compound of Formula I (such as Formula IA, IB, IC and ID) and/or a pharmaceutically acceptable salt thereof may also be delivered as powders, which may be formulated and the powder composition may be inhaled with the aid of an insufflation powder inhaler device. One exemplary delivery system for inhalation can be a metered dose inhalation (MDI) aerosol, which may be formulated as a suspension or solution of a compound of Formula I (such as Formula IA, IB, IC and ID) and/or a pharmaceutically acceptable salt thereof in at least one suitable propellant, selected, for example, from fluorocarbons and hydrocarbons.

For ocular administration, an ophthalmic preparation may be formulated with an appropriate weight percentage of a solution or suspension of the compound of Formula I (such as Formula IA, IB, IC and ID) and/or a pharmaceutically acceptable salt thereof in an appropriate ophthalmic vehicle, such that the compound of Formula I (such as Formula IA, IB, IC and ID) and/or a pharmaceutically acceptable salt thereof is maintained in contact with the ocular surface for a sufficient time period to allow the compound to penetrate the corneal and internal regions of the eye.

Useful pharmaceutical dosage-forms for administration of the compound of Formula I (such as Formula IA, IB, IC and ID) and/or a pharmaceutically acceptable salt thereof include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, the compound of Formula I (such as Formula IA, IB, IC and ID) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a capsule.

In some embodiments, a large number of unit capsules can be prepared by filling standard two-piece hard gelatin capsules each with, for example, 100 milligrams of the compound of Formula I (such as Formula IA, IB, IC and ID) and/or a pharmaceutically acceptable salt thereof in powder, 150 milligrams of lactose, 50 milligrams of cellulose, and 6 milligrams magnesium stearate.

In some embodiments, a mixture of the compound of Formula I (such as Formula IA, IB, IC and ID) and/or a pharmaceutically acceptable salt thereof and a digestible oil such as soybean oil, cottonseed oil or olive oil can be prepared and injected by means of a positive displacement pump into gelatin to form soft gelatin capsules containing 75 or 100 milligrams of the active ingredient. The capsules are washed and dried.

In some embodiments, the compound of Formula I (such as Formula IA, IB, IC and ID) and/or a pharmaceutically acceptable salt thereof can be present in an amount of 1, 5, 10, 15, 20, 25, 50, 75, 80, 85, 90, 95, 100, 125, 150, 200, 250, 300, 400 and 500 mg in a tablet.

In some embodiments, a large number of tablets can be prepared by conventional procedures so that the dosage unit comprises, for example, 100 milligrams of the compound of Formula I (such as Formula IA, IB, IC and ID) and/or a pharmaceutically acceptable salt thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may, for example, be applied to increase palatability or delay absorption.

In some embodiments, a parenteral composition suitable for administration by injection can be prepared by stirring 1.5% by weight of a compound of Formula I (such as Formula IA, IB, IC and ID) and/or a pharmaceutically acceptable salt thereof in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound of Formula I (such as Formula IA, IB, IC and ID) and/or a pharmaceutically acceptable salt thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound of Formula I (such as Formula IA, IB, IC and ID) and/or a pharmaceutically acceptable salt thereof are administered stepwise or in conjunction with at least one other therapeutic agent. When drugs are administered in physical combination, the dosage form and administration route should be selected depending on the compatibility of the combined drugs. Thus, the term "co-administration" is understood to include the administration of at least two agents concomitantly or sequentially, or alternatively as a fixed dose combination of the at least two active components.

The compound of Formula I (such as Formula IA, IB, IC and ID) and/or a pharmaceutically acceptable salt thereof can be administered as the sole active ingredient or in combination with at least one second active ingredient, selected, for example, from other active ingredients known to be useful for treating the target disease, such as cancers including, for example, colon cancer, gastric cancer, leukemia, lymphoma, melanoma, and pancreate cancer in a patient.

As used herein, the term "optical isomer" or "stereoisomer" refers to any of the various stereo isomeric configurations which may exist for a given compound of the present disclosure and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. The present disclosure includes enantiomers, diastereomers or racemates of the compounds. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog lR-SJ system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present disclosure includes all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present disclosure are capable of forming acid and/or base salts by virtue of the presence of amino and/or carboxyl groups or groups similar thereto. As used herein, the terms "salt" or "salts" refers to an acid addition or base addition salt of a compound of the disclosure. "Salts" include in particular "pharmaceutical acceptable salts". The term "pharmaceutically acceptable salts" refers to salts that retain the biological effectiveness and properties of the compounds of this disclosure and, which typically are not biologically or otherwise undesirable.

Pharmaceutically acceptable acid addition salts can be formed with inorganic acids and organic acids, e.g., acetate, adipate, aluminum, ascorbate, aspartate, benzoate, besylate, bromide/hydrobromide, bicarbonate/carbonate, bisulfate/sulfate, camphorsulfonate, caproate, chloride/hydrochloride, chloroprocaine, chlortheophyllonate, citrate, edetate, calcium edetate, ethandisulfonate, ethylsulfonate, ethylene diamine, fumarate, galactarate (mucate), gluceptate, gluconate, glucuronate, glutamate, glycolate, hexyl resorcinate, hippurate, hydroiodide/iodide, hydroxynaphthoate (xinofoate), isethionate, lactate, lactobionate, laurylsulfate, lithium, malate, maleate, malonate, mandelate, mesylate, methylsulphate, naphthoate, napsylate, nicotinate, nitrate, octadecanoate, oleate, oxalate, palmitate, pamoate, pantothenate, phosphate/hydrogen phosphate/dihydrogen phosphate, polygalacturonate, procaine, propionate, salicylate, sebacate, stearate, subacetate, succinate, sulfate, sulfosalicylate, tannate, tartrate, bitartrate, tosylate, triphenylacetate, and trifluoroacetate salts. Lists of additional suitable salts can be found, e.g., in REMINGTON'S PHARMACEUTICAL SCIENCES, 20th ed., Mack Publishing Company, Easton, Pa., (1985); and in HANDBOOK OF PHARMACEUTICAL SALTS: PROPERTIES, SELECTION, AND USE, by Stahl and Wermuth (Wiley-VCH, Weinheim, Germany, 2002). Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present disclosure can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is intended to represent unlabeled forms (i.e., compounds wherein all atoms are present at natural isotopic abundances and not isotopically enriched) as well as isotopically enriched or labeled forms of the compounds. Isotopically enriched or labeled compounds have structures depicted by the formulas given herein except that at least one atom of the compound is replaced by an atom of the same element but having an atomic mass or mass number different from the atomic mass or the atomic mass distribution that occurs naturally. Examples of isotopes that can be incorporated into enriched or labeled compounds of the disclosure include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The present disclosure includes various isotopically labeled compounds as defined herein, for example those in which radioactive isotopes, such as $^3$H and $^{14}$C, or those in which non-radioactive isotopes, such as $^2$H and $^{13}$C, are present at levels significantly above the natural abundance for these isotopes. These isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of Formula I can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula I if it is incorporated at substantially above the level of natural isotopic abundance. The present disclosure includes isotopically enriched versions of the compounds, e.g., deuterated versions as well as non-deuterated versions. Deuterated versions may be deuterated at a single site, or at multiple sites.

The degree of incorporation of such an isotope in an isotopically-enriched compound, particularly deuterium, may be defined by the isotopic enrichment factor. The term "isotopic enrichment factor" as used herein means the ratio between the isotopic abundance of a specified isotope in a sample, and the natural abundance of the isotope in a non-enriched sample. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the present disclosure include those wherein the solvent of crystallization may be isotopically substituted, e.g. D$_2$O, d$^6$-acetone, d$^6$-DMSO, as well as solvates with non-enriched solvents.

Compounds of the invention, e.g., compounds of Formula I (such as Formula IA, IB, IC and ID), that contain groups capable of acting as donors and/or acceptors for hydrogen bonds, may be capable of forming cocrystals with suitable co-crystal formers. These co-crystals may be prepared from compounds of Formula I (such as Formula IA, IB, IC and ID), by known co-crystal forming procedures. Such procedures include grinding, heating, co-subliming, co-melting, or contacting in solution compounds of Formula I (such as Formula IA, IB, IC and ID), with the co-crystal former under crystallization conditions and isolating cocrystals thereby formed. Suitable co-crystal formers include those described in WO2004078163. Hence the present disclosure further provides co-crystals comprising a compound of Formula I (such as Formula IA, IB, IC and ID).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, REMINGTON'S PHARMACEUTICAL SCIENCES, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present disclosure refers to an amount of the compound of the present disclosure that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "therapeutically effective amount" refers to the amount of the compound of the present disclosure that, when administered to a subject, is effective to (1) at least partially alleviate, inhibit, prevent and/or ameliorate a condition, or a disorder or a disease (i) mediated by a kinase such as ERK1/2 or (ii) associated with activity of a kinase such as ERK1/2, or (iii) characterized by activity (normal or abnormal) of ERK1/2; or (2) reduce or inhibit the activity of ERK1/2 or (3) reduce or inhibit the expression of ERK1/2.

In another non-limiting embodiment, the term "a therapeutically effective amount" refers to the amount of the compound of the present disclosure that, when administered to a cell, or a tissue, or a non-cellular biological material, or a medium, is effective to at least partially reduce or inhibit the activity of ERK1/2, or at least partially reduce or inhibit the expression of ERK1/2.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, activity, effect, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to delaying the development or progression of the disease or disorder.

As used herein, a subject is "in need of" a treatment if such subject would be expected to benefit biologically, medically or in quality of life from such treatment.

As used herein, the term "a" "an" "the" and similar terms used in the context of the present disclosure (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often, for example, to use one enantiomer to the substantial exclusion of the other enantiomer. Substituents at atoms with carbon-carbon double bonds may, where possible, be present in cis-(Z)- or trans-(E)-form, and both are included in the present disclosure unless otherwise indicated.

Accordingly, as used herein a compound of the present disclosure can be in the form of one of the possible isomers, rotamers, atropisomers, or tautomers or as a mixture thereof, for example, as substantially pure geometric (cis or trans) isomers, diastereomers, optical isomers (antipodes), racemates or mixtures thereof. "Substantially pure" or "substantially free of other isomers" as used herein means the product contains less than 5%, and, such as, less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present disclosure, including their salts, can also be obtained in the form of their hydrates, or include other solvents used for their crystallization. The compounds of the present disclosure may inherently or by design form solvates with pharmaceutically acceptable solvents (including water); therefore, it is intended that the present disclosure embraces both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of Formula I can be made by a general synthetic method as illustrated in Scheme 1. The 5,6-dihydro-4H-thieno[2,3-c]pyrrol-4-one (1) can be N-alkylated with compound 2 by reacting with a suitable base such as sodium hydride or potassium hexamethyldisilazide in a suitable solvent such as THF or DMF to form compound 3. Coupling of compound 3 and compound 4 can be carried out using palladium catalyzed chemistry, converting compound 3 to boronic acid or pinacol ester then subsequent reaction with compound 4 under well-known palladium-assisted conditions to form compounds of formula 5. Alternatively, $Z^1$ in compound 4 can be converted to bornic acid or pinacol ester, which then reacts with compound 3 to form compound 5 under similar palladium catalyzed chemistry. Reaction of compound 5 with the amine 6 under palladium-assisted conditions to form compounds of formula 7, which are compounds of Formula I.

Scheme 1

-continued

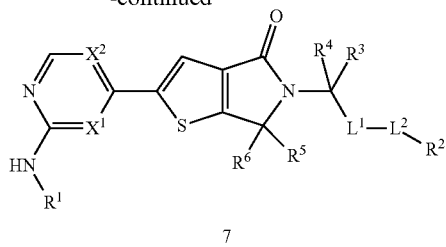

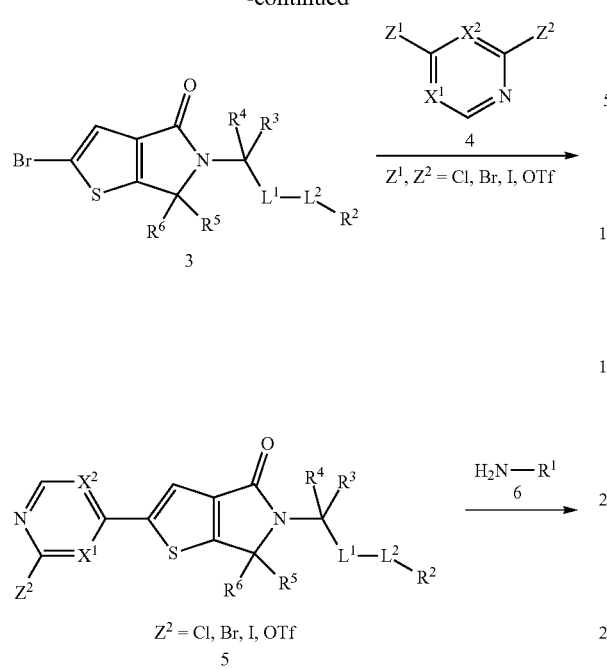

The intermediate 5,6-dihydro-4H-thieno[2,3-c]pyrrol-4-one 1 can be made by many known methods to the skilled person. Scheme 2 illustrates two general synthetic methods. The readily available dibromothiophenecarboxylic acid (8) is reacted with alkyl metal such as n-butyllithium or iso-propylmagnesium chloride under low temperature and the resulting dianion is reacted with compound 9 to form the the alcohol which is then cyclized to lactone 10 catalyzed by a suitable catalyst such as sulfuric acid or p-toluenesulfonic acid in a suitable solvent such as toluene at elevated temperature. Conversion of 10 to lactam 1 can be achieved using ammonia at high temperature. Alternatively, thiophene-3-carboxylic acid 11 can be converted to compound 13 using the same methods as described previously. Compound 13 is converted to bromide 1 by reacting with a suitable bromination reagent such as NBS or Br$_2$ in a suitable solvent such as acetonitrile or acetic acid.

Scheme 2

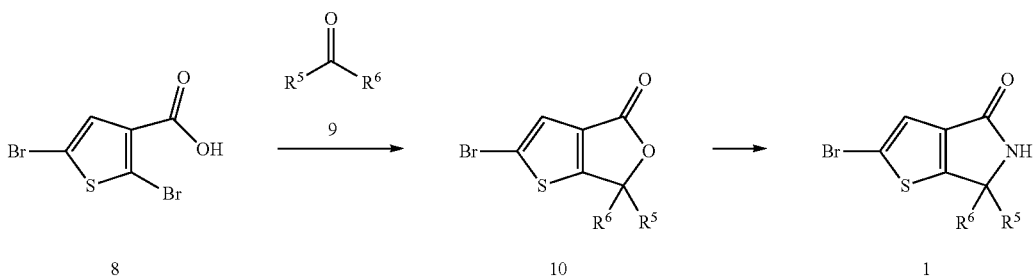

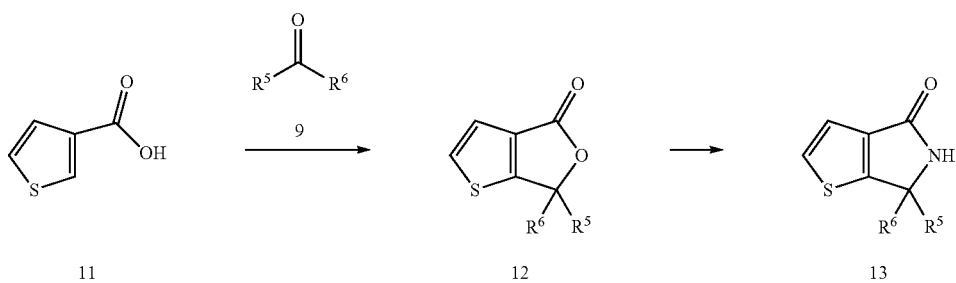

Schemes 3 and 4 in some instances illustrates preparation of compounds of Formula IA, but methods for preparing suitable compounds of Formula I where $R^1$, $R^2$, $R^3$, $R^4$, $R^5$, $R^6$, $X^1$, $X^2$, $L^1$ and $L^2$ are other options encompassed by Formula I are readily apparent to the skilled person in view of the many known methods for making the requisite intermediates 1, 2 and 4, so the method is equally applicable to preparation of compounds with other embodiments of $R^1$, $R^2$, $R^3$, $R^4$, $R^5$, $R^6$, $X^1$, $X^2$, $L^1$ and $L^2$.

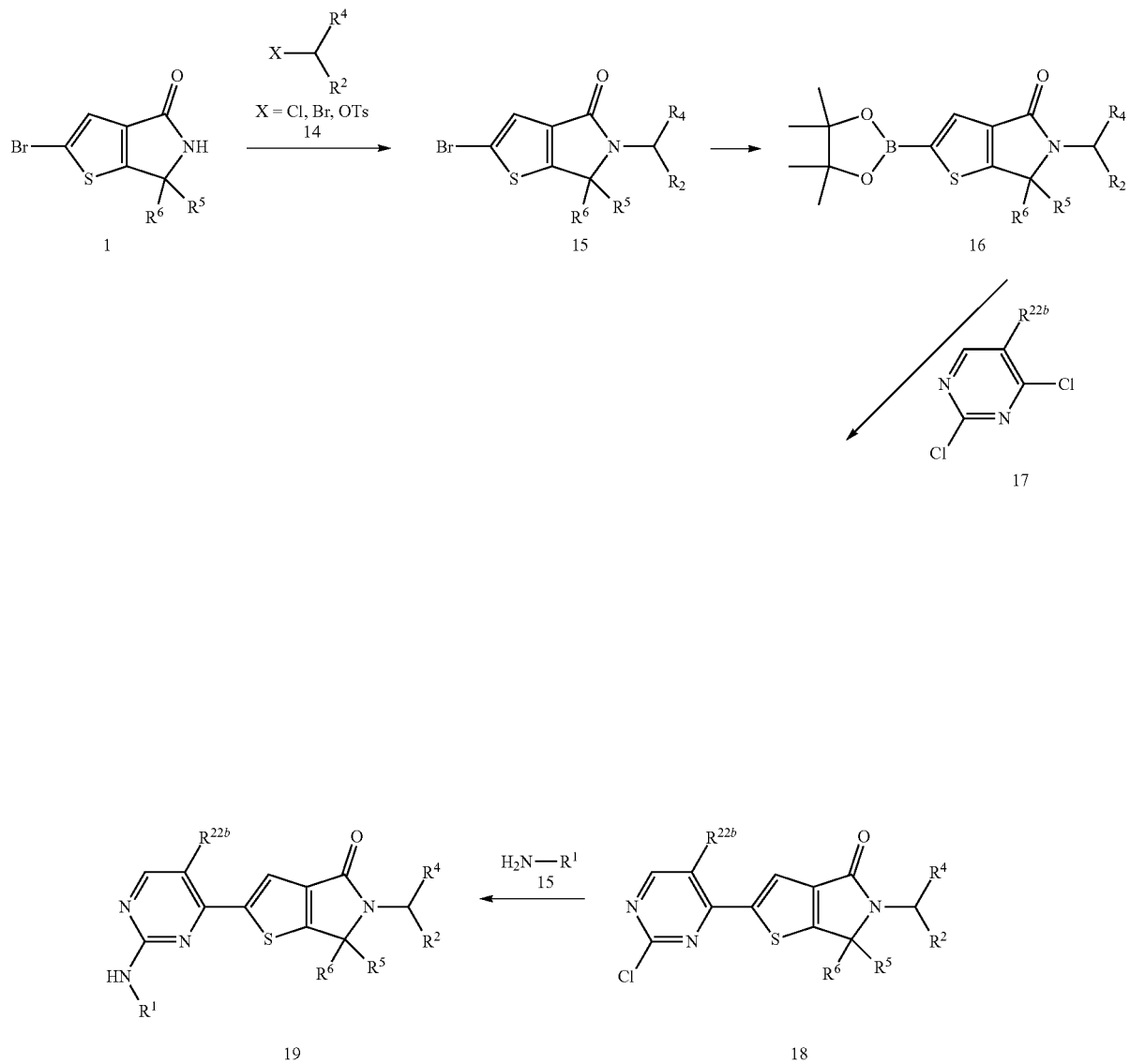

Scheme 3

Scheme 3 illustrates one synthetic method to compounds of Formula IA. Intermediate 1 is N-alkylated with compound 14 by reacting with a suitable base such as sodium hydride or potassium hexamethyldisilazide in a suitable solvent such as THF or DMF to form compound 15. Conversion of compound 15 to boronic acid pinacol ester 16 is carried out using palladium catalyzed chemistry under well-known palladium-assisted conditions. Coupling of boronic acid pinacol ester 16 and compound 17 can be carried out using palladium catalyzed chemistry to provide compound 18. Reaction of compound 18 with the amine 15 under palladium-assisted conditions to form compounds of formula 19, which are compounds of Formula IA.

Scheme 4

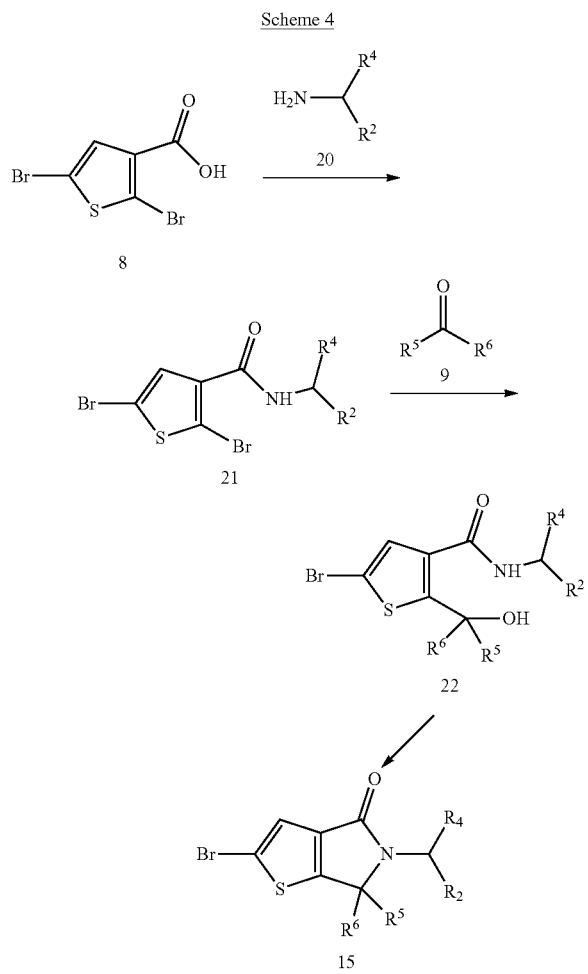

Scheme 4 illustrates an alternative synthetic method to Intermediate 15. Dibromothiophenecarboxylic acid 8 is converted to amide 21 with the side chain containing groups of $R^2$ and $R^4$ already installed by using many well-known amide preparation methods such as reacting with thionyl chloride and subsequent reaction of the intermediate acid chloride with amine 20. Compound 20 reacts with alkyl metal such as n-butyllithium under low temperature and the resulting dianion is reacted with compound 9 to form the alcohol 22, which is then cyclized to compound 15 catalyzed by a suitable catalyst such as sulfuric acid or p-toluenesulfonic acid in a suitable solvent such as toluene at elevated temperature.

EXAMPLES

The following examples illustrate certain embodiments of the disclosure and how to make and use them. They are not intended to limit the scope of the invention.

In the following examples, the abbreviations below are used:

9-BBN 9-Borabicyclo[3.3.1]nonane
Boc tert-Butyloxycarbonyl
$B_2pin_2$ Bis(pinacolato)diboron
BPO Dibenzoyl peroxide
dba dibenzylideneacetone
DAST Diethylaminosulfur trifluoride
DCE 1,2-Dichloroethene
DCM Dichloromethane
DIPEA di-isopropylethylamine
DMAP 4-Dimethylaminopyridine
DMF Dimethylformamide
DMSO Dimethylsulfoxide
EDCI 1-Ethyl-3-(3-dimethylaminopropyl)carbodiimide
EDTA Ethylenediaminetetraacetic acid
EtOAc ethyl acetate
HATU 1-[Bis(dimethylamino)methylene]-1H-1,2,3-triazolo[4,5-b]pyridinium 3-oxid hexafluorophosphate
HOBt Hydroxybenzotriazole
KHNDS Potassium hexamethyldisilazide
LDA Lithium diisopropylamide
LG Leaving group
MeOH Methanol
MsCl Methanesulfonyl chloride
NaHMDS Sodium hexamethyldisilazide
NBS N-Bromosuccinimide
NMP N-Methyl-2-pyrrolidone
Pd(dppf)Cl$_2$ [1,1'Bis(diphenylphosphino)ferrocene]dichloropalladium (II)
PE Petroleum ether
PG Protecting group
PPTS Pyridinium p-toluenesulfonate
Prep-TLC Preparative Thin layer chromatography
PTSA p-toluenesulfonic acid
TBAF Tetra-n-butylammonium fluoride
TBAI Tetra-n-butylammonium iodide
TEA Triethylamine
TES Triethylsilyl
TFA trifluoracetic acid
TfOH Triflic acid
THF tetrahydrofuran
THP tetrahydropyran tetrahydrofuran
TLC Thin layer chromatography
TsCl 4-Toluenesulfonyl chloride
Xantphos 4,5-Bis(diphenylphosphino)-9,9-dimethylxanthene Intermediate 1

(2-(trifluoromethyl)pyridin-4-yl)methyl Methanesulfonate

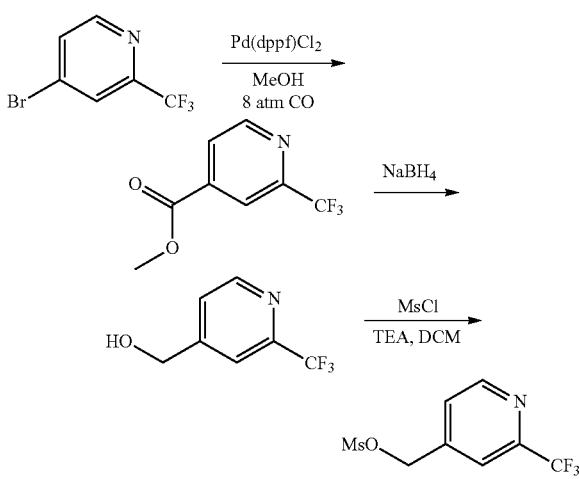

Step 1. Methyl 2-(trifluoromethyl)isonicotinate

To a solution of 4-bromo-2-(trifluoromethyl)pyridine (20 g, 88.5 mmol) in MeOH (150 mL) in an 250-mL autoclave was added Pd(dppf)Cl$_2$·CH$_2$Cl$_2$ (1.44 g, 1.77 mmol), followed by TEA (17.9 g, 177.0 mmol). The autoclave was charged with CO to 8 atm and stirred at 80° C. for 18 h, maintaining the pressure of CO at 8 atm. The mixture was cooled to rt and MeOH was removed in vacuo. The residue was dissolved in EtOAc (500 mL), washed with water (200 mL×2) and brine (200 mL), dried over anhydrous Na$_2$SO$_4$, and concentrated. The residue was dissolved in PE/EtOAc (10/1, 50 mL) and filtered through a short pad of silica gel to remove the catalyst. The filtrate was concentrated to give the title compound (15.4 g, yield: 84%).

Step 2. (2-(trifluoromethyl)pyridin-4-yl)methanol

To an ice-water cooled solution of the product of Step 1 above (15.4 g, 75.0 mmol) in MeOH (100 mL) was added NaBH$_4$ (7.1 g, 187.7 mmol) portionwise while maintaining the internal temperature below 30° C. After the addition was complete, the mixture was stirred at rt for 2 h before quenching with acetone (20 mL). The reaction mixture was concentrated and the residue was dissolved in EtOAc (200 mL), washed with water (50 mL×3) and brine (50 mL), dried over anhydrous Na$_2$SO$_4$, and concentrated to give the title compound (11.8 g, yield: 88%).

Step 3. (2-(trifluoromethyl)pyridin-4-yl)methyl Methanesulfonate

To an ice-water cooled solution of the product of Step 2 above (50 mg, 0.282 mmol) and TEA (43 mg, 0.423 mmol) in DCM (3 mL) was added MsCl (38 mg, 0.339 mmol). The mixture was stirred at rt for 1 h. The reaction mixture was diluted with DCM (20 ML), which was washed with saturated aqueous Na$_2$CO$_3$ (10 mL) and brine (20 ML), dried over anhydrous Na$_2$SO$_4$ and concentrated to afford the title compound (69 mg, yield: 96%). MS (ESI) m/z=256.1 [M+H]$^+$.

Intermediate 2

2-bromo-6,6-dimethyl-5,6-dihydro-4H-thieno[2,3-c]pyrrol-4-one

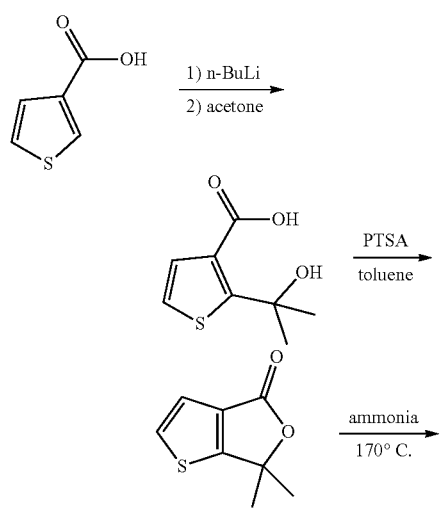

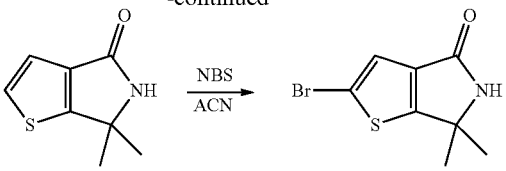

Step 1. 2-(2-hydroxypropan-2-yl)thiophene-3-carboxylic Acid

To a solution of thiophene-3-carboxylic acid (75 g, 585 mmol) in THF (1500 mL) to −70° C. in a dry-ice/acetone bath under nitrogen, was added n-butyllithium (2.5 N in hexane, 562 mL, 1404 mmol) slowly while maintaining the internal temperature below −55° C. Solid formation could be observed during the addition. After the addition was complete, the reaction was stirred at −70° C. for 30 min before adding acetone (44.2 g, 761 mmol) dropwise while maintaining the temperature below −60° C. After the addition was complete, the reaction mixture was stirred for 10 min. at −70° C. and 2 h in an ice-water bath. The reaction mixture was quenched with hydrochloric acid (4 N, 800 mL) at 0° C. and stirred for 1 h. The organic phase was separated, dried over anhydrous Na$_2$SO$_4$, and concentrated in vacuo to give the crude product (~85 g, liquid and semi-solid), which was used in the next step without any further purification.

Step 2. 6,6-dimethylthieno[2,3-c]furan-4(6H)-one

To the crude product of Step 1 above (85 g, liquid and semi-solid) in toluene (1000 mL) was added PTSA monohydrate (30 g, 160 mmol) and water (75 mL). The mixture was refluxed at 100° C. for 18 h. The reaction mixture was cooled to rt, diluted with EtOAc (1000 mL), washed with aqueous NaOH (2 N, 1000 mL) and brine (1000 mL). The organic layer was dried over anhydrous Na$_2$SO$_4$, and concentrated in vacuo to give the crude title compound (48 g, yield: 49% in 2 steps).

Step 3. 6,6-dimethyl-5,6-dihydro-4H-thieno[2,3-c]pyrrol-4-one

A 3-L autoclave was charged with a solution of the product of Step 2 above (110 g, 654 mmol) and concentrated ammonium hydroxide (28%, 1000 mL). The mixture was heated slowly to 170° C. and stirred at this temperature for 18 h. The reaction mixture was cooled to rt, and extracted with DCM/isopropanol (10/1, 500 mL×3). The combined organic layers were dried over anhydrous Na$_2$SO$_4$ and concentrated to give the crude product, which was triturated with PE/EtOAc (10/1, 1100 mL) and the solid was filtered and dried in vacuo to give the title compound (77 g, yield: 70%).

Step 4. 2-bromo-6,6-dimethyl-5,6-dihydro-4H-thieno[2,3-c]pyrrol-4-one

To a suspension of the product of Step 3 above (60 g, 358.8 mmol) and saturated aqueous ammonia chloride (36 mL) in acetonitrile (720 mL) was added portionwise NBS (70.25 g, 394.7 mmol). After stirring at rt for 18 h, the mixture was concentrated in vacuo. The residue was dissolved in EtOAc (2 L), which was washed with aqueous saturated sodium bisulfite (500 mL×4) and brine (1000 mL), dried over anhydrous Na$_2$SO$_4$, and concentrated in vacuo. The residue was triturated with PE/EtOAc (1/2, 200 mL) and the solid was filtered and dried in vacuo to give the title compound (83.6 g, yield: 81%). MS (ESI) m/z=246.1 & 248.2 [M+H]$^+$.

Intermediate 3

4-(1-bromoethyl)-2-(trifluoromethyl)pyridine

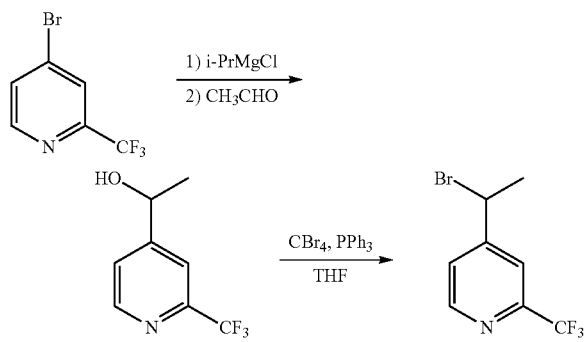

Step 1. 1-(2-(trifluoromethyl)pyridin-4-yl)ethanol

To a solution of 4-bromo-2-(trifluoromethyl)pyridine (190 g, 840.7 mmol) in THF (1.3 L) cooled to 0° C. was added isopropylmagnesium chloride (2N in THF, 462 mL, 924 mmol) at such a rate to keep internal temperature <5° C. After the addition was complete, the mixture was stirred at ~10° C. for 0.5 h and re-cooled to 0° C. and acetaldehyde (55.48 g, 1.26 mol) was added while keeping internal temperature <10° C. After the addition was complete, the mixture was stirred at ~10° C. for 30 min before quenching with saturated aqueous NH$_4$Cl. The resultant solution was concentrated to remove most of the THF and the aqueous solution was extracted with EtOAc (1.0 L×3). The combined organic layers were washed with water (500 mL×3) and brine (500 mL×2), dried over anhydrous Na$_2$SO$_4$, and concentrated in vacuo to give the title compound (150 mg, yield: 93%), which was used in the next step without any further purification.

Step 2.
4-(1-bromoethyl)-2-(trifluoromethyl)pyridine

To a solution of the product of Step 1 above (200 g, 1.05 mol) and CBr$_4$ (524 g, 1.57 mol) in THF (2 L) was added PPh$_3$ (412 g, 1.57 mol) at rt in several portions. After the addition was complete, the mixture was stirred at rt for 1 h. Additional CBr$_4$ (87 g, 0.26 mol) and PPh$_3$ (68.5 g, 0.26 mol) were added sequentially. The reaction mixture was stirred at rt for 1 h and filtered and the filtrate was concentrated in vacuo. The residue was purified by flash column chromatography on silica gel (PE/EtOAc=2/1) to give the title compound (173 g, yield: 65%). MS (ESI) m/z=254.1 & 256.0 [M+H]$^+$.

Intermediate 4

(R)-2-((tert-butyldimethylsilyl)oxy)-1-(3-chlorophenyl)ethyl Methanesulfonate

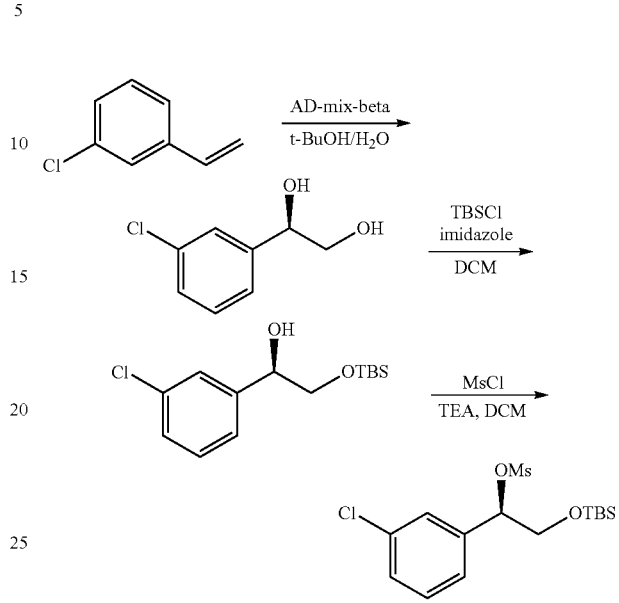

Step 1. (R)-1-(3-chlorophenyl)ethane-1,2-diol

To a solution of AD-mix-beta in t-BuOH/H$_2$O (60 mL/60 mL) was added 1-chloro-3-vinylbenzene (4.8 g, 35 mmol) dropwise at rt. The mixture was stirred at rt overnight before quenching with saturated aqueous NaHSO$_3$ (100 mL). The reaction mixture was diluted with water (200 mL), and extracted with EtOAc (200 mL×3). The combined organic layers were washed with water (200 mL) and brine (200 mL), dried over anhydrous Na$_2$SO$_4$, and concentrated. The residue was purified by flash column chromatography on silica gel (PE/EtOAc=4/1) to give the title compound (5.2 g, yield: 86%).

Step 2. (R)-2-((tert-butyldimethylsilyl)oxy)-1-(3-chlorophenyl)ethanol

To a solution of the product of Step 1 above (5.2 g, 30 mmol) in DCM (50 mL) cooled to 0° C. was added imidazole (5.1 g, 75 mmol) and TBSCl (4.5 g, 30 mmol) sequentially. The mixture was stirred over ice-water bath for 1 h, and was diluted with DCM (200 mL), washed with water (50 mL×2) and brine (50 mL), dried over anhydrous Na$_2$SO$_4$, and concentrated. The residue was purified by flash column chromatography on silica gel (PE/EtOAc=10/1) to give the title compound (7.3 g, yield: 85%).

Step 3. (R)-2-((tert-butyldimethylsilyl)oxy)-1-(3-chlorophenyl)ethyl Methanesulfonate To a solution of the product of Step 2 above (200 mg, 0.548 mmol) in DCM (10 mL) cooled over an ice-water bath was added TEA (83 mg, 0.822 mmol), followed by dropwise addition of MsCl (75 mg, 0.658 mmol). The mixture was stirred at rt for 1 h, and was diluted with DCM (100 mL), washed by saturated aqueous Na$_2$CO$_3$ (30 mL), water (30 mL) and brine (30 mL), dried over anhydrous Na$_2$SO$_4$, and concentrated to give the crude title compound (300 mg), which was used in the next step without any further purification. MS (ESI) m/z=365.2 & 367.1 [M+H]$^+$.

Intermediate 5

2-(2-(trifluoromethyl)pyridin-4-yl)ethyl 4-methylbenzenesulfonate

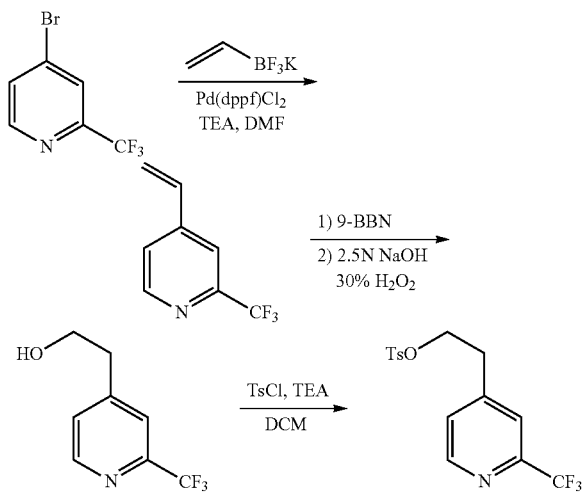

Step 1. 2-(trifluoromethyl)-4-vinylpyridine

To a solution of potassium vinyltrifluoroborate (3.6 g, 27 mmol) and Pd(dppf)Cl$_2$·CH$_2$Cl$_2$ (0.9 g, 1.1 mmol) in DMF (50 mL) was added 4-bromo-2-(trifluoromethyl)pyridine (5.0 g, 22 mmol), and followed by TEA (3.3 g, 33 mmol). The mixture was stirred at 105° C. for 18 h under N$_2$. After cooling to rt, the reaction mixture was diluted with EtOAc (100 mL), washed with water (50 mL×5), dried over anhydrous Na$_2$SO$_4$, and concentrated. The residue was filtered through a short pad of silica gel (PE/EtOAc=10/1 to 2/1) and concentrated to give the title compound (2.5 g, yield: 65%).

Step 2. 2-(2-(trifluoromethyl)pyridin-4-yl)ethanol

To a solution of the product of Step 1 above (1.3 g, 7.5 mmol) in THF (10 mL) was added 9-BBN (0.5N in THF, 37.5 mL, 18.75 mmol) dropwise at 0° C. under N$_2$. After stirring at 60° C. for 2 h, the mixture was cooled to rt, to which NaOH (2.5 N, 15 mL, 37.5 mmol) was added, followed by slow addition of H$_2$O$_2$ (30%, 4.3 g). The resulting mixture was stirred at rt for 18 h. The mixture was filtered and the filtrate was extracted with EtOAc (100 mL), which was washed with water (30 mL), dried over anhydrous Na$_2$SO$_4$, and concentrated. The residue was purified by flash column chromatography on silica gel (PE/EtOAc=4/1 to 2/1) to give the title compound (800 mg, yield: 56%).

Step 3. 2-(2-(trifluoromethyl)pyridin-4-yl)ethyl 4-methylbenzenesulfonate

To a solution of the product of Step 2 above (650 mg, 3.42 mmol) in DCM (10 mL) was added TEA (691 mg, 6.84 mmol) and TsCl (978 mg, 5.13 mmol) sequentially at 0° C. The mixture was stirred at rt for 6 h, and was diluted with EtOAc (100 mL), washed with water (20 mL) and brine (20 mL), dried over anhydrous Na$_2$SO$_4$, and concentrated. The residue was purified by flash column chromatography on silica gel (PE/EtOAc=20/1 to 4/1) to give the title compound (940 mg, yield: 80%). MS (ESI) m/z=246.1 [M+H]$^+$ Intermediate 6

4-(1-bromoethyl)-2-(trifluoromethyl)pyrimidine

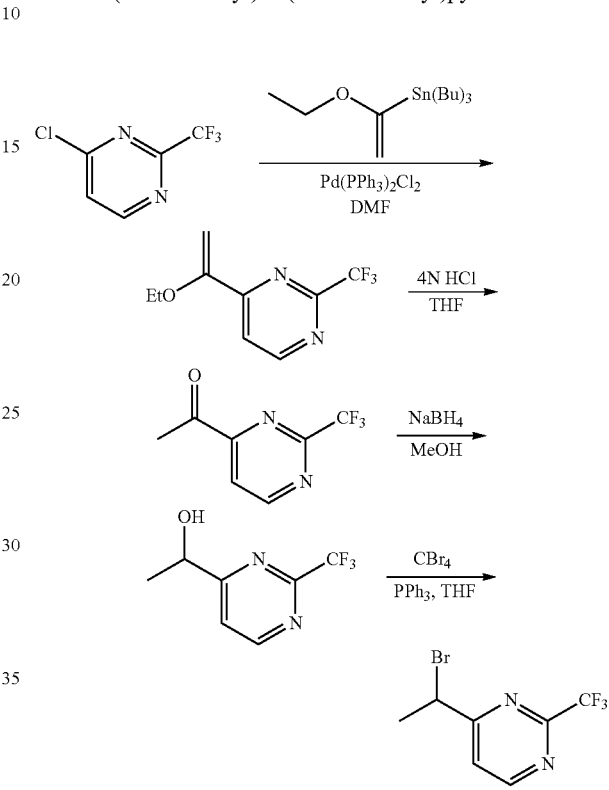

Step 1.
4-(1-ethoxyvinyl)-2-(trifluoromethyl)pyrimidine

To a solution of 4-chloro-2-(trifluoromethyl)pyrimidine (4.09 g, 22.43 mmol) and Pd(PPh$_3$)$_2$Cl$_2$ (315 mg, 0.449 mmol) in DMF (50 mL) was added tributyl(1-ethoxyvinyl)stannane (8.91 g, 24.7 mmol) at rt. After stirring at 85° C. for 18 h under N$_2$, the reaction mixture was cooled to rt, and then KF (16 g) and water (70 mL) were added. The mixture was stirred at rt for an additional 10 min before diluting with EtOAc (150 mL). The organic layer was separated, washed with water (100 mL×2) and brine (100 mL), dried over anhydrous Na$_2$SO$_4$, and concentrated. The residue was purified by flash column chromatography on silica gel (PE/EtOAc=15/1) to give the title compound (4.53 g, yield: 93%)

Step 2.
1-(2-(trifluoromethyl)pyrimidin-4-yl)ethanone

To a solution of the product of Step 1 above (4.53 g, 20.76 mmol) in THF (40 mL) was added aqueous 4N HCl (10.4 mL) at rt. After stirring at 30° C. for 18 h, the mixture was concentrated to remove THF. The residual aqueous solution was adjusted to pH=8~9 with saturated aqueous NaHCO$_3$, which was extracted with EtOAc (80 mL). The extract was washed with water (50 mL), dried over anhydrous Na$_2$SO$_4$, and concentrated to give the title compound (4.49 g, crude), which was used in the next step without any further purification.

Step 3. 1-(2-(trifluoromethyl)pyrimidin-4-yl)ethanol

To an ice-water cooled solution of the product of Step 2 above (3.99 g, 20.99 mmol) in MeOH (30 mL) was added NaBH$_4$ (953 mg, 26.19 mmol) portionwise to keep the internal temperature <30° C. The mixture was stirred at rt for 0.5 h, quenched with acetone (10 mL), diluted with EtOAc (80 mL), washed with water (40 mL×2) and brine (40 mL), dried over anhydrous Na$_2$SO$_4$, and concentrated to give the title compound (3.21 g, yield: 71%).

Step 4.
4-(1-bromoethyl)-2-(trifluoromethyl)pyrimidine

To an ice-water cooled solution of the product of Step 3 above (2.71 g, 14.1 mmol) and CBr$_4$ (7.02 g, 21.16 mmol) in THF (10 mL) was added slowly PPh$_3$ (5.6 g, 21.3 mmol). After stirring at 40° C. for 1.5 h, the reaction mixture was filtered. The filtrate was concentrated and the residue was purified by flash column chromatography on silica gel (PE/EtOAc=4/1) to give the title compound (2.76 g, yield: 77%). MS (ESI) m/z=255.1 & 257.1 [M+H]$^+$.

Intermediate 7

2-(1-bromoethyl)-6-(trifluoromethyl)pyridine

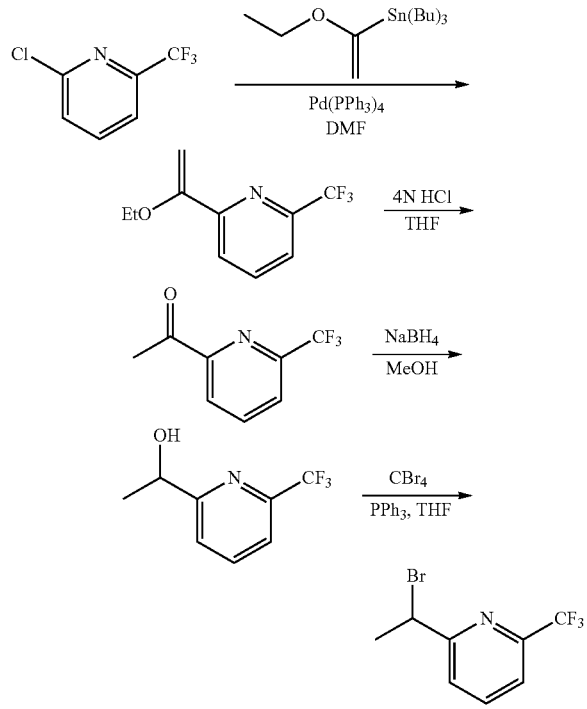

Intermediate 7 was synthesized according to the procedures described for Intermediate 6 starting from 2-bromo-6-(trifluoromethyl)pyridine.

Intermediate 8

2-(1-bromoethyl)-4-(trifluoromethyl)thiazole

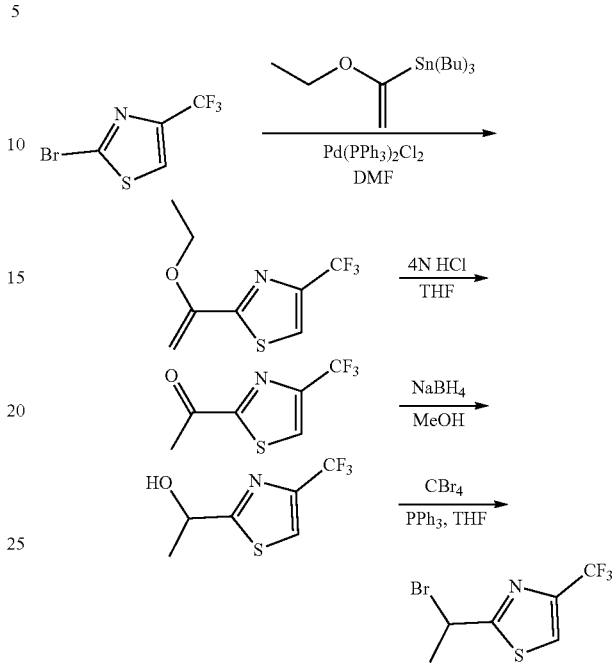

Step 1.
2-(1-ethoxyvinyl)-4-(trifluoromethyl)thiazole

To a solution of 2-bromo-4-(trifluoromethyl)thiazole (4.5 g, 19.4 mmol) and Pd(PPh$_3$)$_2$Cl$_2$ (272 mg, 0.39 mmol) in DMF (50 mL) was added tributyl(1-ethoxyvinyl)stannane (7.7 g, 21.3 mmol) at rt. The mixture was stirred at 85° C. for 4 h under N$_2$. After cooling to rt, KF (20 g) and water (70 mL) were added to the reaction mixture, which was stirred at rt for an additional 10 min. The mixture was taken up in EtOAc (150 mL), which was washed with water (80 mL×2) and brine (80 mL), dried over anhydrous Na$_2$SO$_4$, and concentrated. The residue was purified by flash column chromatography on silica gel (PE/EtOAc=10/1) to give the title compound (4.4 g, yield: 92%)

Step 2. 1-(4-(trifluoromethyl)thiazol-2-yl)ethanone

To a solution of the product of Step 1 above (3.9 g, 17.5 mmol) in THF (40 mL) was added aqueous 4N HCl (8.7 mL) at rt. After stirring at 30° C. for 4 h, the reaction mixture was concentrated to remove THF, the residual aqueous solution was adjusted to pH=8~9 with saturated aqueous NaHCO$_3$, and extracted with DCM (80 mL). The extract was washed with water (50 mL), dried over anhydrous Na$_2$SO$_4$, and concentrated to give the title compound (4.85 g, crude), which was used in the next step without any further purification.

Step 3. 1-(4-(trifluoromethyl)thiazol-2-yl)ethanol

To an ice-water cooled solution of the product of Step 2 above (4.35 g, 22.3 mmol) in MeOH (40 mL) was added NaBH$_4$ (1.01 g, 26.76 mmol) portionwise to keep the internal temperature <30° C. After stirring at rt for 0.5 h, the reaction mixture was quenched with acetone (2 mL), diluted with EtOAc (100 mL), washed with water (50 mL×2) and brine (50 mL), dried over anhydrous Na$_2$SO$_4$, and concentrated to give the title compound (3.5 g, yield: 80%).

Step 4. 2-(1-bromoethyl)-4-(trifluoromethyl)thiazole

To an ice-water cooled solution of the product of Step 3 above (3.5 g, 17.8 mmol) and CBr$_4$ (7.06 g, 21.30 mmol) in THF (40 mL) was added slow PPh3 (5.6 g, 21.3 mmol). After stirring at 40° C. for 1.5 h, the reaction mixture was filtered. The filtrate was concentrated and the residue was purified by flash column chromatography on silica gel (PE/EtOAc=20/1) to give the title compound (2.49 g, yield: 54%). MS (ESI) m/z=260.0 & 262.1 [M+H]$^+$ Intermediate 9

2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetic Acid

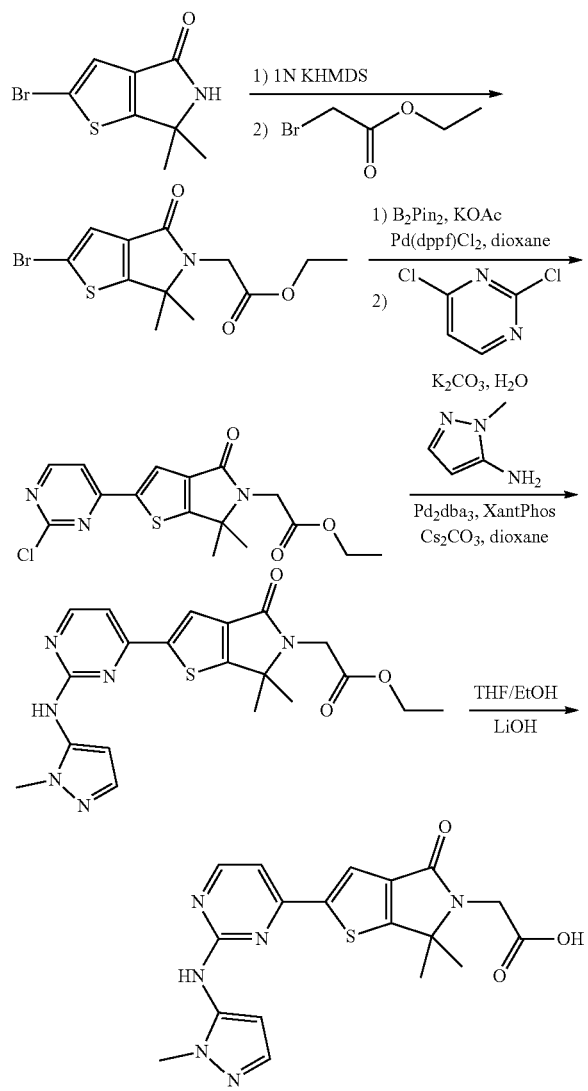

Step 1. ethyl 2-(2-bromo-6,6-dimethyl-4-oxo-4H-thieno[2,3-c]pyrrol-5(6H)-yl)acetate To a stirred solution of Intermediate 2 (2.0 g, 8.126 mmol) in THF (15 mL) was added KHMDS (1 N, 9.75 mL, 9.75 mmol) under N$_2$ at 0° C. The mixture was stirred at 0° C. for 1 h before adding ethyl 2-bromoacetate (1.63 g, 9.75 mmol). The reaction mixture was stirred at 70° C. for 18 h under N$_2$. After cooling to rt, the mixture was diluted with EtOAc (80 mL), which was washed with water (40 mL×2) and brine (40 mL), dried over anhydrous Na$_2$SO$_4$, and concentrated. The residue was purified by flash column chromatography on silica gel (PE/EtOAc=1/1) to give the title compound (2.2 g, yield: 81%).

Step 2. ethyl 2-(2-(2-chloropyrimidin-4-yl)-6,6-dimethyl-4-oxo-4H-thieno[2,3-c]pyrrol-5(6H)-yl)acetate To a solution of the product of Step 1 above (2.2 g, 6.62 mmol) in dioxane (10 mL) were added B$_2$pin$_2$ (1.76 g, 6.95 mmol), KOAc (1.30 g, 13.24 mmol) and Pd(dppf)Cl$_2$·CH$_2$Cl$_2$ (270 mg, 0.331 mmol) sequentially. The reaction mixture was stirred at 90° C. for 3 h under N$_2$. After cooling to rt, 2,4-dichloropyrimidine (986 mg, 6.62 mmol), K$_2$CO$_3$ (2.28 g, 16.55 mmol) and water (2 mL) were added sequentially and the reaction mixture was flushed with N$_2$ and stirred at 110° C. for 18 h. The resultant mixture was cooled to rt, diluted with DCM/MeOH (10/1, 100 mL), washed with water (60 mL×2) and brine (60 mL), dried over anhydrous Na$_2$SO$_4$, and concentrated. The residue was purified by flash column chromatography on silica gel (PE/EtOAc=3/1 to 10/1 then DCM/MeOH=100/1 to 50/1) to give the title compound (538 mg, yield: 22%)

Step 3. ethyl 2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetate To a solution of the product of Step 2 above (538 mg, 1.47 mmol) in dioxane (10 mL) was added 1-methyl-1H-pyrazol-5-amine (500 mg, 5.15 mmol), Cs$_2$CO$_3$ (958 mg, 2.94 mmol), Pd$_2$(dba)$_3$ (67 mg, 0.0735 mmol) and Xantphos (85 mg, 0.147 mmol) sequentially. The reaction mixture was stirred at 110° C. for 2 h under N$_2$. After cooling to rt, the mixture was diluted with DCM/methanol (10/1, 80 mL), washed with water (50 mL×2) and brine (50 mL), dried over anhydrous Na$_2$SO$_4$, and concentrated. The residue was purified by flash column chromatography on silica gel (DCM/MeOH=100/1 to 10/1) to give the title compound (444 mg, yield: 71%).

Step 4. 2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetic Acid To the product of Step 3 above (444 mg, 1.04 mmol) in THF/EtOH/H$_2$O (5 mL/5 mL/1 mL) was added LiOH·H$_2$O (131 mg, 3.12 mmol). After stirring at 50° C. for 1.5 h, the reaction mixture was cooled to rt and adjusted to PH=5~6 with aqueous HCl (4N). The mixture was diluted with DCM/i-PrOH (3/1, 60 mL) and water (30 mL). The organic layer was separated, dried over anhydrous Na$_2$SO$_4$, and concentrated to give the crude title compound (411 mg, yield: 99%), which was used in the next step without any further purification. MS (ESI) m/z=399.2 [M+H]$^+$

Intermediate 10

2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanoic Acid

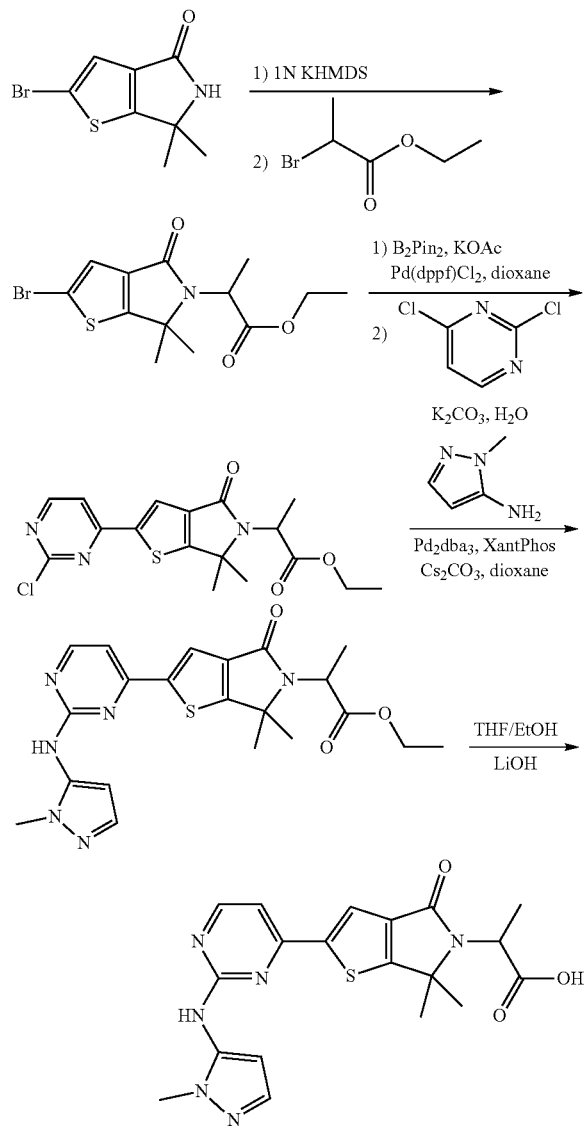

Step 1. ethyl 2-(2-bromo-6,6-dimethyl-4-oxo-4H-thieno[2,3-c]pyrrol-5(6H)-yl)propanoate To a stirred solution of Intermediate 2 (2.0 g, 8.126 mmol) in THF (15 mL) was added KHMDS (1 N, 9.75 mL, 9.75 mmol) under $N_2$ at 0° C. The mixture was stirred at 0° C. for 0.5 h before adding ethyl 2-bromopropanoate (1.77 g, 9.75 mmol). The reaction mixture was stirred at 70° C. for 18 h under $N_2$, cooled to rt, diluted with EtOAc (80 mL), washed with water (40 mL×2) and brine (40 mL), dried over anhydrous $Na_2SO_4$, and concentrated to give the title compound (2.91 g).

Step 2. ethyl 2-(2-(2-chloropyrimidin-4-yl)-6,6-dimethyl-4-oxo-4H-thieno[2,3-c]pyrrol-5(6H)-yl)propanoate To a solution of the product of Step 1 above (2.91 g, ~8.13 mmol) in dioxane (15 mL) were added $B_2pin_2$ (2.24 g, 8.83 mmol), KOAc (1.65 g, 16.8 mmol) and $Pd(dppf)Cl_2 \cdot CH_2Cl_2$ (343 mg, 0.42 mmol) sequentially. The reaction mixture was stirred at 90° C. for 2.5 h under $N_2$. After cooling to rt, 2,4-dichloropyrimidine (1.25 g, 8.4 mmol), $K_2CO_3$ (2.32 g, 16.8 mmol) and water (3 mL) were added sequentially and the reaction mixture was flushed with $N_2$ and stirred at 110° C. for 18 h. The resultant mixture was cooled to rt, diluted with DCM/MeOH (10/1, 150 mL), washed with water (60 mL×2) and brine (60 mL), dried over anhydrous $Na_2SO_4$, and concentrated. The residue was purified by flash column chromatography on silica gel (DCM/MeOH=100/1 to 80/1) to give the title compound (1.28 g, yield: 40%).

Step 3. ethyl 2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanoate To a solution of the product of Step 2 (1.28 g, 3.37 mmol) in dioxane (10 mL) were added 1-methyl-1H-pyrazol-5-amine (1.15 g, 11.8 mmol), $Cs_2CO_3$ (2.20 g, 6.74 mmol), $Pd_2(dba)_3$ (154 mg, 0.168 mmol) and Xantphos (194 mg, 0.337 mmol) sequentially. The reaction mixture was stirred at 110° C. for 2 h under $N_2$. After cooling to rt, the mixture was diluted with DCM/methanol (10/1, 100 mL), washed with water (50 mL×2) and brine (50 mL), dried over anhydrous $Na_2SO_4$, and concentrated. The residue was purified by flash column chromatography on silica gel (DCM/MeOH=100/1 to 50/1) to give the title compound (640 mg, yield: 43%).

Step 4. 2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanoic Acid To a solution of the product of Step 3 above (640 mg, 1.45 mmol) in THF/EtOH/$H_2O$ (8 mL/8 mL/1.5 mL) was added LiOH·$H_2O$ (183 mg, 4.36 mmol). The mixture was stirred at 50° C. for 1.5 h. After cooling to rt, the reaction mixture was adjusted to PH=5~6 with aqueous HCl (4N), and diluted with DCM/i-PrOH (3/1, 60 mL) and water (30 mL). The organic layer was separated, dried over anhydrous $Na_2SO_4$, and concentrated to give the crude title compound (550 mg, yield: 92%), which was used in the next step without any further purification. MS (ESI) m/z=413.1 $[M+H]^+$

Intermediate 11

2-(2-(2-((1-methyl-1H-pyrazol-5-yl)amino)pyrimidin-4-yl)-4-oxo-4H-thieno[2,3-c]pyrrol-5(6H)-yl) acetic Acid

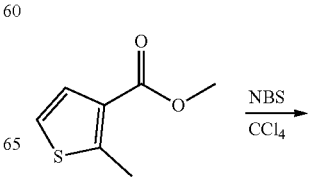

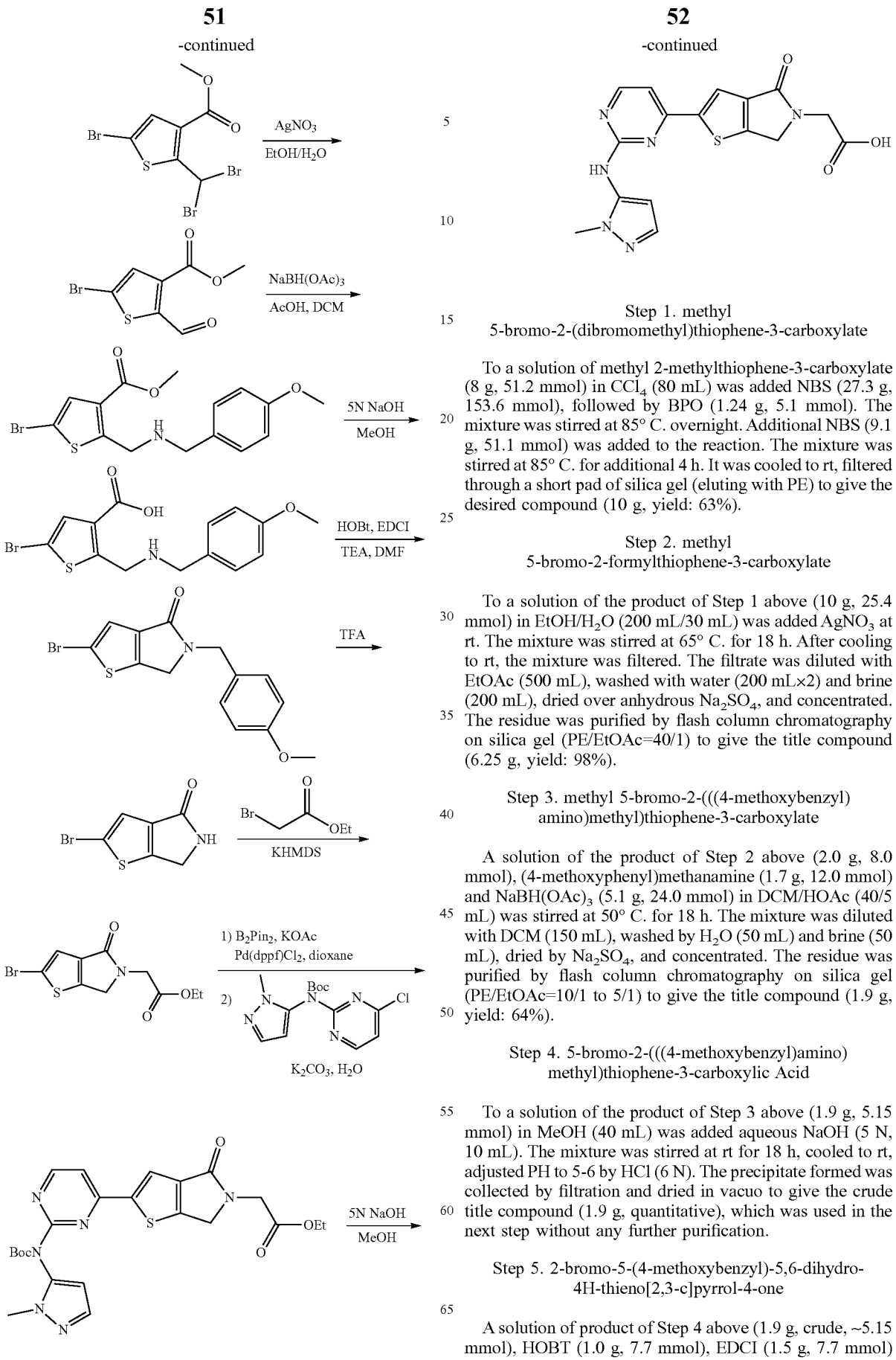

Step 1. methyl 5-bromo-2-(dibromomethyl)thiophene-3-carboxylate

To a solution of methyl 2-methylthiophene-3-carboxylate (8 g, 51.2 mmol) in CCl$_4$ (80 mL) was added NBS (27.3 g, 153.6 mmol), followed by BPO (1.24 g, 5.1 mmol). The mixture was stirred at 85° C. overnight. Additional NBS (9.1 g, 51.1 mmol) was added to the reaction. The mixture was stirred at 85° C. for additional 4 h. It was cooled to rt, filtered through a short pad of silica gel (eluting with PE) to give the desired compound (10 g, yield: 63%).

Step 2. methyl 5-bromo-2-formylthiophene-3-carboxylate

To a solution of the product of Step 1 above (10 g, 25.4 mmol) in EtOH/H$_2$O (200 mL/30 mL) was added AgNO$_3$ at rt. The mixture was stirred at 65° C. for 18 h. After cooling to rt, the mixture was filtered. The filtrate was diluted with EtOAc (500 mL), washed with water (200 mL×2) and brine (200 mL), dried over anhydrous Na$_2$SO$_4$, and concentrated. The residue was purified by flash column chromatography on silica gel (PE/EtOAc=40/1) to give the title compound (6.25 g, yield: 98%).

Step 3. methyl 5-bromo-2-(((4-methoxybenzyl)amino)methyl)thiophene-3-carboxylate A solution of the product of Step 2 above (2.0 g, 8.0 mmol), (4-methoxyphenyl)methanamine (1.7 g, 12.0 mmol) and NaBH(OAc)$_3$ (5.1 g, 24.0 mmol) in DCM/HOAc (40/5 mL) was stirred at 50° C. for 18 h. The mixture was diluted with DCM (150 mL), washed by H$_2$O (50 mL) and brine (50 mL), dried by Na$_2$SO$_4$, and concentrated. The residue was purified by flash column chromatography on silica gel (PE/EtOAc=10/1 to 5/1) to give the title compound (1.9 g, yield: 64%).

Step 4. 5-bromo-2-(((4-methoxybenzyl)amino)methyl)thiophene-3-carboxylic Acid To a solution of the product of Step 3 above (1.9 g, 5.15 mmol) in MeOH (40 mL) was added aqueous NaOH (5 N, 10 mL). The mixture was stirred at rt for 18 h, cooled to rt, adjusted PH to 5-6 by HCl (6 N). The precipitate formed was collected by filtration and dried in vacuo to give the crude title compound (1.9 g, quantitative), which was used in the next step without any further purification.

Step 5. 2-bromo-5-(4-methoxybenzyl)-5,6-dihydro-4H-thieno[2,3-c]pyrrol-4-one A solution of product of Step 4 above (1.9 g, crude, ~5.15 mmol), HOBT (1.0 g, 7.7 mmol), EDCI (1.5 g, 7.7 mmol)

and TEA (1.6 g, 15.5 mmol) in DMF (30 ML) was stirred at 50° C. for 3 h. The mixture was diluted with EtOAc (200 mL), washed with water (50×2 mL) and brine (50 mL), dried by Na$_2$SO$_4$, and concentrated. The residue was purified by flash column chromatography on silica gel (PE/EtOAc=6/1 to 3/1) to give the title compound (800 mg, yield: 46%).

Step 6. 2-bromo-5,6-dihydro-4H-thieno[2,3-c]pyrrol-4-one

A solution of the product of Step 5 above (750 mg, 2.23 mmol) in TFA (10 mL) was stirred at 75° C. for 3 h. The mixture after adding with ice-water (10 mL) and saturated aqueous Na$_2$CO$_3$ (50 mL) was extracted with DCM/MeOH (10/1, 50 mL×3). The combined organic layers were washed by brine (30 mL), dried over Na$_2$SO$_4$, and concentrated. The residue was purified by flash column chromatography on silica gel (PE/EA=2/1 to 1/1) to give the title compound (450 mg, yield: 93%).

Step 7. ethyl 2-(2-bromo-4-oxo-4H-thieno[2,3-c] pyrrol-5(6H)-yl)acetate

To an ice-water cooled solution of the product of Step 6 above (200 mg, 0.92 mmol) in THF (10 mL) was added NaH (60% in mineral oil, 45 mg, 1.1 mmol). The mixture was stirred at 0° C. for 0.5 h before adding ethyl 2-bromoacetate (185 mg, 1.11 mmol). The mixture was stirred at rt for 3 h, diluted with EtOAc (100 mL), washed by water (30 mL) and brine (30 mL), dried by Na$_2$SO$_4$, and concentrated. The residue was purified by flash column chromatography on silica gel (PE/EtOAc=2/1-1/1) to give the title compound (220 mg, yield: 79%).

Step 8. ethyl 2-(2-(2-((tert-butoxycarbonyl)(1-methyl-1H-pyrazol-5-yl)amino)pyrimidin-4-yl)-4-oxo-4H-thieno[2,3-c]pyrrol-5(6H)-yl)acetate A mixture of the product of Step 7 above (220 mg, 0.73 mmol), B$_2$pin$_2$ (194 mg, 0.76 mmol), Pd(dppf)Cl$_2$·CH$_2$Cl$_2$ (30 mg, 0.0365 mmol), and KOAc (143 mg, 1.46 mmol) in dioxane (5 mL) was stirred at 80° C. under N$_2$ for 2 h. After cooling to rt, Pd(dppf)Cl$_2$·CH$_2$Cl$_2$ (30 mg, 0.0365 mg), K$_2$CO$_3$ (202 mg, 1.46 mmol) and dioxane/H$_2$O (10 mL/2 mL) were added. The mixture was stirred at 100° C. overnight under N$_2$. After cooling to rt, it was diluted with EtOAc (100 mL), washed by water (30 mL×2) and brine (30 mL), dried over anhydrous Na$_2$SO$_4$, and concentrated. The residue was purified by prep-TLC (silica gel, DCM/MeOH=30/1) to give the title compound (80 mg, yield: 24%).

Step 9. 2-(2-(2-((1-methyl-1H-pyrazol-5-yl)amino) pyrimidin-4-yl)-4-oxo-4H-thieno[2,3-c]pyrrol-5 (6H)-yl)acetic acid To a solution of the product of Step 8 above (80 mg, 0.16 mmol) in MeOH (2 mL) was added aqueous NaOH (5N, 2 mL) at rt. The mixture was stirred at rt overnight and concentrated to remove MeOH. The residue was diluted with ice-water (5 ML), adjusted to PH=5~6 with 6N HCl (aq), and extracted with DCM/MeOH (50 mL). The extract was dried over anhydrous Na$_2$SO$_4$ and concentrated to give the title compound (30 mg, yield: 50%), which was used in the next step without any further purification. MS (ESI) m/z=371.0 [M+H]$^+$ Intermediate 12

(2-(trifluoromethyl)pyridin-4-yl)methanamine

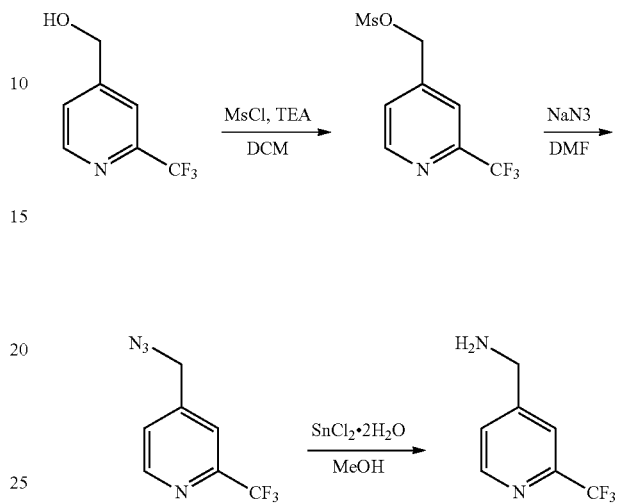

Step 1. (2-(trifluoromethyl)pyridin-4-yl)methyl Methanesulfonate

To an ice-water cooled solution of the product of Step 2 in Intermediate 1 (2.0 g, 11.3 mmol) in DCM (40 mL) was added TEA ((1.7 g, 16.96 mmol), followed by slow addition of MsCl (1.5 g, 13.56 mmol). The mixture was stirred 0° C. for 1 h, diluted with EtOAc (100 mL), washed with water (30 mL), saturated aqueous Na$_2$CO$_3$ (30 mL) and brine (30 mL), dried over anhydrous Na$_2$SO$_4$, and concentrated to give the crude title compound (3.0 g), which was used in the next step without any further purification.

Step 2. 4-(azidomethyl)-2-(trifluoromethyl)pyridine

To a solution of the product of Step 1 above (3.0 g, crude, ~11.3 mmol) in DMF (20 mL) was added NaN$_3$ (881 mg, 22.6 mmol). The mixture was stirred at rt overnight, diluted with EtOAc (200 mL), washed with water (20 mL×2) and brine (30 mL), dried over anhydrous Na$_2$SO$_4$, and concentrated to give the crude title compound (2.5 g), which was used in the next step without any further purification.

Step 3. (2-(trifluoromethyl)pyridin-4-yl)methanamine

To an ice-water cooled solution of the product of Step 2 above (2.5 g, crude, ~11.3 mmol) in MeOH (20 mL) was added SnCl$_2$·2H$_2$O (7.6 g, 33.9 mmol) slowly. The mixture was stirred at rt for 2 h, which was diluted with water (5 mL) and basified with K$_2$CO$_3$ to pH of 8-9. The solid was filtered off and the filtrate was dried over anhydrous Na$_2$SO$_4$ and concentrated in vacuo to give the crude title compound (695 mg, yield: 35%), which was used in the next step without any further purification. MS (ESI) m/z=377.1 [M+H]$^+$

Intermediate 13

2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetaldehyde

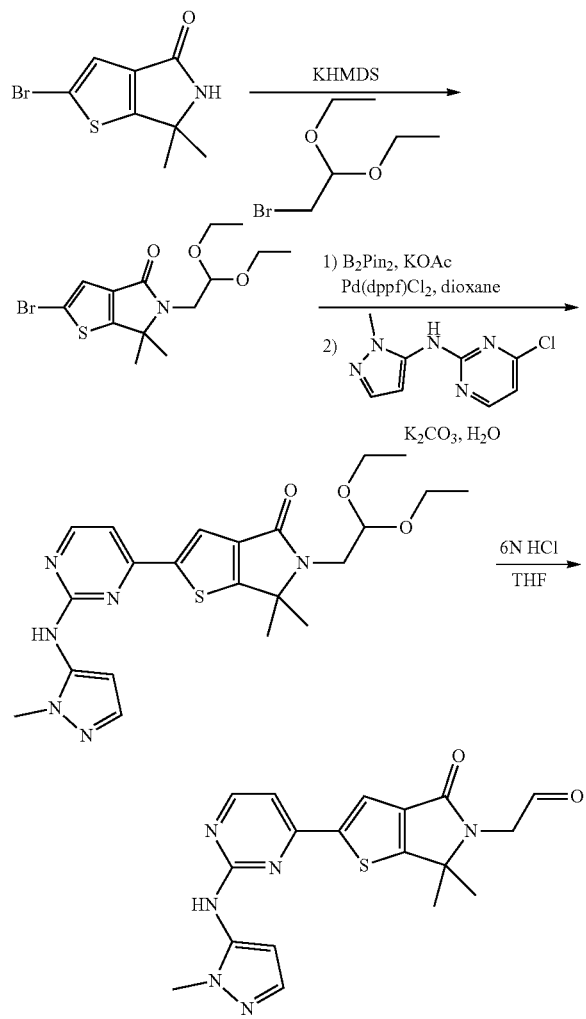

Step 1. 2-bromo-5-(2,2-diethoxyethyl)-6,6-dimethyl-5,6-dihydro-4H-thieno[2,3-c]pyrrol-4-one To a solution of Intermediate 2 (4.0 g, 16.3 mmol) in anhydrous THF (20 mL) was added KHMDS (1.0 N in THF, 17.9 mmol) at rt. The mixture was stirred at rt for 30 min before adding 2-bromo-1,1-diethoxyethane (3.52 g, 16.3 mmol). The resulting mixture was stirred at 100° C. for 18 h, cooled to rt, diluted with EtOAc (200 mL), washed with water (50×2 mL) and brine (50 mL), dried over $Na_2SO_4$ and concentrated. The residue was purified by flash column chromatography on silica gel (PE/EtOAc=4/1) to give the title compound (4.5 g, yield: 51%).

Step 2. 5-(2,2-diethoxyethyl)-6,6-dimethyl-2-(2-((1-methyl-1H-pyrazol-5-yl)amino)pyrimidin-4-yl)-5,6-dihydro-4H-thieno[2,3-c]pyrrol-4-one A solution of the product of Step 1 above (1.1 g, 4.4 mmol), $Pd(dppf)Cl_2·CH_2Cl_2$ (169 mg, 0.21 mmol) and KOAc (812 mg, 8.3 mmol) in dioxane (8 m) was charged with $N_2$. The mixture was stirred at 90° C. for 2 h. After cooling to rt, 4-chloro-N-(1-methyl-1H-pyrazol-5-yl)pyrimidin-2-amine (781 mg, 3.7 mmol), $Pd(dppf)Cl_2·CH_2Cl_2$ (151 mg, 0.19 mmol), $K_2CO_3$ (1.0 g, 7.4 mmol), and dioxane/$H_2O$ (10/2 mL) were added to the reaction mixture, which was stirred at 100° C. for 18 h. After cooling to rt, the mixture was diluted with EtOAc (100 mL), washed by water (30×2 m) and brine (30 L), dried by $Na_2SO_4$ and concentrated. The residue was purified by flash column chromatography on silica gel (DCM/MeOH=100/1) to give the title compound (410 mg, yield: 24%).

Step 3. 2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetaldehyde To a solution of the product of Step 2 above (410 mg, 0.9 mmol) in THF (10 mL) was added aqueous HCl (6N, 5 mL). After stirring at rt for 3 h, The mixture was cooled in ice-water bath, adjusted to PH=8-9 by $Na_2CO_3$ (aq), and extracted with EtOAc (50 mL×3). The combined organic layers were washed by brine (30 mL), dried by $Na_2SO_4$ and concentrated to give the title compound (280 mg, yield: 81%). MS (ESI) m/z=383.2 $[M+H]^+$.

Example 1

6,6-dimethyl-2-(2-(1-methyl-1H-pyrazol-5-ylamino)pyrimidin-4-yl)-5-((2-(trifluoromethyl)pyridin-4-yl)methyl)-5,6-dihydro-4H-thieno[2,3-c]pyrrol-4-one

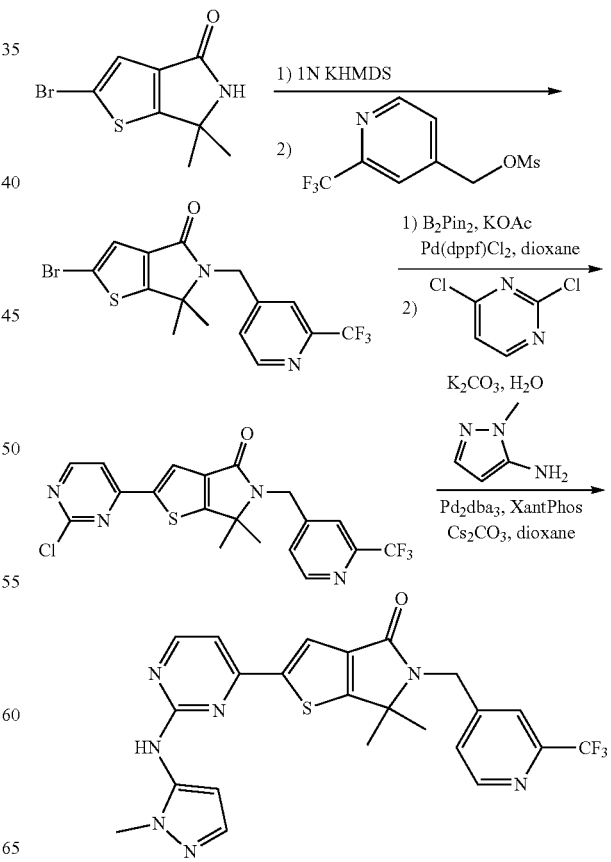

Step 1. 2-bromo-6,6-dimethyl-5-((2-(trifluoromethyl)pyridin-4-yl)methyl)-5,6-dihydro-4H-thieno[2,3-c]pyrrol-4-one To a solution of Intermediate 2 (139 mg, 0.565 mmol) in THF (10 mL) under stirring at rt was added KHMDS (1 N, 0.678 mL, 0.678 mmol) under $N_2$. The mixture was stirred at rt for 30 min before adding Intermediate 1 (173 mg, 0.678 mmol). The reaction mixture was stirred at 90° C. for 18 h under $N_2$ after LC/MS showed the reaction was completed. The reaction mixture was diluted with ethyl acetate (60 mL), washed with $H_2O$ (30 mL×2) and brine (30 mL), dried over anhydrous $Na_2SO_4$, and concentrated in vacuo. The residue was purified via prep-TLC, eluting with hexanes/ethyl acetate (1:1), to give the crude title compound as yellow oil (241 mg, crude yield: >100%).

Step 2. 2-(2-chloropyrimidin-4-yl)-6,6-dimethyl-5-((2-(trifluoromethyl)pyridin-4-yl)methyl)-5,6-dihydro-4H-thieno[2,3-c]pyrrol-4-one To a solution of the product of Step 1 above (276 mg, 0.681 mmol) in dioxane (10 mL) were added $B_2pin_2$ (182 mg, 0.715 mmol), potassium acetate (134 mg, 1.362 mmol) and $Pd_2(dppf)Cl_2 \cdot CH_2Cl_2$ (28 mg, 0.0341 mmol) sequentially. The reaction mixture was stirred at 100° C. for 2.5 h under $N_2$ and cooled to rt when LC/MS showed the starting material was consumed. Then 2,4-dichloropyrimidine (101 mg, 0.681 mmol), potassium carbonate (235 mg, 1.703 mmol) and $H_2O$ (2 mL) were added sequentially to the reaction mixture. The reaction mixture was stirred at 110° C. for 18 h under $N_2$ after TLC showed the reaction was completed. The reaction mixture was cooled to rt, diluted with dichloromethane (80 mL), washed with $H_2O$ (60 mL×2) and brine (60 mL), dried over anhydrous $Na_2SO_4$, and concentrated in vacuo. The residue was purified via flash column chromatography, eluting with hexanes/ethyl acetate (1:1~1:2), to give crude product, which was purified by prep-TLC, eluting with hexanes/ethyl acetate (1:2), to give the desired compound (50 mg, yield: 17%) as a white solid

Step 3. 6,6-dimethyl-2-(2-(1-methyl-1H-pyrazol-5-ylamino)pyrimidin-4-yl)-5-((2-(trifluoromethyl)pyridin-4-yl)methyl)-5,6-dihydro-4H-thieno[2,3-c]pyrrol-4-one To a solution of the product of Step 2 above (50 mg, 0.114 mmol) in dioxane (5 mL) were added 1-methyl-1H-pyrazol-5-amine (12 mg, 0.125 mmol), cesium carbonate (82 mg, 0.251 mmol), $Pd_2(dba)_3$ (5 mg, 0.0057 mmol) and Xantphos (7 mg, 0.0114 mmol) sequentially. The reaction mixture was stirred at 110° C. for 2 h under $N_2$ and cooled to rt when TLC showed the reaction was completed. The mixture was diluted with dichloromethane/methanol (10:1, 50 mL), washed with $H_2O$ (30 mL×2) and brine (30 mL), dried over anhydrous $Na_2SO_4$, and concentrated in vacuo. The product was purified via prep-TLC, eluting with dichloromethane/methanol (20:1), to give the desired compound as a yellow solid (23 mg, yield: 41%). MS (ESI) m/z: 500.1 [M+1]$^+$; $^1$H NMR (400 MHz, $CD_3OD$) δ/ppm: 9.54 (s, 1H), 8.67 (d, J=5.0 Hz, 1H), 8.49 (d, J=5.2 Hz, 1H), 8.19 (s, 1H), 7.85 (s, 1H), 7.61 (d, J=4.8 Hz, 1H), 7.50 (d, J=5.2 Hz, 1H), 7.35 (d, J=1.8 Hz, 1H), 6.28 (d, J=1.6 Hz, 1H), 4.79 (s, 2H), 3.68 (s, 3H), 1.49 (s, 6H).

Table 1 lists examples that were prepared according to the procedures as described in Example 1 by using the corresponding intermediates and reagents under appropriate conditions that could be accomplished by the skilled persons.

TABLE 1

| Ex. | Structure | Chemical Name | LC/MS [M + H]$^+$ | 1H-NMR (400 MHz) |
|---|---|---|---|---|
| 2 | 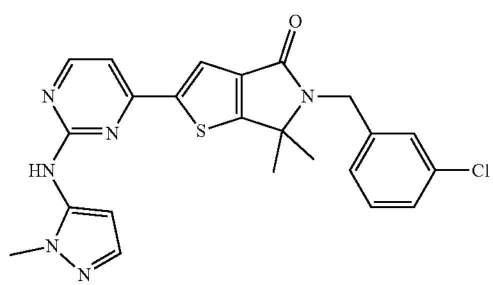 [SMILES: Cn1nccc1Nc1nccc(-c2cc3c(s2)C(C)(C)N(Cc2cccc(Cl)c2)C3=O)n1] | 5-(3-chlorobenzyl)-6,6-dimethyl-2-(2-(1-methyl-1H-pyrazol-5-ylamino)pyrimidin-4-yl)-5,6-dihydro-4H-thieno[2,3-c]pyrrol-4-one | 465.1 | $^1$H NMR (400 MHz, DMSO-d6) δ 9.52 (s, 1H), 8.48 (d, J = 5.2 Hz, 1H), 8.17 (s, 1H), 7.50 (d, J = 5.2 Hz, 1H), 7.41 (s, 1H), 7.35 (d, J = 1.9 Hz, 1H), 7.32 (t, J = 6.6 Hz, 2H), 7.30-7.27 (m, 1H), 6.28 (d, J = 1.7 Hz, 1H), 4.64 (s, 2H), 3.68 (s, 3H), 1.45 (s, 6H). |
| 3 | 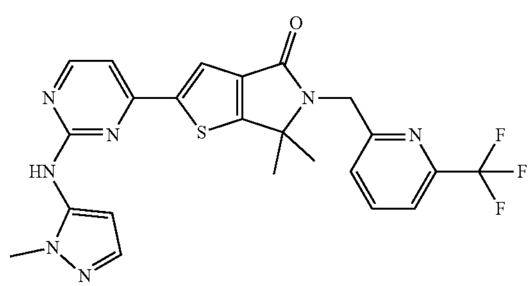 [SMILES: Cn1nccc1Nc1nccc(-c2cc3c(s2)C(C)(C)N(Cc2cccc(C(F)(F)F)n2)C3=O)n1] | 6,6-dimethyl-2-(2-((1-methyl-1H-pyrazol-5-yl)amino)pyrimidin-4-yl)-5-((6-(trifluoromethyl)pyridin-2-yl)methyl)-5,6-dihydro-4H-thieno[2,3-c]pyrrol-4-one | 500.2 | $^1$H NMR (400 MHz, DMSO-d6) δ 9.51 (s, 1H), 8.48 (d, J = 5.2 Hz, 1H), 8.16 (s, 1H), 8.02 (t, J = 7.9 Hz, 1H), 7.77 (d, J = 7.7 Hz, 1H), 7.63 (d, J = 8.0 Hz, 1H), 7.50 (d, J = 5.2 Hz, 1H), 7.35 (d, J = 1.8 Hz, 1H), 6.28 (d, J = 1.6 Hz, 1H), 4.80 (s, 2H), 3.69 (s, 3H), 1.51 (s, 6H). |

TABLE 1-continued

| Ex. | Structure | Chemical Name | LC/MS [M + H]+ | 1H-NMR (400 MHz) |
|---|---|---|---|---|
| 4 | 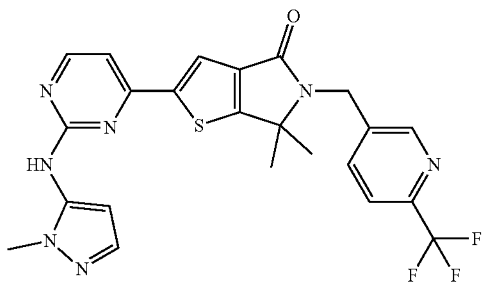 [SMILES: Cn1nccc1Nc1nccc(-c2cc3c(s2)C(C)(C)N(Cc2ccc(C(F)(F)F)nc2)C3=O)n1] | 6,6-dimethyl-2-(2-((1-methyl-1H-pyrazol-5-yl)amino)pyrimidin-4-yl)-5-((6-(trifluoromethyl)pyridin-3-yl)methyl)-5,6-dihydro-4H-thieno[2,3-c]pyrrol-4-one | 500.2 | $^1$H NMR (400 MHz, DMSO-d6) δ 9.51 (s, 1H), 8.78 (s, 1H), 8.48 (d, J = 5.2 Hz, 1H), 8.17 (s, 1H), 8.00 (d, J = 8.2 Hz, 1H), 7.84 (d, J = 8.1 Hz, 1H), 7.50 (d, J = 5.2 Hz, 1H), 7.35 (d, J = 1.9 Hz, 1H), 6.28 (d, J = 1.7 Hz, 1H), 4.78 (s, 2H), 3.68 (s, 3H), 1.50 (s, 6H). |
| 5 | 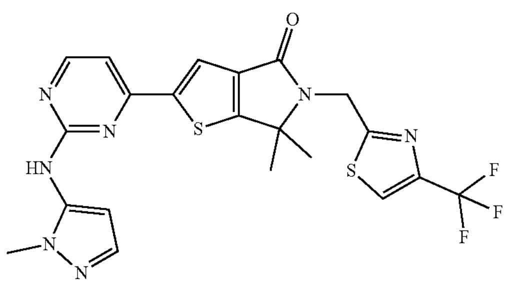 [SMILES: Cn1nccc1Nc1nccc(-c2cc3c(s2)C(C)(C)N(Cc2nc(C(F)(F)F)cs2)C3=O)n1] | 6,6-dimethyl-2-(2-((1-methyl-1H-pyrazol-5-yl)amino)pyrimidin-4-yl)-5-((4-(trifluoromethyl)thiazol-2-yl)methyl)-5,6-dihydro-4H-thieno[2,3-c]pyrrol-4-one | 506.1 | $^1$H NMR (400 MHz, DMSO-d6) δ 9.52 (s, 1H), 8.49 (d, J = 5.2 Hz, 1H), 8.42 (d, J = 0.6 Hz, 1H), 8.18 (s, 1H), 7.49 (d, J = 5.2 Hz, 1H), 7.35 (d, J = 1.8 Hz, 1H), 6.28 (d, J = 1.7 Hz, 1H), 4.98 (s, 2H), 3.69 (s, 3H), 1.55 (s, 6H), |
| 6 | 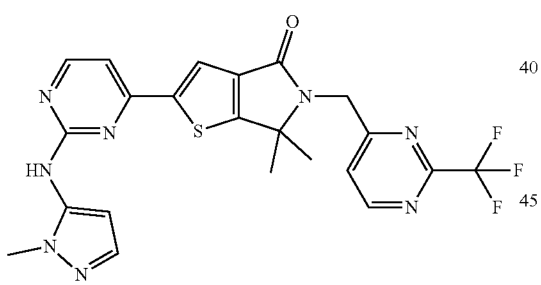 | 6,6-dimethyl-2-(2-((1-methyl-1H-pyrazol-5-yl)amino)pyrimidin-4-yl)-5-((2-(trifluoromethyl)pyrimidin-4-yl)methyl)-5,6-dihydro-4H-thieno[2,3-c]pyrrol-4-one | 501.2 | $^1$H NMR (400 MHz, CD$_3$OD) δ 8.89 (d, J = 5.2 Hz, 1H), 8.43 (d, J = 5.2 Hz, 1H), 7.95 (s, 1H), 7.70 (d, J = 5.2 Hz, 1H), 7.45 (d, J = 2.0 Hz, 1H), 7.34 (d, J = 5.2 Hz, 1H), 6.36 (d, J = 2.0 Hz, 1H), 4.90 (s, 2H), 3.77 (s, 3H), 1.62 (s, 6H). |
| 7 | 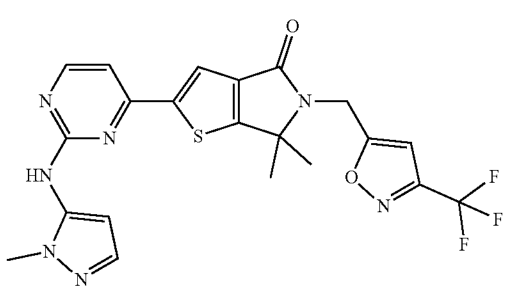 [SMILES: Cn1nccc1Nc1nccc(-c2cc3c(s2)C(C)(C)N(Cc2cc(C(F)(F)F)no2)C3=O)n1] | 6,6-dimethyl-2-(2-((1-methyl-1H-pyrazol-5-yl)amino)pyrimidin-4-yl)-5-((3-(trifluoromethyl)isoxazol-5-yl)methyl)-5,6-dihydro-4H-thieno[2,3-c]pyrrol-4-one | 490.1 | $^1$H NMR (400 MHz, acetone) δ 8.51 (s, 1H), 8.49 (d, J = 5.2 Hz, 1H), 7.97 (s, 1H), 7.44 (d, J = 5.2 Hz, 1H), 7.36 (d, J = 1.6 Hz, 1H), 6.92 (s, 1H), 6.33 (s, 1H), 4.97 (s, 2H), 3.80 (s, 3H), 1.68 (s, 6H). |

Example 8

6,6-dimethyl-2-(2-((1-methyl-1H-pyrazol-5-yl)amino)pyrimidin-4-yl)-5-(2-(2-(trifluoromethyl)pyridin-4-yl)ethyl)-5,6-dihydro-4H-thieno[2,3-c]pyrrol-4-one

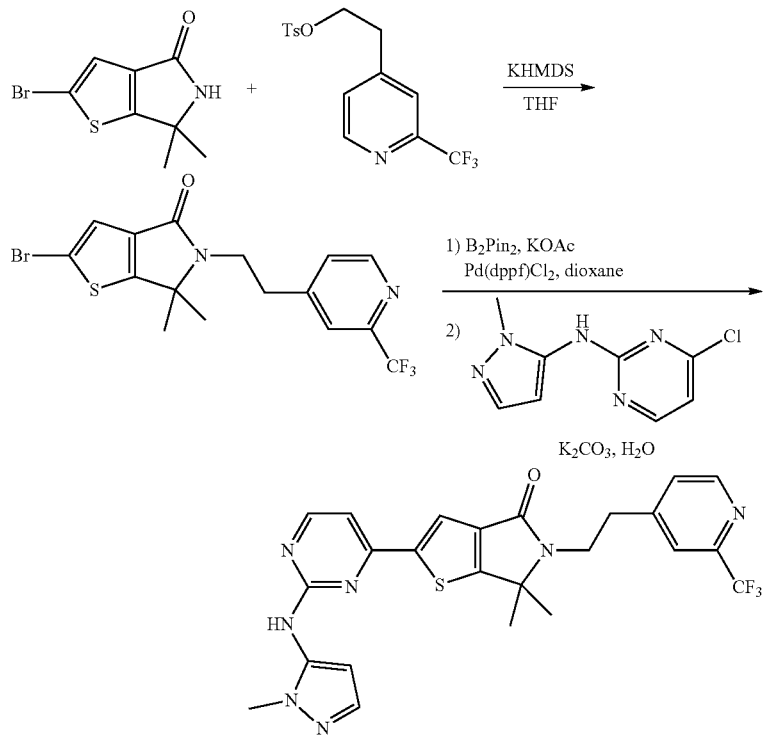

Step 1. 2-bromo-6,6-dimethyl-5-(2-(2-(trifluoromethyl)pyridin-4-yl)ethyl)-5,6-dihydro-4H-thieno[2,3-c]pyrrol-4-one To a solution of Intermediate 2 (810 mg, 3.3 mmol) in THF (8 mL) was added KHMDS (1 N in THF, 3.96 mL, 3.96 mmol) at 0° C. under $N_2$. The mixture was stirred at rt for 0.5 h before adding a solution of Intermediate 5 (1.14 g, 3.3 mmol) in THF (2 mL). The mixture was stirred at 80° C. overnight, cooled to rt, quenched with saturated aqueous $NH_4Cl$, and extracted with EtOAc (200 mL). The organic layer was washed with water (40 mL×2) and brine (40 mL), dried over anhydrous $Na_2SO_4$, and concentrated. The residue was purified by flash column chromatography on silica gel (PE/EtOAc=8/1 to 4/1) to give the title compound (570 mg, yield: 39%).

Step 2. 6,6-dimethyl-2-(2-((1-methyl-1H-pyrazol-5-yl)amino)pyrimidin-4-yl)-5-(2-(2-(trifluoromethyl)pyridin-4-yl)ethyl)-5,6-dihydro-4H-thieno[2,3-c]pyrrol-4-one To a solution of the product of Step 1 above (100 mg, 0.24 mmol) in dioxane (0.5 mL) were added $B_2pin_2$ (64 mg, 0.25 mmol), KOAc (47 mg, 0.478 mmol) and Pd(dppf)$Cl_2 \cdot CH_2Cl_2$ (10 mg, 0.012 mmol) sequentially. The reaction mixture was stirred at 90° C. for 2.5 h under $N_2$. After cooling to rt, 4-chloro-N-(1-methyl-1H-pyrazol-5-yl)pyrimidin-2-amine (50 mg, 0.24 mmol), $K_2CO_3$ (66 mg, 0.48 mmol) and $H_2O$ (0.2 mL) were added sequentially and the reaction mixture was flushed with $N_2$ and stirred at 110° C. for 18 h. The resultant mixture was cooled to rt, diluted with DCM/MeOH (10/1, 20 mL), washed with water (15 mL×2) and brine (20 mL), dried over anhydrous $Na_2SO_4$, and concentrated. The residue was purified by prep-TLC (DCM/MeOH=10/1) to give the title compound (5.9 mg, yield: 5%). MS (ESI) m/z: 514.2 [M+1]$^+$; $^1$H NMR (400 MHz, CD$_3$OD) δ 8.61 (d, J=4.9 Hz, 1H), 8.42 (d, J=5.3 Hz, 1H), 7.90 (s, 1H), 7.85 (s, 1H), 7.63 (d, J=4.9 Hz, 1H), 7.45 (d, J=1.9 Hz, 1H), 7.32 (d, J=5.3 Hz, 1H), 6.35 (d, J=1.9 Hz, 1H), 3.77 (s, 3H), 3.73 (m, 2H), 3.22-3.17 (m, 2H), 1.56 (s, 6H).

Example 9

6,6-dimethyl-2-(2-(1-methyl-1H-pyrazol-5-ylamino)pyrimidin-4-yl)-5-(1-(2-(trifluoromethyl)pyridin-4-yl)ethyl)-5,6-dihydro-4H-thieno[2,3-c]pyrrol-4-one

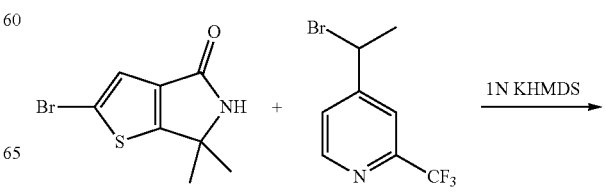

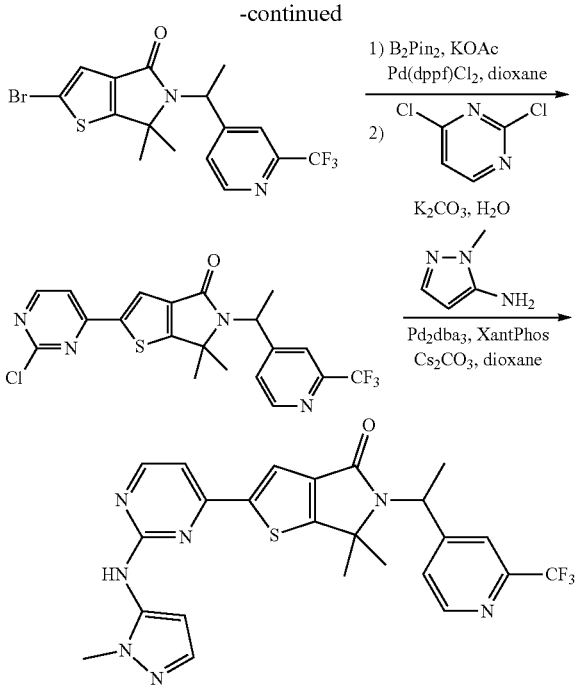

Step 1. 2-bromo-6,6-dimethyl-5-(1-(2-(trifluoromethyl)pyridin-4-yl)ethyl)-5,6-dihydro-4H-thieno[2,3-c]pyrrol-4-one To a stirred solution of Intermediate 2 (5.5 g, 22.34 mmol) in THF (100 mL) was added KHMDS (1 N, 26.8 mL, 26.8 mmol) under $N_2$ at 0° C. After stirring at rt for 30 min, Intermediate 3 (6.8 g, 26.8 mmol) was added to the reaction mixture. The reaction was stirred at 70° C. for 18 h under $N_2$. After cooling, the mixture was taken up in EtOAc (80 mL), which was washed with water (40 mL×2) and brine (40 mL), dried over anhydrous $Na_2SO_4$, and concentrated. The residue was purified by flash column chromatography on silica gel (PE/EtOAc=8/1 to 3/1) to give the title compound (6.8 g, yield: 73%).

Step 2. 2-(2-chloropyrimidin-4-yl)-6,6-dimethyl-5-(1-(2-(trifluoromethyl)pyridin-4-yl)ethyl)-5,6-dihydro-4H-thieno[2,3-c]pyrrol-4-one The product of Step 1 above (3.8 g, 9.06 mmol) in dioxane (20 mL) was added $B_2pin_2$ (2.37 g, 9.33 mmol), KOAc (2.66 g, 27.2 mmol) and Pd(dppf)$Cl_2$·$CH_2Cl_2$ (370 mg, 0.453 mmol) sequentially. The reaction mixture was stirred at 90° C. for 4 h under $N_2$. After cooling to rt, 2,4-dichloropyrimidine (1.35, 9.06 mmol), $K_2CO_3$ (2.5 g, 18.12 mmol) and $H_2O$ (5 mL) were added sequentially, the reaction mixture was flushed with $N_2$ and stirred at 110° C. for 10 h. The resultant mixture was cooled to rt, diluted with DCM/MeOH (10/1, 100 mL), washed with water (60 mL×2) and brine (60 mL), dried over anhydrous $Na_2SO_4$, and concentrated. The residue was purified by flash column chromatography on silica gel (DCM/MeOH=100/1 to 50/1) to give the title compound (1.6 g, yield: 25%).

Step 3. 6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one The product of Step 2 above (1.8 g, 3.97 mmol) in dioxane (40 mL) were added 1-methyl-1H-pyrazol-5-amine (1.35 g, 13.9 mmol), $Cs_2CO_3$ (2.58 g, 7.94 mmol), $Pd_2(dba)_3$ (182 mg, 0.198 mmol) and Xantphos (229 mg, 0.397 mmol) sequentially. The reaction mixture was stirred at 110° C. for 10 h under $N_2$. After cooling to rt, the mixture was diluted with DCM/methanol (10/1, 80 mL), washed with water (50 mL×2) and brine (50 mL), dried over anhydrous $Na_2SO_4$, and concentrated. The residue was purified by flash column chromatography on silica gel (DCM/MeOH=100/1 to 10/1) to give the title compound (1.45 g, yield: 71%). MS (ESI) m/z: 514.2 [M+1]$^+$; $^1$H NMR (400 MHz, $CD_3OD$) δ 8.65 (d, J=5.1 Hz, 1H), 8.42 (d, J=5.3 Hz, 1H), 7.90 (s, 1H), 7.89 (s, 1H), 7.73 (d, J=4.6 Hz, 1H), 7.45 (d, J=2.0 Hz, 1H), 7.33 (d, J=5.3 Hz, 1H), 6.35 (d, J=2.0 Hz, 1H), 5.02 (q, J=7.0 Hz, 1H), 3.77 (s, 3H), 1.93 (d, J=7.1 Hz, 3H), 1.75 (s, 3H), 1.61 (s, 3H).

Example 9a and 9b (R)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one and (S)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one The racemic Example 9 was separated using supercritical fluid chiral chromatography on Chiralpak OJ-H column eluting with 15% MeOH.

Example 9a: enantiomer with RT of 2.29 min; MS (ESI) m/z: 514.2 [M+1]$^+$; $^1$H NMR (400 MHz, $CD_3OD$) δ 8.65 (d, J=5.1 Hz, 1H), 8.42 (d, J=5.3 Hz, 1H), 7.90 (s, 1H), 7.89 (s, 1H), 7.73 (d, J=4.6 Hz, 1H), 7.45 (d, J=2.0 Hz, 1H), 7.33 (d, J=5.3 Hz, 1H), 6.35 (d, J=2.0 Hz, 1H), 5.02 (q, J=7.0 Hz, 1H), 3.77 (s, 3H), 1.93 (d, J=7.1 Hz, 3H), 1.75 (s, 3H), 1.61 (s, 3H).

Example 9b: enantiomer with RT of 2.98 min. MS (ESI) m/z: 514.2 [M+1]$^+$; $^1$H NMR (400 MHz, $CD_3OD$) δ 8.65 (d, J=5.1 Hz, 1H), 8.42 (d, J=5.3 Hz, 1H), 7.90 (s, 1H), 7.89 (s, 1H), 7.73 (d, J=4.6 Hz, 1H), 7.45 (d, J=2.0 Hz, 1H), 7.33 (d, J=5.3 Hz, 1H), 6.35 (d, J=2.0 Hz, 1H), 5.02 (q, J=7.0 Hz, 1H), 3.77 (s, 3H), 1.93 (d, J=7.1 Hz, 3H), 1.75 (s, 3H), 1.61 (s, 3H).

Example 10

6,6-dimethyl-2-(2-(1-methyl-1H-pyrazol-5-ylamino)pyrimidin-4-yl)-5-(1-(4-(trifluoromethyl)thiazol-2-yl)ethyl)-5,6-dihydro-4H-thieno[2,3-c]pyrrol-4-one

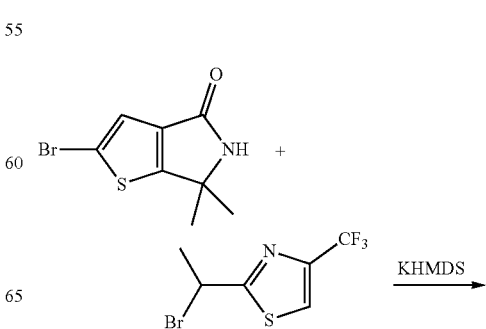

-continued

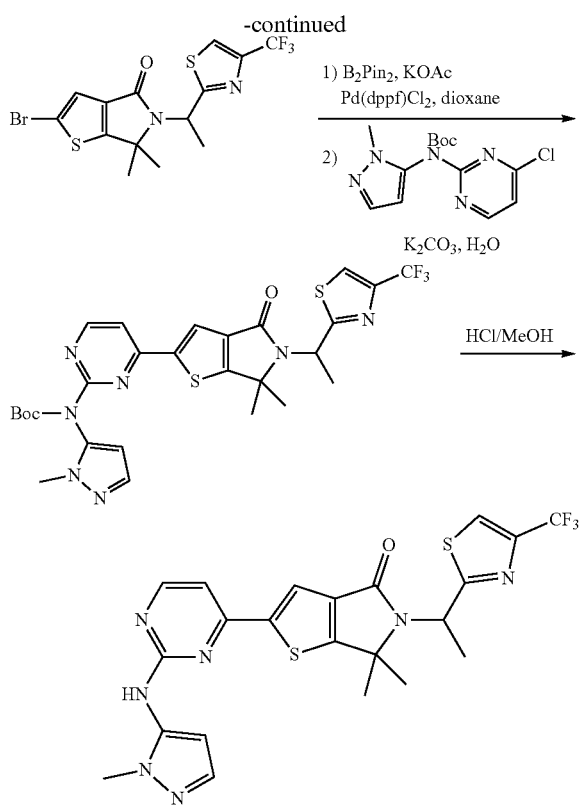

Step 1. 2-bromo-6,6-dimethyl-5-(1-(4-(trifluoromethyl)thiazol-2-yl)ethyl)-5,6-dihydro-4H-thieno[2,3-c]pyrrol-4-one To a solution of Intermediate 2 (1.23 mg, 5.01 mmol) in THF (20 mL) was added KHMDS (1N in THF, 7.52 mL, 7.52 mmol) at 0° C. The mixture was stirred at rt for 0.5 h and Intermediate 8 (1.56 g, 6.01 mmol) was added. The mixture was stirred at 90° C. overnight, cooled to rt, diluted with DCM/MeOH (10/1, 100 mL), washed with water (40 mL×2) and brine (40 mL), dried over anhydrous Na₂SO₄, and concentrated. The residue was purified by flash column chromatography on silica gel (PE/EtOAc=3/1) to give the title compound (1.21 g, yield: 57%).

Step 2. tert-butyl (4-(6,6-dimethyl-4-oxo-5-(1-(4-(trifluoromethyl)thiazol-2-yl)ethyl)-5,6-dihydro-4H-thieno[2,3-c]pyrrol-2-yl)pyrimidin-2-yl)(1-methyl-1H-pyrazol-5-yl)carbamate To a solution of the product of Step 1 above (1.21 g, 2.85 mmol) in dioxane (5 mL) were added B₂pin₂ (759 mg, 2.99 mmol), KOAc (558 mg, 5.69 mmol) and Pd(dppf)Cl₂·CH₂Cl₂ (116 mg, 0.142 mmol) sequentially. The reaction mixture was stirred at 90° C. for 3 h under N₂. After cooling to rt, tert-butyl (4-chloropyrimidin-2-yl)(1-methyl-1H-pyrazol-5-yl)carbamate (705 mg, 2.28 mmol), K₂CO₃ (786 mg, 5.69 mmol) and dioxane/H₂O (5 mL/2 ML) were added sequentially and the reaction mixture was flushed with N₂ and stirred at 100° C. for 4 h. The reaction mixture was cooled to rt, diluted with DCM/MeOH (10/1, 120 mL), washed by water (50 mL) and brine (50 mL), dried over anhydrous Na₂SO₄, and concentrated. The residue was purified by Na₂SO₄, and concentrated. The residue was purified by flash column chromatography on silica gel (DCM/MeOH=100/1 to 50/1) to give the title compound (1.03 g, yield: 58%).

Step 3. 6,6-dimethyl-2-(2-((1-methyl-1H-pyrazol-5-yl)amino)pyrimidin-4-yl)-5-(1-(4-(trifluoromethyl)thiazol-2-yl)ethyl)-5,6-dihydro-4H-thieno[2,3-c]pyrrol-4-one To a solution of the product of Step 2 above (1.03 g, 1.66 mmol) in DCM/MeOH (10 mL) added HCl (4 N in dioxane, 6 mL). After stirring at rt for 2 h, the reaction mixture was concentrated to a small volume and saturated aqueous Na₂CO₃ added until pH was 8~9. The mixture was extracted with DCM/MeOH (10/1, 100 mL). The extract was washed by water (50 mL) and brine (50 mL), dried over anhydrous Na₂SO₄, and concentrated. The residue was purified by reverse phase flash column chromatography (H₂O/MeOH=80/20 to 20/80) to give the title compound (617 mg, yield: 71%). MS (ESI) m/z: 520.2 [M+1]⁺; ¹H NMR (400 MHz, DMSO-d6) δ 9.52 (s, 1H), 8.48 (d, J=5.2 Hz, 1H), 8.40 (s, 1H), 8.10 (s, 1H), 7.49 (d, J=5.2 Hz, 1H), 7.36 (d, J=1.7 Hz, 1H), 6.29 (d, J=1.4 Hz, 1H), 5.27 (q, J=6.8 Hz, 1H), 3.69 (s, 3H), 1.82 (d, J=6.8 Hz, 3H), 1.66 (d, J=3.6 Hz, 6H).

Example 10a and 10b (R)-6,6-dimethyl-2-(2-((1-methyl-1H-pyrazol-5-yl)amino)pyrimidin-4-yl)-5-(1-(4-(trifluoromethyl)thiazol-2-yl)ethyl)-5,6-dihydro-4H-thieno[2,3-c]pyrrol-4-one and (S)-6,6-dimethyl-2-(2-((1-methyl-1H-pyrazol-5-yl)amino)pyrimidin-4-yl)-5-(1-(4-(trifluoromethyl)thiazol-2-yl)ethyl)-5,6-dihydro-4H-thieno[2,3-c]pyrrol-4-one The racemic Example 10 was separated using supercritical fluid chiral chromatography on Cellulose-SC column eluting with 25% MeOH.

Example 10a: enantiomer with RT of 1.92 min; MS (ESI) m/z=520.0 [M+H]⁺; ¹H NMR (400 MHz, DMSO-d6) δ 9.51 (s, 1H), 8.48 (d, J=5.2 Hz, 1H), 8.40 (s, 1H), 8.10 (s, 1H), 7.49 (d, J=5.2 Hz, 1H), 7.36 (d, J=1.9 Hz, 1H), 6.29 (d, J=1.7 Hz, 1H), 5.27 (q, J=6.8 Hz, 1H), 3.69 (s, 3H), 1.82 (d, J=6.8 Hz, 3H), 1.67 (s, 3H), 1.66 (s, 3H).

Example 10b: enantiomer with RT of 2.46 min; MS (ESI) m/z=520.0 [M+H]⁺; ¹H NMR (400 MHz, DMSO-d6) δ 9.52 (s, 1H), 8.48 (d, J=5.2 Hz, 1H), 8.40 (s, 1H), 8.10 (s, 1H), 7.49 (d, J=5.2 Hz, 1H), 7.36 (d, J=1.8 Hz, 1H), 6.29 (d, J=1.7 Hz, 1H), 5.27 (q, J=6.7 Hz, 1H), 3.69 (s, 3H), 1.82 (d, J=6.8 Hz, 3H), 1.67 (s, 3H), 1.66 (s, 3H).

Example 11

(S)-5-(1-(3-chlorophenyl)-2-hydroxyethyl)-6,6-dimethyl-2-(2-((1-methyl-1H-pyrazol-5-yl)amino)pyrimidin-4-yl)-5,6-dihydro-4H-thieno[2,3-c]pyrrol-4-one

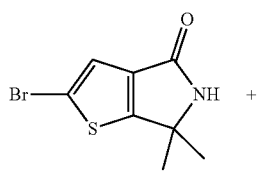

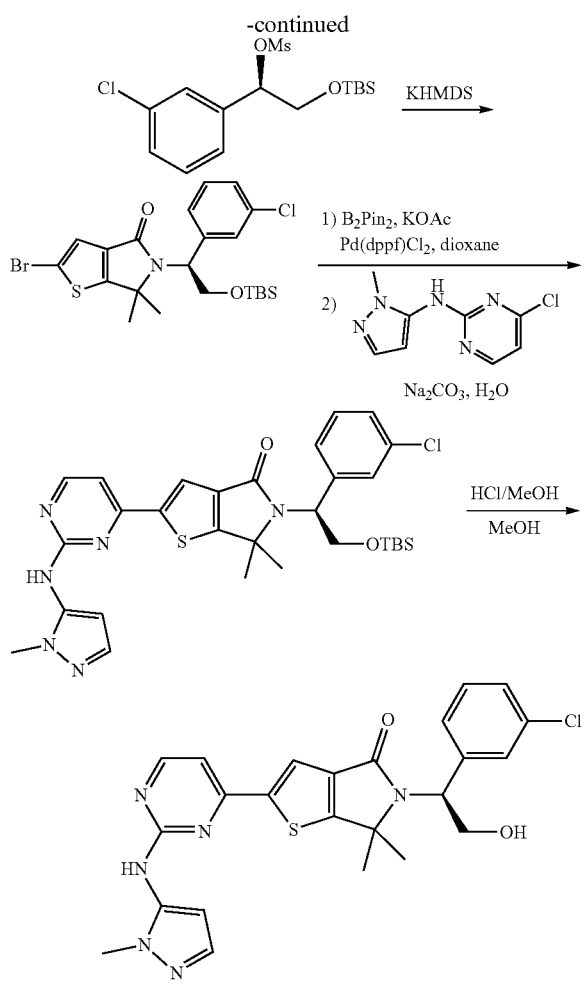

Step 1. (S)-2-bromo-5-(2-((tert-butyldimethylsilyl)oxy)-1-(3-chlorophenyl)ethyl)-6,6-dimethyl-5,6-dihydro-4H-thieno[2,3-c]pyrrol-4-one To a solution of Intermediate 2 (156 mg, 0.63 mmol) in THF (5 mL) was added KHMDS (1 N in THF, 0.75 mL, 0.75 mmol) at rt. The mixture was stirred at rt for 0.5 h and a solution of Intermediate 4 (300 mg, 0.548 mmol) in THF (2 mL) was added. The mixture was stirred at 80° C. overnight, cooled to rt, diluted with EtOAc (50 mL), washed with water (15 mL×2) and brine (15 mL), dried over anhydrous $Na_2SO_4$, and concentrated. The residue was purified by flash column chromatography on silica gel (PE/EtOAc=4/1) to give the title compound (125 mg, yield: 43%).

Step 2. (S)-5-(2-((tert-butyldimethylsilyl)oxy)-1-(3-chlorophenyl)ethyl)-6,6-dimethyl-2-(2-((1-methyl-1H-pyrazol-5-yl)amino)pyrimidin-4-yl)-5,6-dihydro-4H-thieno[2,3-c]pyrrol-4-one To a solution of the product of Step 1 above (125 mg, 0.24 mmol) in dioxane (2 mL) were added $B_2pin_2$ (65 mg, 0.25 mmol), KOAc (125 mg, 27.2 mmol) and Pd(dppf)$Cl_2 \cdot CH_2Cl_2$ (10 mg, 0.012 mmol) sequentially. The reaction mixture was stirred at 100° C. for 2 h under $N_2$. After cooling to rt, 4-chloro-N-(1-methyl-1H-pyrazol-5-yl)pyrimidin-2-amine (50 mg, 0.24 mmol), sodium carbonate (50 mg, 0.48 mmol) and dioxane/$H_2O$ (2 mL/0.4 mL) were added sequentially and the reaction mixture was flushed with $N_2$ and stirred at 100° C. for 18 h. The resultant mixture was cooled to rt, diluted with EtOAc (50 mL), washed with $H_2O$ (15 mL×2) and brine (15 mL), dried over anhydrous $Na_2SO_4$, and concentrated. The residue was purified by prep-TLC (PE/EtOAc=1/2) to give the title compound (55 mg, yield: 38%).

Step 3. (S)-5-(1-(3-chlorophenyl)-2-hydroxyethyl)-6,6-dimethyl-2-(2-((1-methyl-1H-pyrazol-5-yl)amino)pyrimidin-4-yl)-5,6-dihydro-4H-thieno[2,3-c]pyrrol-4-one To a solution of the product of Step 2 above (55 mg, 0.09 mmol) in MeOH (3 mL) was added HCl (4N in MeOH, 1 mL) at rt. The mixture was stirred at rt for 18 h and concentrated. The residue was dissolved in DCM/MeOH (10/1, 50 mL), washed with saturated aqueous $Na_2CO_3$ (15 mL), water (15 mL), and brine (15 mL), dried over anhydrous $Na_2SO_4$, and concentrated. The residue was purified by prep-TLC (DCM/MeOH=10/1) to give the title compound (26 mg, yield: 58%). MS (ESI) m/z: 495.3 [M+1]$^+$; $^1$H NMR (400 MHz, $CD_3OD$) δ 8.42 (d, J=5.2 Hz, 1H), 7.92 (s, 1H), 7.62 (s, 1H), 7.45 (dd, J=10.7, 4.7 Hz, 2H), 7.34-7.24 (m, 3H), 6.35 (d, J=1.9 Hz, 1H), 4.70-4.54 (m, 2H), 4.03 (m, 1H), 3.76 (s, 3H), 1.70 (s, 3H), 1.40 (s, 3H).

Table 2 lists examples that were prepared according to the procedures as described in Examples 9-11 by using the corresponding intermediates and reagents under appropriate conditions that could be accomplished by the skilled persons.

TABLE 2

| Example | Structure | Chemical Name | LC/MS [M + H]$^+$ | 1H-NMR (400 MHz) |
|---|---|---|---|---|
| 12 | 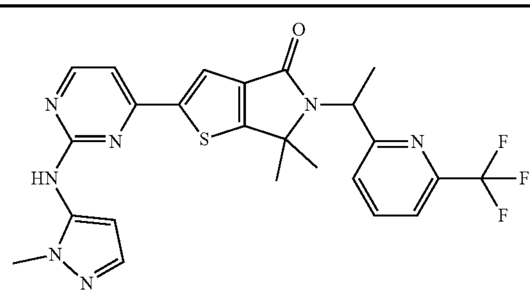 | 6,6-dimethyl-2-(2-((1-methyl-1H-pyrazol-5-yl)amino)pyrimidin-4-yl)-5-(1-(6-(trifluoromethyl)pyridin-2-yl)ethyl)-5,6-dihydro-4H-thieno[2,3-c]pyrrol-4-one | 514.2 | $^1$H NMR (400 MHz, $CD_3OD$) δ 8.40 (d, J = 5.3 Hz, 1H), 7.97 (t, J = 7.9 Hz, 1H), 7.83 (d, J = 7.5 Hz, 1H), 7.81 (d, J = 8.1 Hz, 1H), 7.64 (d, J = 7.7 Hz, 1H), 7.45 (d, J = 2.0 Hz, 1H), 7.30 (d, J = 5.3 Hz, 1H), 6.36 (d, J = 2.0 Hz, 1H), 4.95 (q, J = 7.1 Hz, 1H), 3.76 (s, 3H), 1.96 (d, J = 7.1 Hz, 3H), 1.71 (s, 3H), 1.69 (s, 3H). |

TABLE 2-continued

| Example | Structure | Chemical Name | LC/MS [M + H]+ | 1H-NMR (400 MHz) |
|---|---|---|---|---|
| 13 | 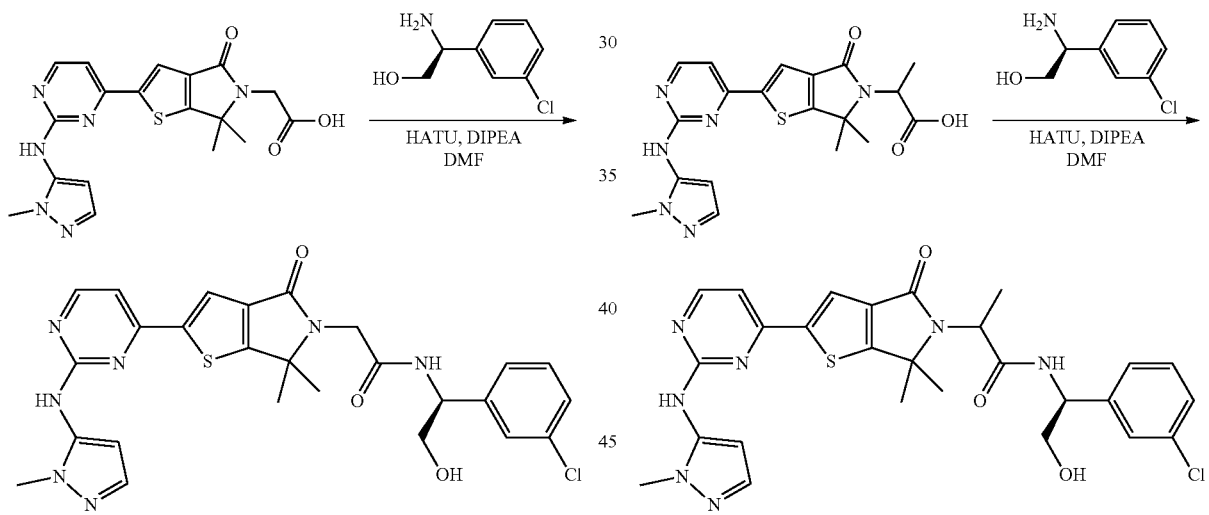 | 6,6-dimethyl-2-(2-((1-methyl-1H-pyrazol-5-yl)amino)pyrimidin-4-yl)-5-(1-(2-(trifluoromethyl)pyrimidin-4-yl)ethyl)-5,6-dihydro-4H-thieno[2,3-c]pyrrol-4-one | 515.1 | 1H NMR (400 MHz, DMSO-d6) δ 9.52 (s, 1H), 8.94 (d, J = 5.4 Hz, 1H), 8.47 (d, J = 5.2 Hz, 1H), 8.07 (s, 1H), 7.80 (d, J = 5.3 Hz, 1H), 7.48 (d, J = 5.2 Hz, 1H), 7.36 (d, J = 1.5 Hz, 1H), 6.29 (d, J = 1.0 Hz, 1H), 5.07 (q, J = 6.7 Hz, 1H), 3.69 (s, 3H), 1.80 (d, J = 6.9 Hz, 3H), 1.67 (d, J = 5.0 Hz, 6H). |

Example 14

(S)—N-(1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetamide Example 15

N—((S)-1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanamide To a solution of Intermediate 9 (100 mg, 0.25 mg) and (S)-2-amino-2-(3-chlorophenyl)ethanol (47 mg, 0.28 mmol) in DMF (5 mL) were added HATU (142 mg, 0.38 mmol) and DIPEA (96 mg, 0.75 mmol). The mixture was stirred at rt overnight and concentrated. The residue was dissolved in DCM/MeOH (10/1, 60 mL), washed with water (30 mL×2) and brine (30 L), dried over anhydrous Na2SO4, and concentrated in vacuo. The residue was purified by prep-TLC (silica gel, DCM/MeOH=10/1) to give the title compound (102 mg, yield: 74%). MS (ESI) m/z: 552.3 [M+1]+; 1H NMR (400 MHz, DMSO-d6) δ 9.50 (s, 1H), 8.47 (d, J=5.2 Hz, 1H), 8.34 (d, J=8.1 Hz, 1H), 8.14 (s, 1H), 7.48 (d, J=5.2 Hz, 1H), 7.38 (s, 1H), 7.35 (d, J=1.8 Hz, 1H), 7.32 (d, J=7.3 Hz, 1H), 7.29 (s, 1H), 7.27 (d, J=1.6 Hz, 1H), 6.28 (d, J=1.4 Hz, 1H), 4.92 (t, J=5.5 Hz, 1H), 4.84 (dd, J=13.8, 6.1 Hz, 1H), 4.09 (s, 2H), 3.68 (s, 3H), 3.57 (t, J=5.8 Hz, 2H), 1.49 (s, 3H), 1.45 (s, 3H).

To a solution of Intermediate 10 (100 mg, 0.242 mg) and (S)-2-amino-2-(3-chlorophenyl)ethanol (46 mg, 0.27 mmol) in DMF (5 mL) were added HATU (138 mg, 0.363 mmol) and DIPEA (94 mg, 0.726 mmol). The mixture was stirred at rt overnight and concentrated in vacuo. The residue was dissolved in DCM/MeOH (10/1, 60 mL), washed with water (30 mL×2) and brine (30 mL), dried over anhydrous Na2SO4, and concentrated in vacuo. The residue was purified by prep-TLC (silica gel, DCM/MeOH=10/1) to give the title compound (50 mg, yield: 37%). MS (ESI) m/z: 566.2 [M+1]+; 1H NMR (400 MHz, DMSO-d6) δ 9.50 (s, 1H), 8.47 (d, J=5.2 Hz, 1H), 8.18 (s, 0.5H), 8.14 (s, 0.5H), 7.83 (d, J=7.9 Hz, 0.5H), 7.73 (d, J=8.0 Hz, 0.5H), 7.50 (t, J=5.1 Hz, 1H), 7.41 (s, 0.5H), 7.36 (d, J=1.8 Hz, 1H), 7.33-7.22 (m, 3.5H), 6.28 (d, J=1.5 Hz, 1H), 4.92-4.72 (m, 2H), 4.40-4.17 (m, 1H), 3.69 (s, 3H), 3.57 (dd, J=9.4, 5.3 Hz, 2H), 1.61-1.52 (m, 9H).

Example 16

2-(6,6-dimethyl-2-(2-((1-methyl-1H-pyrazol-5-yl)amino)pyrimidin-4-yl)-4-oxo-4H-thieno[2,3-c]pyrrol-5(6H)-yl)-N-((2-(trifluoromethyl)pyridin-4-yl)methyl)acetamide

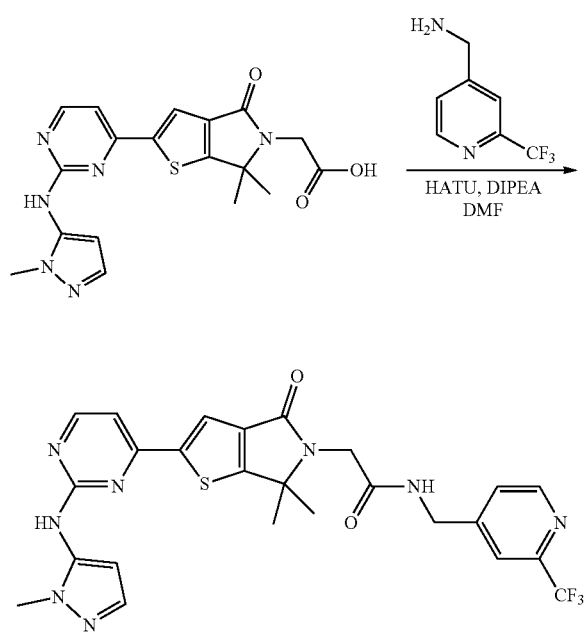

The compound was prepared according to the method described in Example 14 replacing Intermediate 12 for (S)-2-amino-2-(3-chlorophenyl)ethanol. MS (ESI) m/z: 557.1 [M+1]$^+$; $^1$H NMR (400 MHz, DMSO-d6) δ 9.49 (s, 1H), 8.68 (d, J=5.0 Hz, 1H), 8.56 (s, 1H), 8.47 (d, J=5.2 Hz, 1H), 8.16 (s, 1H), 7.78 (s, 1H), 7.60 (d, J=4.8 Hz, 1H), 7.49 (d, J=5.2 Hz, 1H), 7.35 (d, J=1.7 Hz, 1H), 6.28 (s, 1H), 4.42 (d, J=5.9 Hz, 2H), 4.10 (s, 2H), 3.69 (s, 3H), 1.53 (s, 6H).

Example 17

(S)-5-(2-((1-(3-chlorophenyl)-2-hydroxyethyl)amino)ethyl)-6,6-dimethyl-2-(2-((1-methyl-1H-pyrazol-5-yl)amino)pyrimidin-4-yl)-5,6-dihydro-4H-thieno[2,3-c]pyrrol-4-one

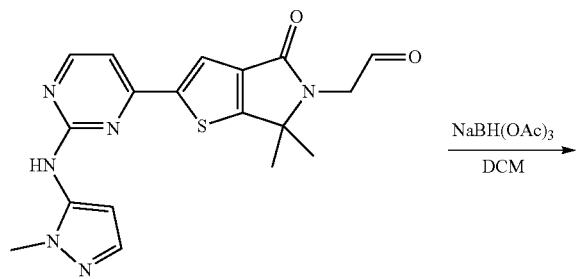

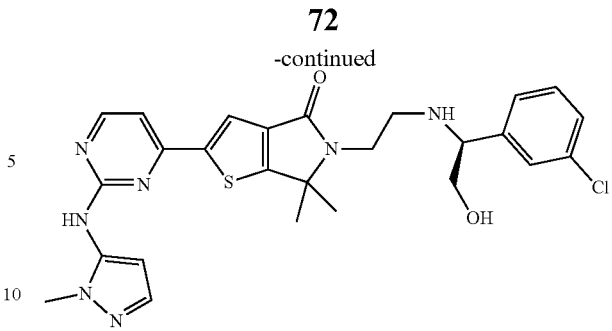

To a solution of Intermediate 13 (76 mg, 0.20 mmol) and (S)-2-amino-2-(3-chlorophenyl)ethanol (34 mg, 0.20 mmol) in DCM (5 mL) was added NaBH(OAc)$_3$ (85 mg, 0.40 mmol), followed by AcOH (40 mg, 0.6 mmol). The mixture was stirred at rt overnight, diluted with DCM/MeOH (10/1, 50 mL), washed with H$_2$O (15 mL×3) and brine (15 mL), dried over anhydrous Na$_2$SO$_4$, and concentrated. The residue was puried by Prep-TLC (DCM/MeOH=10/1) to give the title compound (45 mg, yield: 42%). MS (ESI) m/z: 538.3 [M+1]$^+$; $^1$H NMR (400 MHz, DMSO-d6) δ 9.50 (s, 1H), 8.48 (d, J=5.2 Hz, 1H), 8.09 (s, 1H), 7.47 (d, J=5.2 Hz, 2H), 7.36 (d, J=1.7 Hz, 4H), 6.28 (d, J=1.6 Hz, 1H), 3.70 (s, 3H), 3.49 (m, 4H), 2.67 (m, 2H), 1.50 (s, 3H), 1.48 (s, 3H).

Enzymatic Assay

Compounds were tested in a LanthaScreen™ time-resolved fluorescence energy transfer (TR-FRET) enzymatic assay from Invitrogen. The assay used human ERK2 (Mitogen Activated Kinase 1, Invitrogen, Cat. PV3311) recombinantly expressed as GST-tagged full-length protein purified from E. coli and activated in vitro with MAP2K1. The substrate was a recombinant truncated version (residues 19-96) of ATF2 fused with Green Fluorescent Protein (Invitrogen, Cat. PV4445). Test compounds were prepared and diluted in DMSO in 3-fold serial dilutions to 100× of the final testing concentrations. The compounds were then further diluted to 4× by the kinase reaction buffer (Invitrogen, Cat. PV3189). The enzymatic reaction for compound testing was performed in a white 384-well polypropylene plate (Packard, Cat. 6005214) with a total reaction volume of 10 μl containing 20 ng/ml ERK2, 400 nM substrate, and 5 μM ATP that is around its K$_m$. The assay started with loading 2.5 μl of ERK2 diluted in kinase reaction buffer to wells, followed by addition of equal volume of 4× compounds for 15-min incubation at the room temperature for pre-treatment. The enzymatic reaction was initiated by addition of 5 μl of mixture of the substrate and ATP prepared in kinase reaction buffer. After one hour reaction, 10 μl mixture of EDTA (final 10 mM) and terbium-labeled anti-pATF2 (pThr71) antibody (final 2 nM) (Invitrogen, Cat. PV4451) prepared in TR-FRET antibody dilution buffer (Invitrogen, Cat. PV3574) was added to stop the enzymatic reaction and produce TR-FRET signals. After 30 minutes of incubation at room temperature, the plate was read in Tecan Infinite F200 Pro with the following settings: Excitation 340 nm (30)/Emission1 495 nm (10)/Emission2 520 nm (25). The TR-FRET values were dimensionless numbers that were calculated as the ratio of the acceptor (Green Fluorescent Protein) signal to the donor (Terbium) signal. Percent of control was calculated as the percentage of compound-treated vs 1% DMSO vehicle-treated. The dose-response curves were generated and the IC$_{50}$s were calculated by nonlinear sigmoid curve fitting using GraphPad Prism.

The IC$_{50}$ values of ERK2 inhibition for compounds disclosed are listed in Table 3, A: ≤10 nM; B: >10 nM and ≤100 nM; C: >100 nM and ≤1 uM; D: >1 μM.

Colo205 Cell Proliferation Assay

Compounds disclosed herein were tested for the inhibition of ERK2 by a Colo205 cell proliferation assay commonly known as MTT assay. In this assay, a complete media was prepared by adding 10% fetal bovine serum to RPMI-1640 medium (Life technology). Colon cancer cells (Colo205 cell line) were added to each of 88 wells of a 96 well plate at a seeding density of 5,000 cells/well/90 μL. The cells were allowed to attach to the plate by incubating at 37° C. for 24 hours. The compound was dissolved in DMSO (SIGMA). A solution of test compound was prepared in complete media by serial dilution to obtain the following concentrations: 500 μM, 150 μM, 50 μM, 15 μM, 5 μM, 1.5 μM, 0.5 μM, 0.15 μM and 0.05 μM. The test compound solution (10 μL) was added to each of 80 cell-containing wells. The final concentrations of the compound were following: 50 μM, 15 μM, 5 μM, 1.5 μM, 0.5 μM, 0.15 μM, 0.05 μM, 0.015 μM and 0.005 μM. The final concentration of DMSO is 0.5%. To the 8 remaining cell-containing wells, only complete media (containing 0.5% DMSO) was added to form a control group in order to measure maximal proliferation. To the remaining 8 empty wells, complete media was added to for a vehicle control group in order to measure background. The plates were incubated at 37° C. for 72 hours. 10 μL WST-8 solution (DOJINDO, Cell Counting KIT-8) was added to each well. The plates were further incubated at 37° C. for 2 hours, and then read for the absorbance using a microplate reader at 450 nm.

The IC$_{50}$ values of growth inhibition in Colo 205 cells for compounds disclosed are listed in Table 3, A': ≤0.5 μM; B': >0.5 μM and ≤1 μM; C': >1.0 μM and ≤5 uM; D': >5 μM.

TABLE 3

| Example | ERK2 Biochemical Activity* | Colo 205 Cell Activity** |
|---------|---------------------------|--------------------------|
| 1 | A | A' |
| 2 | A | A' |
| 3 | A | A' |
| 4 | A | B' |
| 5 | A | A' |
| 6 | A | A' |
| 7 | A | A' |
| 8 |   | C' |
| 9 | A | A' |
| 9a | A | A' |
| 9b |   | C' |
| 10 | A | A' |
| 10a |   | C' |
| 10b |   | A' |
| 11 |   | A' |
| 12 |   | C' |
| 13 | B | A' |
| 14 | A | A' |
| 15 |   | B' |
| 16 |   | C' |
| 17 |   | B' |

*A: ≤10 nM; B: >10 nM and ≤100 nM; C: >100 nM and ≤1 uM; D: >1 μM.
**A': ≤0.5 μM; B': >0.5 μM and ≤1 μM; C': >1.0 μM and ≤5 μM; D': >5 μM.

The invention claimed is:
1. A compound of formula I:

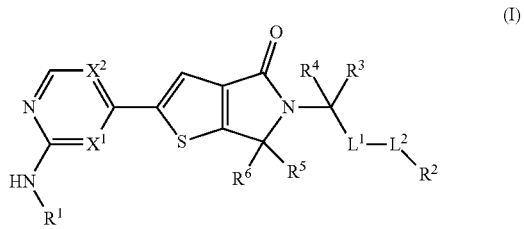

and/or a pharmaceutically acceptable salt thereof, wherein:

$R^1$ is an optionally substituted pyrazole, wherein the optional substituents for $R^1$ are 1-4 substituents independently selected from D, halo, —OH, Oxo, CN, N$_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms independently selected from N, O, and S as ring members, —CO$_2$R$^7$, —C(O)N(R$^{8a}$R$^{8b}$), —C(=NR$^9$)N(R$^{8a}$R$^{8b}$), —C(O)R$^7$, —SO$_{0-2}$R$^{10}$, —SO(=NR$^9$)R$^{10}$, —SO$_{1-2}$N(R$^{8a}$R$^{8b}$), —N(R$^{8a}$R$^{8b}$), —N(R$^{8a}$)C(O)R$^{10}$, —N(R$^{8a}$)C(=NR$^9$)R$^{10}$, —N(R$^{8a}$)SO$_{1-2}$R$^{10}$, —N(R$^{8c}$)C(O)N(R$^{8a}$R$^{8b}$), —N(R$^{8c}$)C(=NR$^9$)N(R$^{8a}$R$^{8b}$), —N(R$^{8c}$)SO$_{1-2}$N(R$^{8a}$R$^{8b}$) and —N(R$^{8a}$)CO$_2$R$^{10}$, wherein R$^7$, R$^{8a}$, R$^{8b}$ and R$^{8c}$ are independently H, or C1-C4 alkyl optionally substituted with 1-3 groups independently selected from D, halo, OH, NH$_2$, NHMe and NMe$_2$; R$^9$ is independently selected from H, CN, OH, C1-C4 alkyl and C1-C4 alkoxy; R$^{10}$ is C1-C4 alkyl optionally substituted with 1-3 groups independently selected from D, halo, OH, NH$_2$, NHMe and NMe$_2$; and two substituents on the same or adjacent carbon atoms of R$^1$ can optionally be taken together to form a 5-6 membered ring that can be saturated or aromatic and optionally contains 1-2 heteroatoms selected from N, O and S and can optionally be substituted with 1-2 groups independently selected from D, Me, halo, OH, oxo, C1-C4 alkoxy, NH$_2$, C1-C4 alkylamino and di(C1-C4 alkyl)amino;

R$^2$ is selected from phenyl and 5- to 6-membered heteroaryl containing 1-3 heteroatoms selected from N, O and S as ring members, wherein R$^2$ is optionally substituted with 1-3 substituents independently selected from of D, halo, —OH, =O, CN, N$_3$, CF$_3$, C1-C4 alkyl, C1-C4 alkoxy, C1-C4 haloalkyl, C1-C4 hydroxyalkyl, C1-C4 haloalkoxy, C3-C6 cycloalkyl, 4-8 membered heterocyclyl containing 1-2 heteroatoms selected from N, O, and S as ring members, —CO$_2$R$^{11}$, —C(O)N(R$^{12a}$R$^{12b}$), —C(=NR$^{13}$)N(R$^{12a}$R$^{12b}$), —C(O)R$^{11}$, —SO$_{0-2}$R$^{14}$, —SO(=NR$^{13}$)R$^{14}$, —SO$_{1-2}$N(R$^{12a}$R$^{12b}$), —N(R$^{12a}$R$^{12b}$), —N(R$^{12a}$)C(O)R$^{11}$, —N(R$^{12a}$)C(=NR$^{13}$)R$^{11}$, —N(R$^{12a}$)SO$_{1-2}$R$^{14}$, —N(R$^{12c}$)C(O)N(R$^{12a}$R$^{12b}$), —N(R$^{12c}$)C(=NR$^{13}$)N(R$^{12a}$R$^{12b}$), —N(R$^{12c}$)SO$_{1-2}$N(R$^{12a}$R$^{12b}$) and —N(R$^{12a}$)CO$_2$R$^{14}$; wherein R$^{11}$, R$^{12a}$, R$^{12b}$ and 11$^{12c}$ are independently selected from H, and C1-C4 alkyl optionally substituted with 1-3 groups independently selected from D, halo, OH, NH$_2$, NHMe, NMe$_2$ and C1-C4 alkoxy; R$^{13}$ is independently selected from H, CN, OH, C1-C4 alkyl, and C1-C4 alkoxy; R$^{14}$ is C1-C4 alkyl optionally substituted with 1-3 groups independently selected from D, halo, OH, NH$_2$, NHMe, NMe$_2$ and C1-C4 alkoxy;

R$^3$ is selected from H, D and F;

R$^4$ is selected from H, D, F, and C1-C4 alkyl optionally substituted with 1-3 substituents independently selected from D, halo, —OH, =O, CN, N$_3$, —CO$_2$R$^{15}$, —C(O)N(R$^{16a}$R$^{16b}$), —C(=NR$^{17}$)N(R$^{16a}$R$^{16b}$), —C(O)R$^{15}$, —SO$_{0-2}$R$^{18}$, —SO(=NR$^{17}$)R$^{18}$, —SO$_{1-2}$N(R$^{16a}$R$^{16b}$), —N(R$^{16a}$R$^{16b}$), —N(R$^{16a}$)C(O)R$^{15}$, —N(R$^{16a}$)C(=NR$^{17}$)R$^{15}$, —N(R$^{16a}$)SO$_{1-2}$R$^{18}$, —N(R$^{16c}$)C(O)N(R$^{16a}$R$^{16b}$), —N(R$^{16c}$)C(=NR$^{17}$)N(R$^{16a}$R$^{16b}$), —N(R$^{16c}$)SO$_{1-2}$N(R$^{16a}$R$^{16b}$) and —N(R$^{16a}$)CO$_2$R$^{18}$; wherein R$^{15}$, R$^{16a}$, R$^{16b}$ and 11$^{16c}$ are independently selected from H, and C1-C4 alkyl optionally substituted with 1-3 groups independently selected from D, halo, OH, NH$_2$, NHMe, NMe$_2$ and C1-C4 alkoxy; R$^{17}$ is independently selected from H, CN, OH, C1-C4 alkyl, and C1-C4 alkoxy; R$^{18}$ is C1-C4 alkyl optionally substituted with 1-3 groups independently selected from D, halo, OH, NH$_2$, NHMe, NMe$_2$ and C1-C4 alkoxy;

R$^5$ and R$^6$ are independently selected from H and an optionally substituted C1-C4 alkyl; wherein the optional substituents for R$^5$ and R$^6$ are 1-3 substituents independently selected from D, halo, —OH, C1-C4 alkyl, C1-C4 alkoxy, C1-C4 haloalkyl, C1-C4 haloalkoxy, and C3-C6 cycloalkyl;

R$^2$ and R$^4$ can optionally cyclize to form an additional C5-C6 cycloalkyl ring or a 5-6 membered heterocyclic ring containing 1-2 heteroatoms selected from N, O, and S;

R$^5$ and R$^6$ can optionally cyclize to form a C3-C6 cycloalkyl ring, a 4-6 membered heterocyclic ring containing 1-2 heteroatoms selected from N, O, and S;

L$^1$ is selected from a bond, —C(R$^{19a}$R$^{19b}$)—, —C(O)NR$^{20}$—, and —C(R19aR$^{19b}$)NR$^{20}$—, wherein R$^{19a}$, R$^{19b}$ and R$^{20}$ are independently selected from H and C1-C4 alkyl, each of which is optionally substituted with 1-3 groups independently selected from D, halo, OH, NH$_2$, NHMe, NMe$_2$ and C1-C4 alkoxy;

L$^2$ is selected from a bond and —C(R$^{21a}$R$^{21b}$)—, wherein R$^{21a}$ and R$^{21b}$ are independently selected from H and C1-C4 alkyl optionally substituted with 1-3 groups independently selected from D, halo, OH, NH$_2$, NHMe, NMe$_2$, —OPO$_3$H$_2$ and C1-C4 alkoxy;

X$^1$ is selected from CR$^{22a}$ and N; wherein R$^{22a}$ is selected from H, halo, CN, and C1-C3 alkyl; and X$^2$ is selected from CR$^{22b}$ and N; wherein R$^{22b}$ is selected from H, halo, CN, and C1-C3 alkyl.

2. The compound according to claim 1 or a pharmaceutically acceptable salt thereof, wherein X$^1$ and X$^2$ are N.

3. The compound according to claim 1 or a pharmaceutically acceptable salt thereof, wherein X$^1$ is CH and X$^2$ is CR$^{22b}$, wherein R$^{22b}$ is selected from H, halo, CN and C1-C3 alkyl.

4. The compound according to claim 1 or a pharmaceutically acceptable salt thereof, wherein X$^1$ is N and X$^2$ is CR$^{22b}$, wherein R$^{22b}$ is selected from H, halo, CN and C1-C3 alkyl.

5. The compound according to claim 1 or a pharmaceutically acceptable salt thereof, wherein R$^1$ is pyrazole, optionally substituted with one or two groups independently selected from Oxo, D, halo, CN, hydroxy, C1-C4 alkoxy, C1-C4 alkyl, C1-C4 haloalkyl, C1-C4 hydroxyalkyl, C1-C4 haloalkoxy, and C3-C6-cycloalkyl.

6. The compound of claim 1 or a pharmaceutically acceptable salt thereof, wherein R$^2$ is phenyl and is optionally substituted with up to three groups independently selected from halo, D, CN, C1-C4 alkoxy, C1-C4 alkyl, C1-C4 haloalkyl, C1-C4 haloalkoxy, C3-C6 cycloalkyl, —SR$^{26}$, —SO$_2$R$^{26}$, —N(R$^{27a}$R$^{27b}$), —N(R$^{27a}$)C(O)R$^{26}$ and —SO$_2$N(R$^{27a}$R$^{27b}$), wherein each R$^{27a}$ and R$^{27b}$ are independently selected from H, C1-C4 alkyl and C1-C4 haloalkyl; R$^{26}$ is C1-C4 alkyl.

7. The compound of claim 1 or a pharmaceutically acceptable salt thereof, wherein R$^2$ is thiophene, thiazole, pyridine, pyrimidine, pyrazine or pyridazine, and is optionally substituted with up to three groups independently selected from D, halo, CN, C1-C4 alkoxy, C1-C4 alkyl, C1-C4 haloalkyl, C1-C4 haloalkoxy, —SO$_2$R$^{28}$, —N(R$^{29a}$R$^{29b}$), —N(R$^{29a}$)C(O)R$^{28}$ and —SO$_2$N(R$^{29a}$R$^{29b}$), wherein each R$^{29a}$ and R$^{29b}$ are independently selected from H, C1-C4 alkyl and C1-C4 haloalkyl; R$^{28}$ is C1-C4 alkyl.

8. The compound of claim 1 or a pharmaceutically acceptable salt thereof, wherein R$^3$ is H, L$^1$ and L$^2$ are bonds; and R$^4$ is methyl or ethyl, and is optionally substituted with fluoro, amino, hydroxy, methylamino, ethylamino, dimethylamino, —OP(O)(OH)$_2$, methoxy or ethoxy.

9. The compound of claim 1 or a pharmaceutically acceptable salt thereof, wherein L$^1$ and L$^2$ are bonds; R$^3$ and R$^4$ are H or D.

10. The compound of claim 1 or a pharmaceutically acceptable salt thereof, wherein L$^1$ is —C(O)NH—.

11. The compound of claim 1, wherein the compound is of the Formula IA:

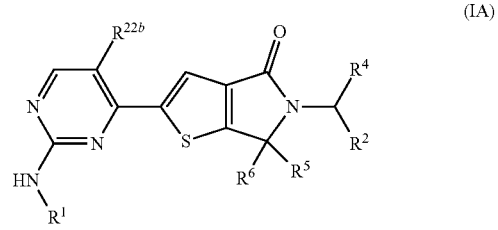

(IA)

or a pharmaceutically acceptable salt thereof, wherein R$^1$ is pyrazole, which can be substituted with up to two groups independently selected from D, F, Cl, Br, CN, Me, Et, Pr, i-Pr, cyclopropyl, butyl, isobutyl, sec-butyl, t-butyl, CH$_2$F, CHF$_2$, CF$_3$, MeO, EtO, i-PrO, PrO, BuO, t-BuO, s-BuO, i-BuO, OCF$_3$, —O(cyclopropyl), —(CH$_2$)$_2$OH, —(CH$_2$)$_2$OMe, —(CH$_2$)C(OH)CH$_2$OH, —(CH$_2$)$_2$NHSO$_2$NH$_2$, —C(OH)(CH$_3$)$_3$, —O(CH$_2$)$_2$OH, —O(CH$_2$)$_2$OMe, —O(CH$_2$)C(OH)CH$_2$OH and —O(CH$_2$)$_2$NHSO$_2$NH$_2$;

wherein R$^2$ is phenyl, pyridine or thienyl, optionally substituted with 1-2 groups independently selected from D, amino, halo, CF$_3$, CN, C1-C4 alkyl, C1-C4 alkoxy, C1-C4 haloalkyl, C1-C4 haloalkoxy, —COOR$^{30}$, —SO$_2$R$^{31}$, —N(R$^{32a}$R$^{32b}$), —N(R$^{32a}$)C(O)R$^{31}$, —SO$_2$N(R$^{32a}$R$^{32b}$) and —N(R$^{32a}$)SO$_2$R$^{31}$, wherein each R$^{30}$, R$^{32a}$ and R$^{32b}$ are independently selected from H and C1-C4 alkyl; R$^{31}$ is C1-C4 alkyl;

R$^4$ is selected from H, D and —CH$_2$R*, wherein R* is selected from H, —OH, F, —NH$_2$, —NHMe, —NMe$_2$, —OP(O)(OH)$_2$ and —OMe;

R$^5$ and R$^6$ are independently selected from H and an optionally substituted group selected from C1-C4 alkyl; wherein the optional substituents for R$^5$ and R$^6$ are 1-3 substituents independently selected from D, halo, —OH, C1-C4 alkoxy, C1-C4 haloalkoxy; wherein R⁵ and R⁶ can optionally cyclize to form a C3-C6 cycloalkyl ring or a 4-6 membered heterocyclic ring containing 1-2 heteroatoms selected from N, O, and S;

wherein R²²ᵇ is selected from H, halo, and C1-C3 alkyl.

12. The compound of claim 1, wherein the compound is of the Formula IB:

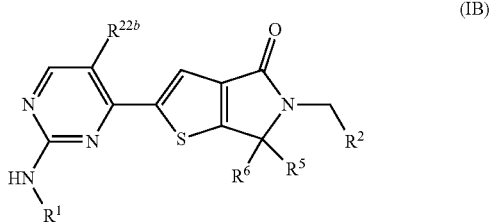

(IB)

wherein R¹ is pyrazole, which can be substituted with up to two groups independently selected from D, F, Cl, Br, CN, Me, Et, Pr, i-Pr, cyclopropyl, butyl, isobutyl, sec-butyl, t-butyl, CH₂F, CHF₂, CF₃, MeO, EtO, i-PrO, PrO, BuO, t-BuO, s-BuO, i-BuO, OCF₃, —O(cyclopropyl), —(CH₂)₂OH, —(CH₂)₂OMe, —(CH₂)C(OH)CH₂OH, —(CH₂)₂NHSO₂NH₂, —C(OH)(CH₃)₃, —O(CH₂)₂OH, —O(CH₂)₂OMe, —O(CH₂)C(OH)CH₂OH and —O(CH₂)₂NHSO₂NH₂;

wherein R² is phenyl, pyridine or thienyl, optionally substituted with 1-2 groups independently selected from D, amino, halo, CF₃, CN, C1-C4 alkyl, C1-C4 alkoxy, C1-C4 haloalkyl, C1-C4 haloalkoxy, —COOR³⁰, —SO₂R³¹, —N(R³²ᵃR³²ᵇ), —N(R³²ᵃ)C(O)R³¹, —SO₂N(R³²ᵃR³²ᵇ) and —N(R³²ᵃ)SO₂R³¹, wherein each R³⁰, R³²ᵃ and R³²ᵇ are independently selected from H and C1-C4 alkyl; R³¹ is C1-C4 alkyl;

R⁵ and R⁶ are independently selected from H and an optionally substituted group selected from C1-C4 alkyl; wherein the optional substituents for R⁵ and R⁶ are 1-3 substituents independently selected from D, halo, —OH, C1-C4 alkoxy, C1-C4 haloalkoxy; wherein R⁵ and R⁶ can optionally cyclize to form a C3-C6 cycloalkyl ring or a 4-6 membered heterocyclic ring containing 1-2 heteroatoms selected from N, O, and S;

wherein R²²ᵇ is selected from H, halo, and C1-C3 alkyl.

13. The compound of claim 1, wherein the compound is of the Formula IC:

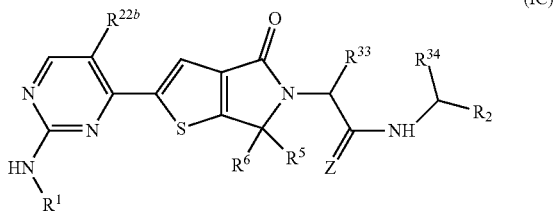

(IC)

wherein R¹ is pyrazole, which can be substituted with up to two groups independently selected from D, F, Cl, Br, CN, Me, Et, Pr, i-Pr, cyclopropyl, butyl, isobutyl, sec-butyl, t-butyl, CH₂F, CHF₂, CF₃, MeO, EtO, i-PrO, PrO, BuO, t-BuO, s-BuO, i-BuO, OCF₃, —O(cyclopropyl), —(CH₂)₂OH, —(CH₂)₂OMe, —(CH₂)C(OH)CH₂OH, —(CH₂)₂NHSO₂NH₂, —C(OH)(CH₃)₃, —O(CH₂)₂OH, —O(CH₂)₂OMe, —O(CH₂)C(OH)CH₂OH and —O(CH₂)₂NHSO₂NH₂;

wherein R² is phenyl, pyridine or thienyl, optionally substituted with 1-2 groups independently selected from D, amino, halo, CF₃, CN, C1-C4 alkyl, C1-C4 alkoxy, C1-C4 haloalkyl, C1-C4 haloalkoxy, —COOR³⁰, —SO₂R³¹, —N(R³²ᵃR³²ᵇ), —N(R³²ᵃ)C(O)R³¹, —SO₂N(R³²ᵃR³²ᵇ) and —N(R³²ᵃ)SO₂R³¹, wherein each R³⁰, R³²ᵃ and R³²ᵇ are independently selected from H and C1-C4 alkyl; R³¹ is C1-C4 alkyl;

R⁵ and R⁶ are independently selected from H and an optionally substituted group selected from C1-C4 alkyl; wherein the optional substituents for R⁵ and R⁶ are 1-3 substituents independently selected from D, halo, —OH, C1-C4 alkoxy, C1-C4 haloalkoxy; wherein R⁵ and R⁶ can optionally cyclize to form a C3-C6 cycloalkyl ring or a 4-6 membered heterocyclic ring containing 1-2 heteroatoms selected from N, O, and S;

wherein R²²ᵇ is selected from H, halo, and C1-C3 alkyl;

wherein R³³ is selected from H, D and —CH₂R#, wherein R# is selected from H and C1-C4 alkyl;

wherein R³⁴ is selected from H, D and —CH₂R*, wherein R* is selected from H, —OH, F, —NH₂, —NHMe, —NMe₂, —OP(O)(OH)₂ and —OMe;

wherein Z is O or 2H.

14. The compound of claim 1, wherein the compound is of the Formula ID:

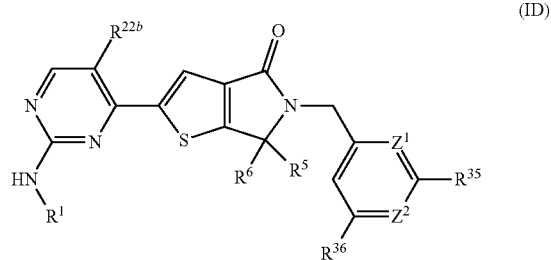

(ID)

wherein R¹ is pyrazole, which can be substituted with up to two groups independently selected from D, F, Cl, Br, CN, Me, Et, Pr, i-Pr, cyclopropyl, butyl, isobutyl, sec-butyl, t-butyl, CH₂F, CHF₂, CF₃, MeO, EtO, i-PrO, PrO, BuO, t-BuO, s-BuO, i-BuO, OCF₃, —O(cyclopropyl), —(CH₂)₂OH, —(CH₂)₂OMe, —(CH₂)C(OH)CH₂OH, —(CH₂)₂NHSO₂NH₂, —C(OH)(CH₃)₃, —O(CH₂)₂OH, —O(CH₂)₂OMe, —O(CH₂)C(OH)CH₂OH and —O(CH₂)₂NHSO₂NH₂;

R⁵ and R⁶ are independently selected from H and an optionally substituted group selected from C1-C4 alkyl; wherein the optional substituents for R⁵ and R⁶ are 1-3 substituents independently selected from D, halo, —OH, C1-C4 alkoxy, C1-C4 haloalkoxy; wherein R⁵ and R⁶ can optionally cyclize to form a C3-C6 cycloalkyl ring or a 4-6 membered heterocyclic ring containing 1-2 heteroatoms selected from N, O, and S;

wherein R²²ᵇ is selected from H, halo, and C1-C3 alkyl;

wherein R³⁵ and R³⁶ are independently selected from H, F, CN, —CF₃, OMe, OCF₃, SMe and an optional substituted group selected from C1-C4 alkyl, C3-C6 cycloalkyl and C1-C4 alkoxyl; wherein the optional substituents are 1-3 substituents independently selected from halogen;
wherein $Z^1$ and $Z^2$ are independently selected from CH and N.

15. The compound of claim 11, or a pharmaceutically acceptable salt thereof, wherein $R^1$ is selected from:

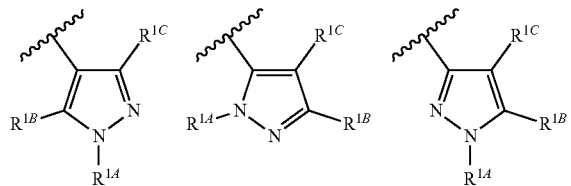

wherein each $R^{1A}$ is independently selected from H, Me, Et, propyl, isopropyl, cyclopropyl, butyl, t-butyl, sec-butyl, isobutyl, $CH_2F$, $CF_2H$ and $CF_3$; wherein $R^{1B}$, $R^{1C}$ and $R^{1D}$ are independently selected from H, Me, Et, propyl, isopropyl, cyclopropyl, butyl, t-butyl, sec-butyl, isobutyl, $CH_2F$, $CF_2H$, $CF_3$, MeO, EtO, PrO, i-PrO, c-PrO, BuO, t-BuO, s-BuO, i-BuO, $OCF_3$, c-PrO, $Me_3(OH)C—$, CN, Cl and F.

16. A selected from the following compounds and pharmaceutically acceptable salts thereof:
  6,6-dimethyl-2-(2-((1-methyl-1H-pyrazol-5-yl)amino)pyrimidin-4-yl)-5-((2-(trifluoromethyl)pyridin-4-yl)methyl)-5,6-dihydro-4H-thieno[2,3-c]pyrrol-4-one,
  5-(3-chlorobenzyl)-6,6-dimethyl-2-(2-(1-methyl-1H-pyrazol-5-ylamino)pyrimidin-4-yl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-((6-(trifluoromethyl)pyridin-2-yl)methyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-((6-(trifluoromethyl)pyridin-3-yl)methyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-((4-(trifluoromethyl)thiazol-2-yl)methyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-((2-(trifluoromethyl)pyrimidin-4-yl)methyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-((3-(trifluoromethyl)isoxazol-5-yl)methyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-(2-(2-(trifluoromethyl)pyridin-4-yl)ethyl)-5,6-dihydro-4H-thieno[2,3-c]pyrrol-4-one,
  6,6-dimethyl-2-(2-(1-methyl-1H-pyrazol-5-ylamino)pyrimidin-4-yl)-5-(1-(2-(trifluoromethyl)pyridin-4-yl)ethyl)-5,6-dihydro-4H-thieno[2,3-c]pyrrol-4-one,
  (R)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one,
  (S)-6,6-dimethyl-2-(2-((1-methyl-1H-pyrazol-5-yl)amino)pyrimidin-4-yl)-5-(1-(2-(trifluoromethyl)pyridin-4-yl)ethyl)-5,6-dihydro-4H-thieno[2,3-c]pyrrol-4-one,
  tert-butyl (4-(6,6-dimethyl-4-oxo-5-(1-(4-(trifluoromethyl)thiazol-2-yl)ethyl)-5,6-dihydro-4H-thieno[2,3-c]pyrrol-2-yl)pyrimidin-2-yl)(1-methyl-1H-pyrazol-5-yl)carbamate,
  (R)-2-bromo-6,6-dimethyl-5-(1-(4-(trifluoromethyl)thiazol-2-yl)ethyl)-5,6-dihydro-4H-thieno[2,3-c]pyrrol-4-one,
  (S)-2-bromo-6,6-dimethyl-5-(1-(4-(trifluoromethyl)thiazol-2-yl)ethyl)-5,6-dihydro-4H-thieno[2,3-c]pyrrol-4-one,
  (S)-5-(1-(3-chlorophenyl)-2-hydroxyethyl)-6,6-dimethyl-2-(2-((1-methyl-1H-pyrazol-5-yl)amino)pyrimidin-4-yl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-(1-(6-(trifluoromethyl)pyridin-2-yl)ethyl)-5,6-dihydro-4H-thieno[2,3-c]pyrrol-4-one,
  6,6-dimethyl-2-(2-((1-methyl-1H-pyrazol-5-yl)amino)pyrimidin-4-yl)-5-(1-(2-(trifluoromethyl)pyrimidin-4-yl)ethyl)-5,6-dihydro-4H-thieno[2,3-c]pyrrol-4-one,
  (S)—N-(1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)acetamide,
  N—((S)-1-(3-chlorophenyl)-2-hydroxyethyl)-2-(6,6-dimethyl-2-(2-((1-methyl-1H-pyrazol-5-yl)amino)pyrimidin-4-yl)-4-oxo-4H-thieno[2,3-c]pyrrol-5(6H)-yl)propanamide,
  2-(6,6-dimethyl-2-(2-((1-methyl-1H-pyrazol-5-yl)amino)pyrimidin-4-yl)-4-oxo-4H-thieno[2,3-c]pyrrol-5(6H)-yl)-N-((2-(trifluoromethyl)pyridin-4-yl)methyl)acetamide, and
  (S)-5-(2-((1-(3-chlorophenyl)-2-hydroxyethyl)amino)ethyl)-6,6-dimethyl-2-(2-((1-methyl-1H-pyrazol-5-yl)amino)pyrimidin-4-yl)-5,6-dihydro-4H-thieno[2,3-c]pyrrol-4-one.

17. A pharmaceutical composition comprising a compound according to claim 1 admixed with at least one pharmaceutically acceptable excipient.

18. The pharmaceutical composition of claim 17, further comprising a therapeutic co-agent.

19. The pharmaceutical composition of claim 18, wherein the therapeutic co-agent is selected from anticancer compounds, analgesics, and anti-inflammatory compounds.

* * * * *